(12) United States Patent
Liu et al.

(10) Patent No.: US 11,168,088 B2
(45) Date of Patent: Nov. 9, 2021

(54) PYRIDYLAMINO SUBSTITUTED HETEROTRICYCLIC COMPOUNDS, AND PREPARATION METHOD AND PHARMACEUTICAL USE THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Yang Liu, Shanghai (CN); Jiangwei Wang, Shanghai (CN); Qing Zhang, Shanghai (CN); Yonggang Chen, Shanghai (CN); Baoxin Xi, Shanghai (CN); Wangbin Sun, Shanghai (CN); Yingtao Liu, Shanghai (CN); Xi Chen, Shanghai (CN)

(73) Assignees: SHANGHAI HAIYAN PHARMACEUTICAL TECHNOLOGY CO., LTD.; YANGTZE RIVER PHARMACEUTICAL GROUP CO., LTD.

( * ) Notice: Subject to any disclaimer, the term of this patent is extended or adjusted under 35 U.S.C. 154(b) by 31 days.

(21) Appl. No.: 16/338,379

(22) PCT Filed: Nov. 10, 2017

(86) PCT No.: PCT/CN2017/110463
§ 371 (c)(1),
(2) Date: Mar. 29, 2019

(87) PCT Pub. No.: WO2018/086591
PCT Pub. Date: May 17, 2018

(65) Prior Publication Data
US 2020/0039983 A1    Feb. 6, 2020

(30) Foreign Application Priority Data

Nov. 11, 2016  (CN) .......................... 201610994416.9

(51) Int. Cl.
| | |
|---|---|
| *C07D 487/04* | (2006.01) |
| *C07D 487/10* | (2006.01) |
| *C07D 491/147* | (2006.01) |
| *C07D 495/14* | (2006.01) |
| *A61K 31/519* | (2006.01) |
| *A61P 35/00* | (2006.01) |

(52) U.S. Cl.
CPC .......... *C07D 487/04* (2013.01); *A61K 31/519* (2013.01); *A61P 35/00* (2018.01); *C07D 487/10* (2013.01); *C07D 491/147* (2013.01); *C07D 495/14* (2013.01)

(58) Field of Classification Search
CPC .. C07D 487/04; C07D 487/14; C07D 495/14; C07D 491/147; A61K 31/519; A61P 35/00
USPC .......................................... 544/251; 514/257
See application file for complete search history.

(56) References Cited

U.S. PATENT DOCUMENTS

| | | |
|---|---|---|
| 2005/0148603 A1 | 7/2005 | Jimenez et al. |
| 2012/0183577 A1 | 7/2012 | Jimenez et al. |
| 2012/0238542 A1 | 9/2012 | Treu |
| 2013/0237544 A1 | 9/2013 | Tavares et al. |
| 2013/0338148 A1 | 12/2013 | Traquandi et al. |
| 2014/0350244 A1 | 11/2014 | Connors et al. |
| 2015/0246926 A1 | 9/2015 | Tavares et al. |

FOREIGN PATENT DOCUMENTS

| | | |
|---|---|---|
| CN | 1894258 A | 1/2007 |
| CN | 101945867 A | 1/2011 |
| CN | 103097388 A | 5/2013 |
| CN | 103429243 A | 12/2013 |
| JP | 2007502851 A | 2/2007 |

(Continued)

OTHER PUBLICATIONS

Krystofetal. Current Pharmaceutical Design, 2012, 18, 2883-2890.*
Wesierska-Gadek et al. Expert Opin. Investig. Drugs (2011) 20(12): 1611-1628.*
Golub et al., Science, 286, 531-537, 1999.*
Cecil Textbook of Medicine, edited by Bennet, J.C., and Plum F., 20th edition, vol. 1, 1004-1010, 1996.*

(Continued)

*Primary Examiner* — Venkataraman Balasubramanian
(74) *Attorney, Agent, or Firm* — Adsero IP

(57) ABSTRACT

The present disclosure relates to pyridinamine-substituted heterotriclo compounds, a preparation method thereof, and a use thereof in medicines. Specifically, a compound of formula (I), or a pharmaceutically acceptable salt, stereoisomer, solvate, or prodrug thereof, a preparation method and a use thereof are disclosed, wherein the groups in the formula (I) are as defined in the Description and claims.

20 Claims, No Drawings

(56) References Cited

FOREIGN PATENT DOCUMENTS

| JP | 2007509848 A | 4/2007 |
|---|---|---|
| JP | 2011507849 A | 3/2011 |
| JP | 2013532652 A | 8/2013 |
| JP | 2013543845 A | 12/2013 |
| WO | 2004/104007 A1 | 12/2004 |
| WO | 2009/085185 A1 | 7/2009 |
| WO | 2015/180642 A1 | 12/2015 |
| WO | 2015180642 A1 | 12/2015 |

OTHER PUBLICATIONS

Freshney etalCulture of Animal Cells, a Manual of Basic Technique, Alan R. Liss, Inc., 1983, New York, p. 4.*
Dermer et al., Bio/Technology, 1994, 12:320.*
Kwapisz D. . Breast Cancer Res Treat. Nov. 2017, 166(1) 41-54. PubMed Abstract provided.*
Office Action for Canadian application 3,039,012, dated May 1, 2020, 5 pages.
Office Action for Japanese application 2019-544762, dated Mar. 4, 2020, along with the English translation, 11 pages.
International Search Report for PCT/CN2017/110463, dated Feb. 9, 2018, 12 pages, with English Translation.
Extended European Search Report for Application No. 17868712.5, dated Jan. 3, 2020, 9 pages.
Zhao et al., "Synthesis and SAR of 4,5-dihydro-1H-pyrazolo{4,3-h]quinazoline derivatives as potent and selective CDK4/6 inhibitors", European Journal of Medicinal Chemistry 157 (2018) 935-945.

* cited by examiner

PYRIDYLAMINO SUBSTITUTED HETEROTRICYCLIC COMPOUNDS, AND PREPARATION METHOD AND PHARMACEUTICAL USE THEREOF

CROSS-REFERENCE TO RELATED APPLICATION

This application claims priority to and is a 35 U.S.C. § 371 national phase application of PCT/CN2017/110463 (WO 2018/086591 A1), filed on Nov. 10, 2017 entitled "PYRIDYLAMINO SUBSTITUTED HETEROTRICYCLIC COMPOUNDS, AND PREPARATION METHOD AND PHARMACEUTICAL USE THEREOF", which application claims priority to and the benefit of Chinese Application CN 201610994416.9 filed Nov. 11, 2016; the disclosures of which are incorporated herein by reference in their entirety.

TECHNICAL FIELD

The disclosure belongs to the field of medical technology. In particular, the present disclosure particularly relates to a pyridylamino substituted heterotricyclic compound, its preparation method and use as a CDK4/6 inhibitor, and pharmaceutical compositions prepared therefrom.

BACKGROUND

CDKs are a class of serine/threonine protein kinases. A CDK does not have kinase activity until it binds to a cyclin, and the CDK plays a key role in the initiation of a cell cycle and in the conversion and regulation for various periods. CDK4/6 is an important cell cycle regulatory protein that phosphorylates the anti-oncogene protein Rb, releases the E2F transcription factor, and allows cells to successfully pass the cell cycle G1/S checkpoint, allowing the cell cycle to continue. A CDK4 single gene knockout mouse has both diabete and cell defect. A CDK6 single gene knockout mouse causes mild anemia due to defects in hematopoietic cell proliferation. While CDK4 and CDK6 (CDK4/6) double-gene knockout impaires the proliferative capacity of hematopoietic progenitor cells, resulting in late embryonic death of the double-gene knockout mouse. In tumor cells, the hyperactivation of CDK4/6-cyclin D/Rb signaling pathway has generally been found. Under the stimulation of various intracellular and extracellular mitotic signals, high expression of cyclin D regulates the interaction between CDK4/6 protein and cyclin D, and promotes the localization and kinase activity of CDK4/6. Activated CDK4/6 inhibits the activity of Rb tumor suppressor protein by phosphorylation, dissociates the Rb-E2F complex, releases free E2F into the nucleus, regulates protein transcription, and initiates cell cycle progression. Hyperactivation of CDK4 has often been found in epithelial cell malignancies, and hyperactivation of CDK6 has often been often found in mesenchymal cell tumors such as sarcoma and hematological cancers. By constructing a tumor-bearing mouse model of breast cancer, it was found that tumor was developed in all the wild-type nude mice, but not in CDK4 knockout nude mice at all. By interfering with the expression of CDK4 using anti-CDK4 siRNA, it was found that tumor growth in nude mice was significantly inhibited. Selective CDK4/6 inhibitors can induce the block of G1 cell phase, thereby increasing the tolerance of hematopoietic stem/progenitor cells to DNA damaging agents such as IR, and effectively reducing the various hematopoietic toxicities induced by radiation, including myelosuppression, neutropenia, leukopenia, anemia, etc.

In recent years, major companies have identified and found a series of inhibitors such as Pfizer's palbociclib, Eli Lilly's Abemaciclib, which selectively inhibit CDK4 and CDK6, and are used to treat diseases such as cancers, cardiovascular disorders and inflammation. In addition, a number of domestic companies also have patent disclosures. Patent applications of selective inhibition of CDK4 and CDK6 include WO2014183520, WO2015101293, WO2015180642, WO2016014904 and WO2016015597. Although these small molecule CDK inhibitors currently have certain advantages in clinical practice, they also have their own shortcomings, for example, palbociclib has relatively great neutrophil toxicity. It is generally believed that inhibition of CDK4 can inhibit the growth of tumor cells, while CDK6 is highly expressed in the blood system and functions to regulate the growth of hematopoietic cells, etc., therefore, the inhibition of CDK6 may cause hematological toxicity, such as neutrophils reduction, red blood cell reduction, etc. Palbociclib has the same inhibition of both CDK4 and CDK6, with enzyme activities of 10 nm and 10 nm, respectively, and its toxicity should be related to this. While the inhibition of CDK4 by Abemaciclib is stronger than that of CDK6; the weak CDK6 inhibitor causes low hematological toxicity. Since the homology between CDK4 and CDK6 is very high, i.e., about 70%, the development of selective CDK4/6 inhibitors, especially CDK4 inhibitors, is a great challenge.

In addition, brain metastases occur in a significant proportion of advanced cancer patients, which is particularly prominent in lung cancer, breast cancer, and melanoma; for this portion of patients, using the existing treatment method to treat them will have very poor effect, this mainly because most of the drugs cannot enter the blood-brain barrier, so if selective CDK4/6 inhibitors which have unique pharmacokinetic characteristics, can effectively penetrate the blood-brain barrier, and have significant efficacy for patients with brain tumors or brain metastases with the current clinical significant needs can be developed, they will have important clinical significance and broad market prospects. In order to achieve a better therapeutic effect on tumors and better meet market demands, we hope to develop a new generation of highly efficient and low-toxic selective CDK4 and CDK6 inhibitors.

SUMMARY OF THE INVENTION

The object of the present disclosure is to provide a compound with a novel structure, which compound can act as a selective CDK4/6 inhibitor.

In the first aspect, the present disclosure provides a compound represented by formula (I), or a pharmaceutically acceptable salt, stereoisomer, solvate or prodrug thereof:

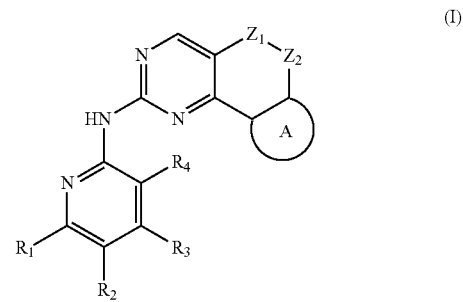

wherein, $R_1$, $R_3$, $R_4$ are each independently hydrogen, halogen (preferably fluorine, chlorine, bromine), $C_{1-8}$ alkyl (preferably $C_{1-6}$ alkyl, more preferably $C_{1-3}$ alkyl) or halogenated $C_{1-8}$ alkyl (preferably halogenated $C_{1-6}$ alkyl, more preferably halogenated $C_{1-3}$ alkyl);

$R_2$ is —$(CH_2)_n$—Y, wherein Y is $C_{3-8}$ cycloalkyl (preferably $C_{3-6}$ cycloalkyl), 3 to 6 membered saturated single heterocycle (preferably 4 to 6 membered), 5 to 6 membered monocyclic heteroaryl ring, 8 to 10 membered bicyclic heteroaryl ring, spiro, spiroheterocycle, bridged ring or bridged heterocycle; n is 0, 1 or 2;

$Z_1$, $Z_2$ are each independently a bond, $CR_aR_b$, $NR_c$, O, S or $S(O)_2$, and $Z_1$, $Z_2$ are not a bond, $NR_c$, O, S or $S(O)_2$ at the same time;

$R_a$, $R_b$ are each independently hydrogen, halogen (preferably fluorine, chlorine, bromine), $C_{1-8}$ alkyl (preferably $C_{1-6}$ alkyl, more preferably $C_{1-3}$ alkyl), or halogenated $C_{1-8}$ alkyl (preferably halogenated $C_{1-6}$ alkyl, more preferably halogenated $C_{1-3}$ alkyl); or $R_a$, $R_b$ and the carbon atom attached thereto form a 3 to 6 membered saturated single heterocycle, 3 to 6 membered saturated or partially unsaturated monocyclic ring;

$R_c$ is hydrogen, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), $C(O)$ $C_{1-8}$ alkyl (preferably $C(O)C_{1-6}$ alkyl, more preferably $C(O)$ $C_{1-3}$ alkyl), $C(O)OC_{1-8}$ alkyl (preferably $C(O)OC_{1-6}$ alkyl, more preferably $C(O)OC_{1-3}$ alkyl), $CONR_{a1}R_{b1}$, —$SO_2C_{1-8}$ alkyl (preferably —$SO_2C_{1-6}$ alkyl, more preferably —$SO_2C_{1-3}$ alkyl), —$C(O)CH_2CN$, —$C(O)CH_2OH$, 3 to 6 membered saturated single heterocycle, 5 to 6 membered monocyclic heteroaryl ring, 8 to 10 membered bicyclic heteroaryl ring, spiro, spiroheterocycle, bridged ring or bridged heterocycle;

The ring A is the structure represented by formula (A-1), formula (A-2), formula (A-3) or formula (A-4):

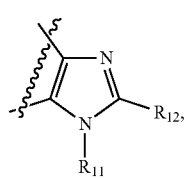

(A-1)

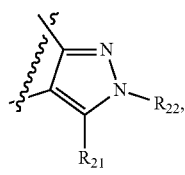

(A-2)

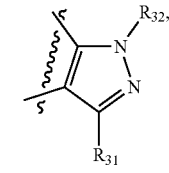

(A-3)

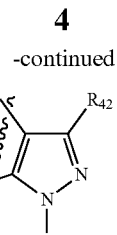

(A-4)

wherein $R_{11}$, $R_{22}$, $R_{32}$, $R_{41}$ are each independently hydrogen, $C_{1-8}$ alkyl, halogenated $C_{1-8}$ alkyl, $C_{3-8}$ cycloalkyl or 3 to 6 membered saturated single heterocycle (preferably 4 to 6 membered, more preferably 5 to 6 membered);

$R_{12}$, $R_{21}$, $R_{31}$, $R_{42}$ are each independently hydrogen, halogen, $C_{1-8}$ alkyl, halogenated $C_{1-8}$ alkyl, $C_{3-8}$ cycloalkyl or 3 to 6 membered saturated single heterocycle (preferably 4 to 6 membered, more preferably 5 to 6 membered);

the alkyl, alkoxy, cycloalkyl, 3 to 6 membered saturated single heterocycle, 5 to 6 membered monocyclic heteroaryl ring, 8 to 10 membered bicyclic heteroaryl ring, spiro, spiroheterocycle, bridged ring or bridged heterocycle are unsubstituted or substituted with 1, 2 or 3 substituents selected from the group consisting of CN, acetyl, hydroxy, hydroxymethyl, hydroxyethyl, carboxyl, halogen, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), halogenated $C_{1-8}$ alkoxy (preferably halogenated $C_{1-6}$ alkoxy, more preferably halogenated $C_{1-3}$ alkoxy), —$C(O)OC_{1-6}$ alkyl, $NR_{a2}R_{b2}$, 3 to 6 membered saturated single heterocycle, 5 to 6 membered monocyclic heteroaryl ring, 8 to 10 membered bicyclic heteroaryl ring, spiro, spiroheterocycle, bridged ring or bridged heterocycle;

$R_{a1}$, $R_{b1}$, $R_{a2}$, $R_{b2}$ are each independently hydrogen, $C_{1-8}$ alkyl (preferably $C_{1-6}$ alkyl, more preferably $C_{1-3}$ alkyl) or $C_{1-8}$ alkyl substituted with $C_{1-8}$ alkoxy (preferably $C_{1-6}$ alkyl substituted with $C_{1-6}$ alkoxy, more preferably $C_{1-3}$ alkyl substituted with $C_{1-3}$ alkoxy).

In another preferred example, Y is $C_{3-6}$ cycloalkyl, 4 to 6 membered saturated single heterocycle, 5 to 6 membered monocyclic heteroaryl ring, spiro, spiroheterocycle, bridged ring or bridged heterocycle, wherein the cycloalkyl, 4 to 6 membered saturated single heterocycle, 5 to 6 membered monocyclic heteroaryl ring, spiro, spiroheterocycle, bridged ring or bridged heterocycle are unsubstituted or substituted with —$(CH_2)_m$-$L_1$; $L_1$ is CN, acetyl, hydroxy, hydroxymethyl, hydroxyethyl, carboxyl, —$C(O)OC_{1-6}$ alkyl, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), halogenated $C_{1-8}$ alkyl (preferably halogenated $C_{1-6}$ alkyl, more preferably halogenated $C_{1-3}$ alkyl), $NR_{a2}R_{b2}$, $C_{1-8}$ alkoxy (preferably $C_{1-6}$ alkoxy, more preferably $C_{1-3}$ alkoxy), azetidine, oxetane, tetrahydrothiophene, pyrrolidine, tetrahydrofuran, piperidine, oxazolidine, piperazine, dioxolane, dioxane, morpholine, thiomorpholine, thiomorpholine-1,1-dioxide or tetrahydropyrane; m is 0, 1 or 2; $R_{a2}$, $R_{b2}$ are as previously defined.

In another preferred example, m is 0 or 1.

In another preferred example, the 4 to 6 membered saturated single heterocycle is azetidine, oxetane, pyrrolidine, tetrahydrofuran, piperidine, piperazine, morpholine or tetrahydropyrane.

In another preferred example, the $C_{3-6}$ cycloalkyl is cyclobutyl, cyclopentyl or cyclohexyl.

In another preferred example, the 5 to 6 membered monocyclic heteroaryl ring is thiophene, N-alkylpyrrole, furan, thiazole, imidazole, oxazole, pyrrole, pyrazol, triazole, tetrazole, isooxazole, oxadiazole, thiadiazole, pyridine, pyridazine, pyrimidine or pyrazine.

In another preferred example, the spiroheterocycle is a bicyclic spiroheterocycle containing 1-2 nitrogen or oxygen atoms.

In another preferred example, the bridged heterocycle is a bicyclic bridged heterocycle containing 1-2 nitrogen or oxygen atoms.

In another preferred example, azetidine, oxetane, tetrahydrothiophene, pyrrolidine, tetrahydrofuran, piperidine, oxazolidine, piperazine, dioxolane, dioxane, morpholine, thiomorpholine, thiomorpholine-1, 1-dioxide or tetrahydropyrane in $L_1$ is unsubstituted or substituted with 1, 2 or 3 substituents selected from the group consisting of acetyl, hydroxy, hydroxymethyl, hydroxyethyl, carboxyl, $C_{1-3}$ alkyl, $C_{1-3}$ alkoxy, halogenated $C_{1-3}$ alkyl, $C_{3-6}$ cycloalkyl, halogenated $C_{1-3}$ alkoxy, —C(O)OC$_{1-6}$ alkyl, NR$_{a3}$R$_{b3}$; wherein R$_{a3}$, R$_{b3}$ are each independently hydrogen or $C_{1-3}$ alkyl.

In another preferred example, Y is a group selected from: cyclobutyl, cyclopentyl, cyclohexyl, azetidine, pyrrolidine, tetrahydrofuran, piperidine, piperazine, morpholine or tetrahydropyrane, wherein the Y group is unsubstituted or substituted with $L_1$ or —CH$_2$-L$_1$; $L_1$ is CN, acetyl, hydroxy, hydroxymethyl, hydroxyethyl, carboxyl, —C(O)OCH$_3$, —C(O)OCH$_2$CH$_3$, —C(O)OC(CH$_3$)$_3$, —C(O)OCH(CH$_3$)$_2$, methyl, ethyl, n-propyl, isopropyl, cyclopropyl, cyclopentyl, cyclohexyl, monofluoromethyl, difluoromethyl, trifluoromethyl, monofluoroethyl, difluoroethyl, trifluoroethyl, methoxy, ethoxy, propoxy, isopropoxy, azetidine, pyrrolidine, tetrahydrofuran, piperidine, piperazine, morpholine, tetrahydropyrane or NR$_{a2}$R$_{b2}$; R$_{a2}$, R$_{b2}$ are each independently hydrogen, $C_{1-3}$ alkyl or $C_{1-3}$ alkyl substituted with $C_{1-3}$ alkoxy.

In another preferred example, azetidine, pyrrolidine, tetrahydrofuran, piperidine, piperazine, morpholine or tetrahydropyrane in $L_1$ is unsubstituted or substituted with 1, 2 or 3 substituents selected from the group consisting of acetyl, hydroxy, hydroxymethyl, hydroxyethyl, carboxyl, $C_{1-3}$ alkyl, $C_{1-3}$ alkoxy, halogenated $C_{1-3}$ alkyl, $C_{3-6}$ cycloalkyl, halogenated $C_{1-3}$ alkoxy, —C(O)OC$_{1-6}$ alkyl, NR$_{a3}$R$_{b3}$; wherein R$_{a3}$, R$_{b3}$ are each independently hydrogen or $C_{1-3}$ alkyl.

In another preferred example, R$_c$ is hydrogen, —C(O)C$_{1-3}$ alkyl, —C(O)OC$_{1-3}$ alkyl, —CONR$_{a1}$R$_{b1}$, —SO$_2$C$_{1-3}$ alkyl, —C(O)CH$_2$CN, —C(O)CH$_2$OH or —(CH$_2$)$_p$-L$_2$; wherein $L_2$ is CN, $C_{1-8}$ alkyl (preferably $C_{1-6}$ alkyl, more preferably $C_{1-3}$ alkyl), NR$_{a1}$R$_{b1}$, $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), 4 to 6 membered saturated single heterocycle, 5 to 6 membered monocyclic heteroaryl ring, spiro, spiroheterocycle, bridged ring or bridged heterocycle; p is 0, 1 or 2;

the alkyl, alkoxy, cycloalkyl, 4 to 6 membered saturated single heterocycle, 5 to 6 membered monocyclic heteroaryl ring, spiro, spiroheterocycle, bridged ring or bridged heterocycle is unsubstituted or substituted with one substituent selected from the group consisting of acetyl, hydroxy, hydroxymethyl, hydroxyethyl, carboxyl, —C(O)OC$_{1-6}$ alkyl, $C_{1-3}$ alkyl, $C_{1-3}$ alkoxy, halogenated $C_{1-3}$ alkyl, $C_{3-6}$ cycloalkyl, NR$_{a2}$R$_{b2}$, azetidine, oxetane, tetrahydrothiophene, pyrrolidine, tetrahydrofuran, piperidine, oxazolidine, piperazine, dioxolane, dioxane, morpholine, thiomorpholine, thiomorpholine-1, 1-dioxide or tetrahydropyrane; R$_{a1}$, R$_{b1}$, R$_{a2}$, R$_{b2}$ are as previously defined.

In another preferred example, p is 0 or 1.

In another preferred example, the 4 to 6 membered saturated single heterocycle is azetidine, oxetane, pyrrolidine, tetrahydrofuran, piperidine, piperazine, morpholine or tetrahydropyrane.

In another preferred example, the 5 to 6 membered monocyclic heteroaryl ring is thiophene, N-alkyl pyrrole, furan, thiazole, imidazole, oxazole, pyrrole, pyrazol, triazole, tetrazole, isooxazole, oxadiazole, thiadiazole, pyridine, pyridazine, pyrimidine or pyrazine.

In another preferred example, among the substituents, the azetidine, oxetane, tetrahydrothiophene, pyrrolidine, tetrahydrofuran, piperidine, oxazolidine, piperazine, dioxolane, dioxane, morpholine, thiomorpholine, thiomorpholine-1, 1-dioxide or tetrahydropyrane is unsubstituted or substituted with 1, 2 or 3 substituents selected from the group consisting of acetyl, hydroxy, hydroxymethyl, hydroxyethyl, carboxyl, $C_{1-3}$ alkyl, $C_{1-3}$ alkoxy, halogenated $C_{1-3}$ alkyl, $C_{3-6}$ cycloalkyl, halogenated $C_{1-3}$ alkoxy, —C(O)OC$_{1-6}$ alkyl, NR$_{a3}$R$_{b3}$; wherein R$_{a3}$, R$_{b3}$ are each independently hydrogen or $C_{1-3}$ alkyl.

In another preferred example, R$_{11}$, R$_{22}$, R$_{32}$, R$_{41}$ are each independently hydrogen or —(CH$_2$)$_q$-L$_3$; wherein $L_3$ is CN, NR$_{a1}$R$_{b1}$, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), 4 to 6 membered saturated single heterocycle, 5 to 6 membered monocyclic heteroaryl ring, spiro, spiroheterocycle, bridged ring or bridged heterocycle; q is 0, 1 or 2;

the alkyl, alkoxy, cycloalkyl, 4 to 6 membered saturated single heterocycle, 5 to 6 membered monocyclic heteroaryl ring, spiro, spiroheterocycle, bridged ring or bridged heterocycle is unsubstituted or substituted with one substituent selected from the group consisting of acetyl, hydroxy, hydroxymethyl, hydroxyethyl, carboxyl, —C(O)OC$_{1-6}$ alkyl, $C_{1-3}$ alkyl, $C_{1-3}$ alkoxy, halogenated $C_{1-3}$ alkyl, $C_{3-6}$ cycloalkyl, NR$_{a2}$R$_{b2}$, azetidine, oxetane, tetrahydrofuran, tetrahydrothiophene, pyrrolidine, piperidine, oxazolidine, piperazine, dioxolane, dioxane, morpholine, thiomorpholine, thiomorpholine-1, 1-dioxide or tetrahydropyrane; R$_{a1}$, R$_{b1}$, R$_{a2}$, R$_{b2}$ are as previously defined.

In another preferred example, q is 0 or 1.

In another preferred example, the 4 to 6 membered saturated single heterocycle is azetidine, oxetane, pyrrolidine, tetrahydrofuran, piperidine, piperazine, morpholine or tetrahydropyrane.

In another preferred example, the 5 to 6 membered monocyclic heteroaryl ring is thiophene, N-alkyl pyrrole, furan, thiazole, imidazole, oxazole, pyrrole, pyrazol, triazole, tetrazole, isooxazole, oxadiazole, thiadiazole, pyridine, pyridazine, pyrimidine or pyrazine.

In another preferred example, among the substituents, the azetidine, oxetane, tetrahydrofuran, tetrahydrothiophene, pyrrolidine, piperidine, oxazolidine, piperazine, dioxolane, dioxane, morpholine, thiomorpholine, thiomorpholine-1, 1-dioxide or tetrahydropyrane is unsubstituted or substituted with 1, 2 or 3 substituents selected from the group consisting of acetyl, hydroxy, hydroxymethyl, hydroxyethyl, carboxyl, $C_{1-3}$ alkyl, $C_{1-3}$ alkoxy, halogenated $C_{1-3}$ alkyl, $C_{3-6}$ cycloalkyl, halogenated $C_{1-3}$ alkoxy, —C(O)OC$_{1-6}$ alkyl, NR$_{a3}$R$_{b3}$; wherein R$_{a3}$, R$_{b3}$ are each independently hydrogen or $C_{1-3}$ alkyl.

In another preferred example, $R_{12}$, $R_{21}$, $R_{31}$, $R_{42}$ are each independently hydrogen, halogen or —$(CH_2)_r$-$L_4$; $L_4$ is CN, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), $NR_{a1}R_{b1}$, 4 to 6 membered saturated single heterocycle, 5 to 6 membered monocyclic heteroaryl ring, spiro, spiroheterocycle, bridged ring or bridged heterocycle; r is 0, 1 or 2; the alkyl, alkoxy, cycloalkyl, 4 to 6 membered saturated single heterocycle, 5 to 6 membered monocyclic heteroaryl ring, spiro, spiroheterocycle, bridged ring or bridged heterocycle is unsubstituted or substituted with one substituent selected from the group consisting of acetyl, hydroxy, hydroxymethyl, hydroxyethyl, carboxyl, —C(O)OC$_{1-6}$ alkyl, $C_{1-3}$ alkyl, $C_{1-3}$ alkoxy, halogenated $C_{1-3}$ alkyl, $C_{3-6}$ cycloalkyl, $NR_{a2}R_{b2}$, azetidine, oxetane, tetrahydrofuran, tetrahydrothiophene, pyrrolidine, piperidine, oxazolidine, piperazine, dioxolane, dioxane, morpholine, thiomorpholine, thiomorpholine-1,1-dioxide or tetrahydropyrane; $R_{a1}$, $R_{b1}$, $R_{a2}$, $R_{b2}$ are as previously defined.

In another preferred example, r is 0 or 1.

In another preferred example, the 4 to 6 membered saturated single heterocycle is azetidine, oxetane, pyrrolidine, tetrahydrofuran, piperidine, piperazine, morpholine or tetrahydropyrane.

In another preferred example, the 5 to 6 membered monocyclic heteroaryl ring is thiophene, N-alkyl pyrrole, furan, thiazole, imidazole, oxazole, pyrrole, pyrazol, triazole, tetrazole, isooxazole, oxadiazole, thiadiazole, pyridine, pyridazine, pyrimidine or pyrazine.

In another preferred example, the azetidine, oxetane, tetrahydrofuran, tetrahydrothiophene, pyrrolidine, piperidine, oxazolidine, piperazine, dioxolane, dioxane, morpholine, thiomorpholine, thiomorpholine-1, 1-dioxide or tetrahydropyrane in the substituent is unsubstituted or substituted with 1, 2 or 3 substituents selected from the group consisting of acetyl, hydroxy, hydroxymethyl, hydroxyethyl, carboxyl, $C_{1-3}$ alkyl, $C_{1-3}$ alkoxy, halogenated $C_{1-3}$ alkyl, $C_{3-6}$ cycloalkyl, halogenated $C_{1-3}$ alkoxy, —C(O)OC$_{1-6}$ alkyl, $NR_{a3}R_{b3}$; wherein $R_{a3}$, $R_{b3}$ are each independently hydrogen or $C_{1-3}$ alkyl.

In another preferred example, $R_a$, $R_b$ are each independently hydrogen, fluorine, chlorine, $C_{1-3}$ alkyl, halogenated $C_{1-3}$ alkyl; or $R_a$, $R_b$ and the carbon atom attached thereto form a epoxypropane, azetidine, oxetane, tetrahydrofuran ring, tetrahydrothiophene ring, pyrrolidine, piperidine ring, tetrahydropyrane ring, cyclopropyl ring, cyclobutyl ring, cyclopentyl ring, or cyclohexyl ring.

In another preferred example, the epoxypropane, azetidine, oxetane, tetrahydrofuran ring, tetrahydrothiophene ring, pyrrolidine, piperidine ring, tetrahydropyrane ring, cyclopropyl ring, cyclobutyl ring, cyclopentyl ring, cyclohexyl ring are unsubstituted or substituted with 1, 2 or 3 substituents selected from the group consisting of acetyl, hydroxy, hydroxymethyl, hydroxyethyl, carboxyl, $C_{1-3}$ alkyl, $C_{1-3}$ alkoxy, halogenated $C_{1-3}$ alkyl, $C_{3-6}$ cycloalkyl, halogenated $C_{1-3}$ alkoxy, —C(O)OC$_{1-6}$ alkyl, $NR_{a3}R_{b3}$; wherein $R_{a3}$, $R_{b3}$ are each independently hydrogen or $C_{1-3}$ alkyl.

In another preferred example,

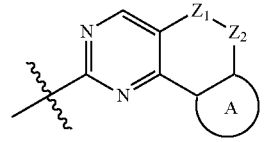

is the structure represented by formula (B-1), formula (B-2), formula (B-3) or formula (B-4):

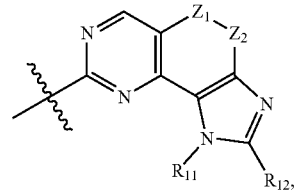

(B-1)

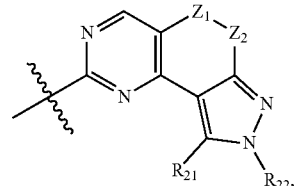

(B-2)

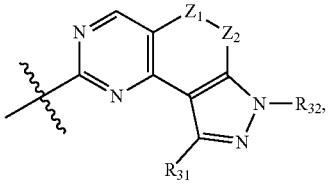

(B-3)

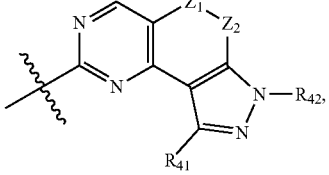

(B-4)

wherein Z, $R_{11}$, $R_{22}$, $R_{32}$, $R_{41}$, $R_{42}$, $R_{21}$, $R_{3}1$, $R_{42}$ are as previously defined.

In another preferred example, $Z_1$ is a bond; $Z_2$ is $CR_{1a}R_{1b}$, $NR_c$, O, S or $S(O)_2$; $R_{1a}$, $R_{1b}$ are defined as $R_a$, $R_b$.

In another preferred example, $Z_1$ is $CR_{1a}R_{1b}$, $NR_c$, O, S or $S(O)_2$; $Z_2$ is $CR_{2a}R_{2b}$ (preferably $CH_2$); $R_{1a}$, $R_{1b}$, $R_{2a}$, $R_{2b}$ are defined as $R_a$, $R_b$.

In another preferred example, $Z_1$ is $CR_{1a}R_{1b}$ (preferably $CH_2$); $Z_2$ is $CR_{2a}R_{2b}$, $NR_c$, O, S or $S(O)_2$; $R_{1a}$, $R_{1b}$, $R_{2a}$, $R_{2b}$ are defined as $R_a$, $R_b$.

In another preferred example, $Z_1$ is a bond; $Z_2$ is $CR_{2a}R_{2b}$, $NR_c$, O, S or $S(O)_2$ ($Z_2$ is preferably $CR_{2a}R_{2b}$, more preferably $CH_2$);

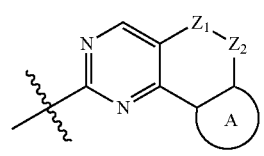

is the structure represented by formula (B-1), formula (B-2) or formula (B-3) (preferably formula (B-2)); $R_{2a}$, $R_{2b}$ are defined as $R_a$, $R_b$.

In another preferred example, $Z_1$ is $CR_{1a}R_{1b}$, $NR_c$, O, S or $S(O)_2$ ($Z_1$ is preferably $CH_2$ or O); $Z_2$ is $CR_{2a}R_{2b}$ ($Z_2$ is preferably $CH_2$);

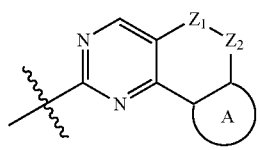

is the structure represented by formula (B-1), formula (B-2) or formula (B-4); $R_{1a}$, $R_{1b}$, $R_{2a}$, $R_{2b}$ are defined as $R_a$, $R_b$.

In another preferred example, $Z_1$ is a bond or O; $Z_2$ is $CR_{2a}R_{2b}$ ($Z_2$ is preferably $CH_2$);

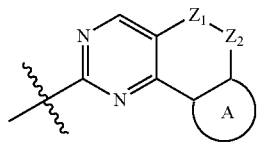

is the structure represented by formula (B-2); $R_{2a}$, $R_{2b}$ are defined as $R_a$, $R_b$.

In another preferred example, $Z_1$ is $CR_{1a}R_{1b}$ ($Z_1$ is preferably $CH_2$); $Z_2$ is $CR_{2a}R_{2b}$ ($Z_2$ is preferably $CH_2$);

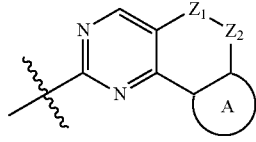

is the structure represented by formula (B-1); $R_{1a}$, $R_{1b}$, $R_{2a}$, $R_{2b}$ are defined as $R_a$, $R_b$.

In another preferred example, $R_1$, $R_3$, $R_4$ are each independently hydrogen, halogen, $C_{1-6}$ alkyl or halogenated $C_{1-6}$ alkyl.

In another preferred example, $R_1$, $R_3$, $R_4$ are each independently hydrogen, fluorine, chlorine, bromine, iodine, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, monochloroethyl, dichloromethyl, 1,2-dichloroethyl, monobromoethyl, monofluoromethyl, difluoromethyl, trifluoromethyl, monofluoroethyl, difluoroethyl, or trifluoroethyl.

In another preferred example, $R_1$, $R_3$, $R_4$ are each independently hydrogen.

In another preferred example, n is 0 or 1.

In another preferred example, the compound is selected from the following Table A:

TABLE A

TABLE A-continued
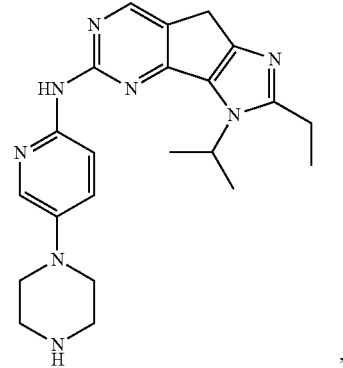 [SMILES: CCc1nc2c(n1C(C)C)-c1nc(Nc3ccc(N4CCNCC4)cn3)ncc1C2]
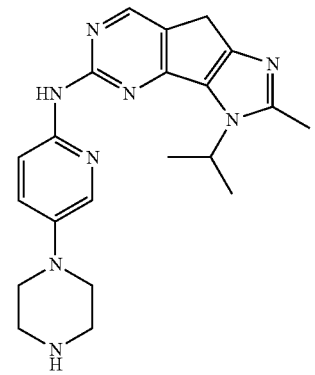
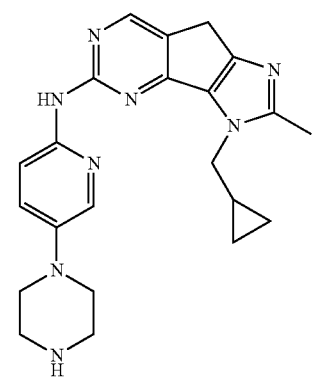
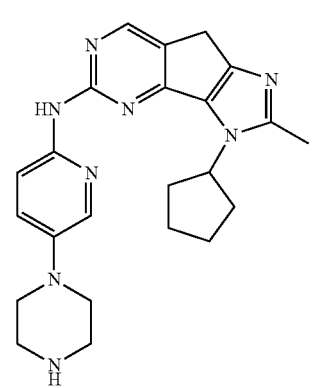
TABLE A-continued
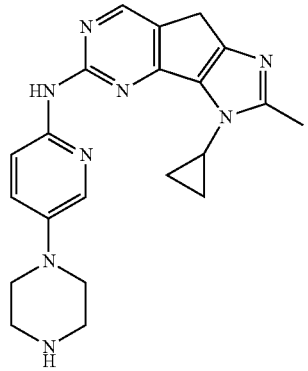
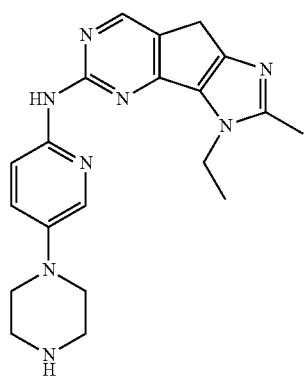
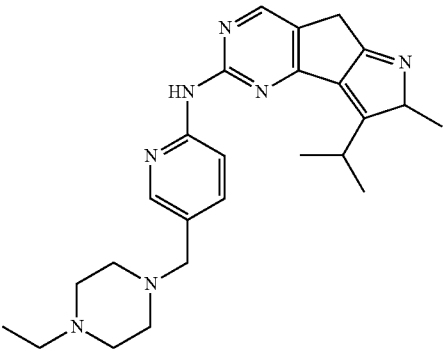
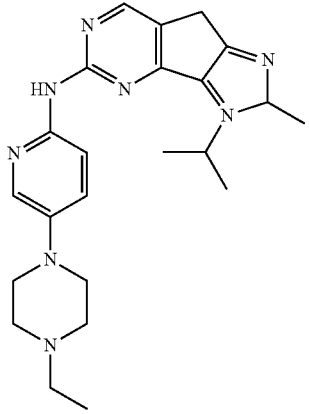

TABLE A-continued
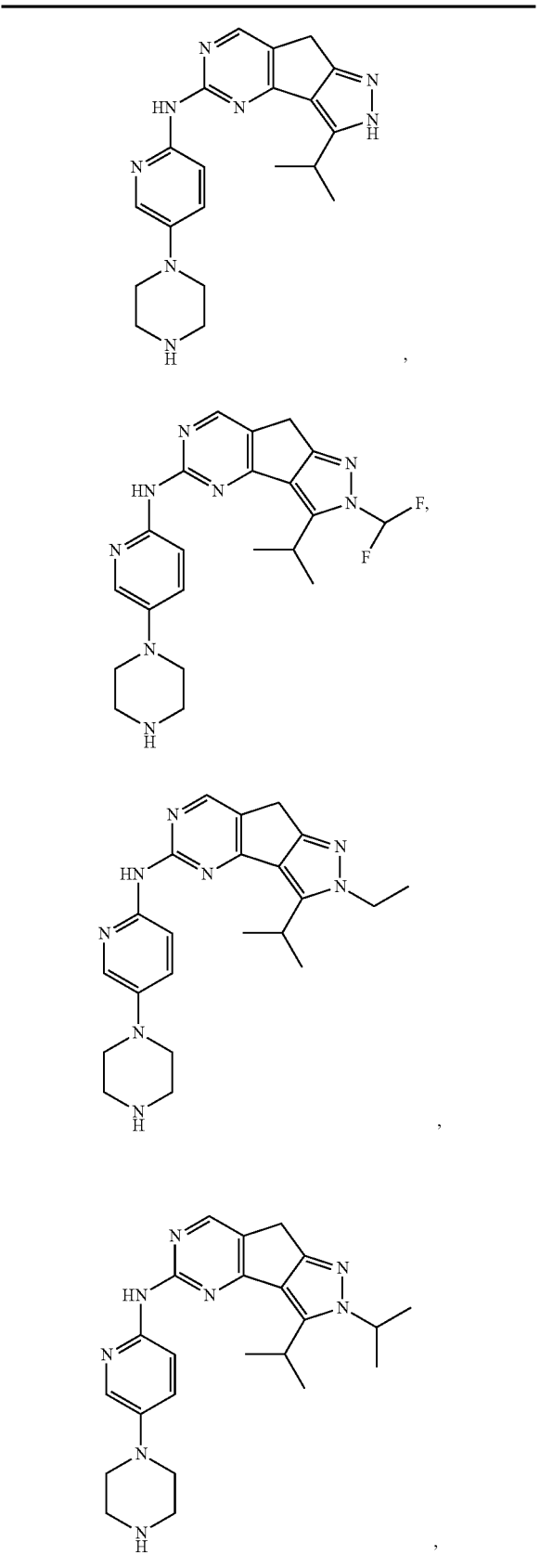
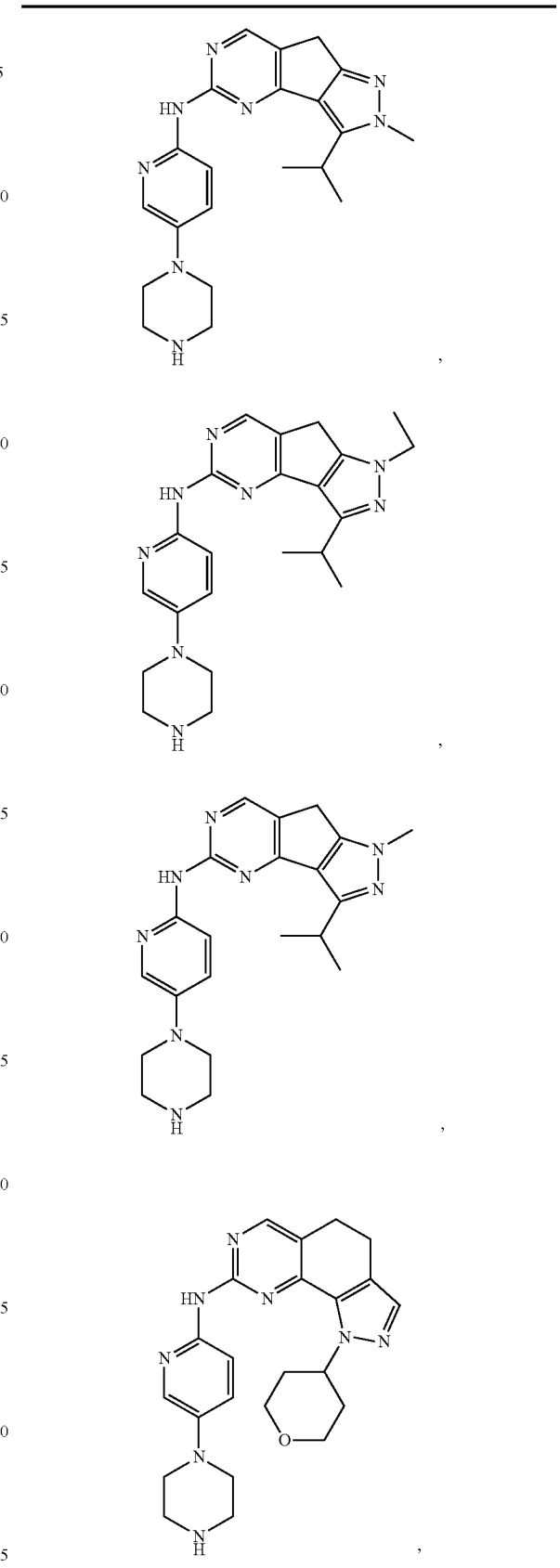

TABLE A-continued
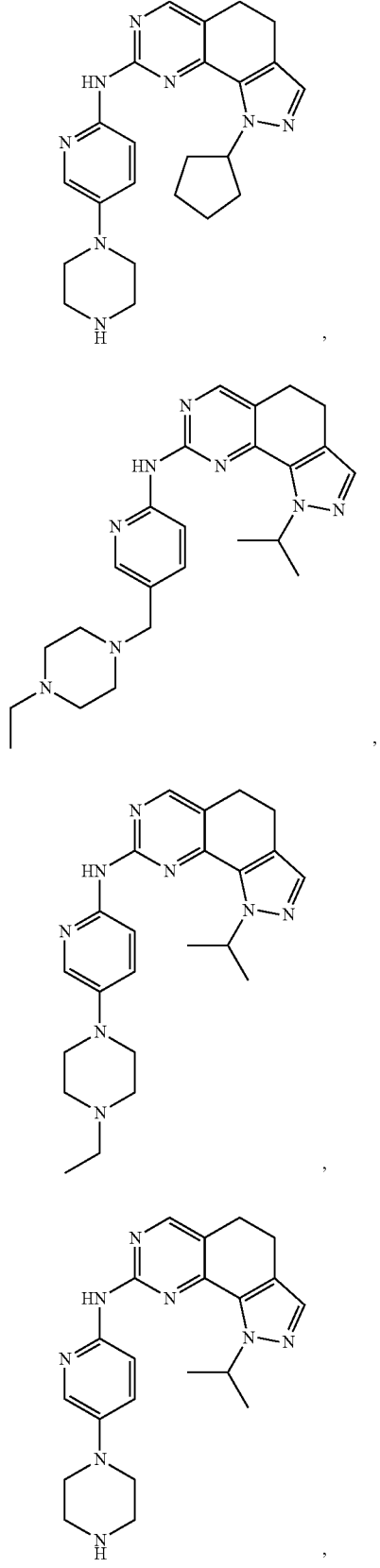
TABLE A-continued
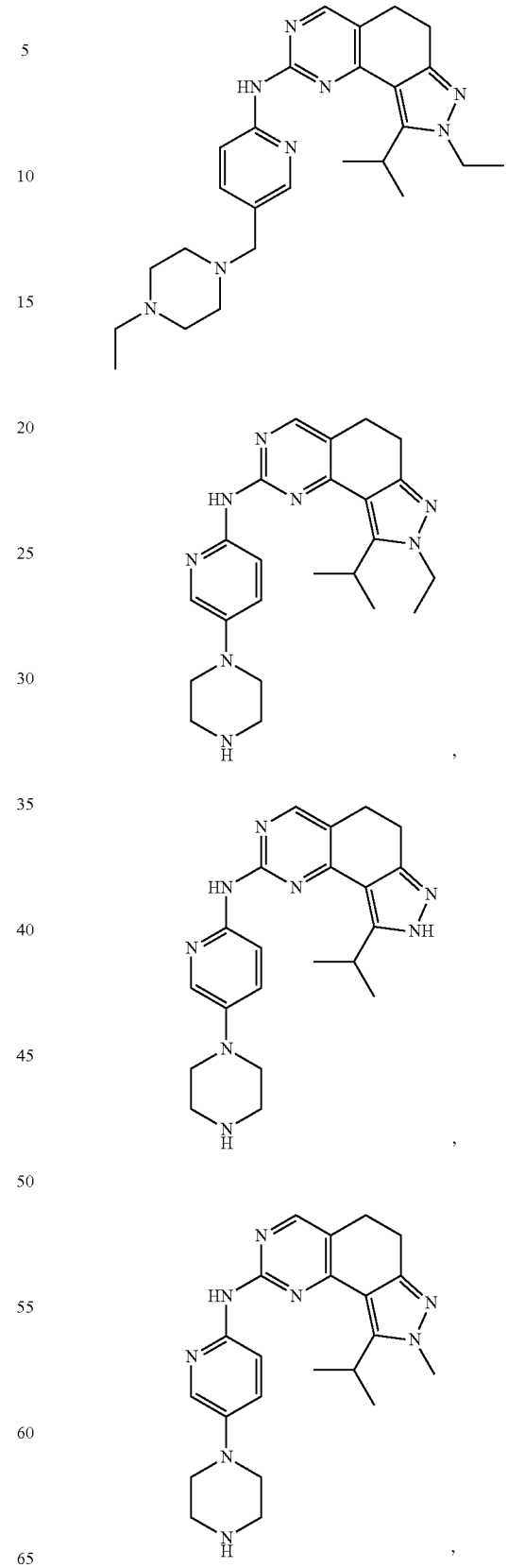

TABLE A-continued
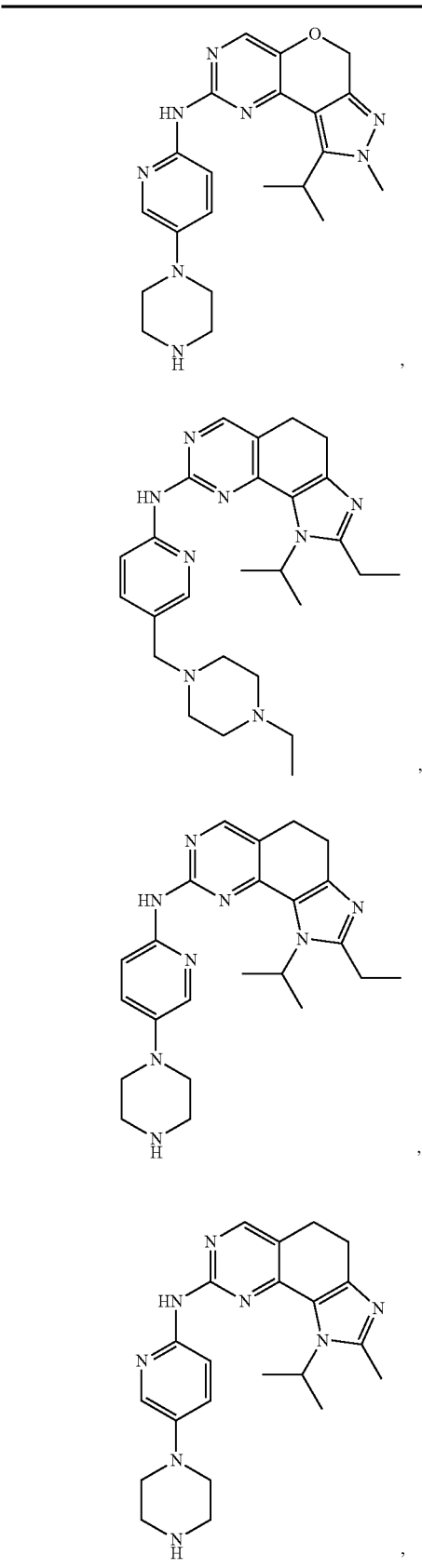
TABLE A-continued
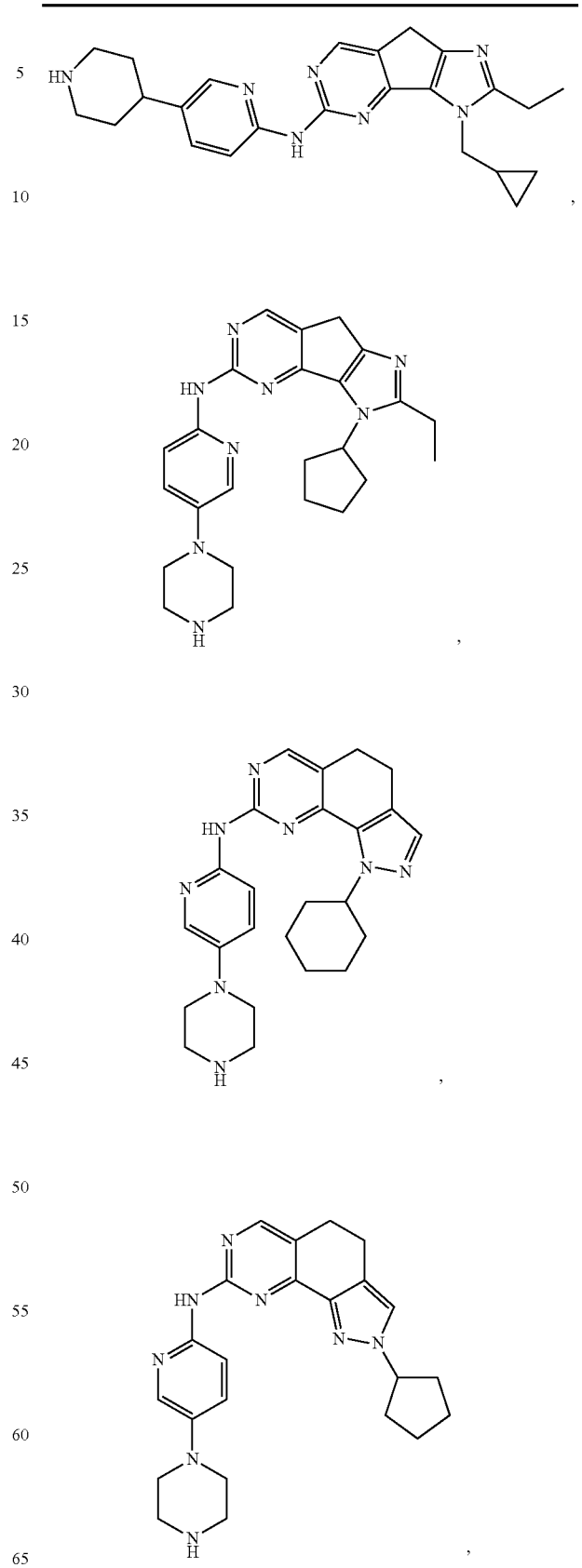

TABLE A-continued
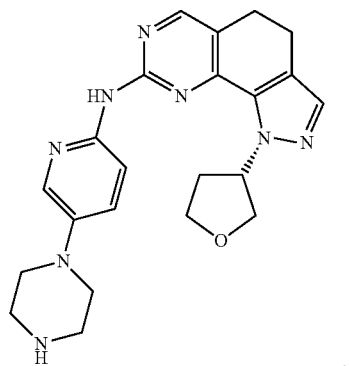
,
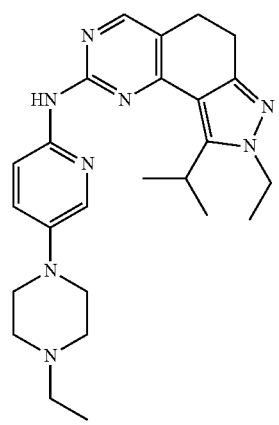
,
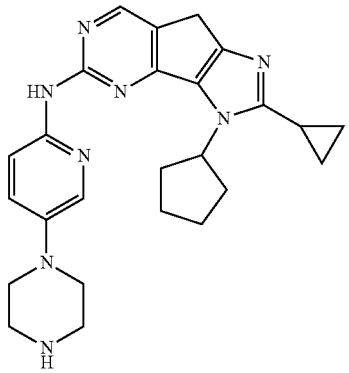
,
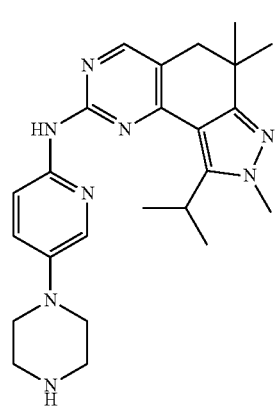
,
In another preferred example, the compound is selected from the following Table B:
TABLE B
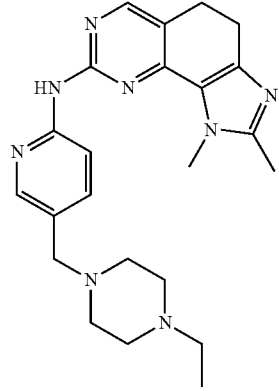
,
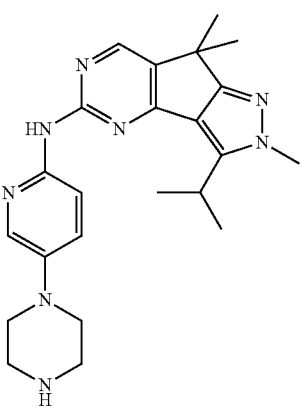
,
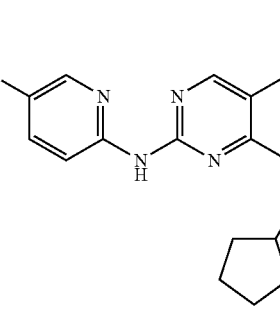
,
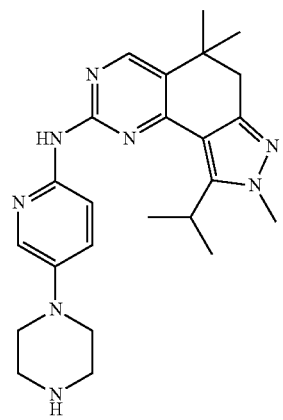
, TABLE B-continued
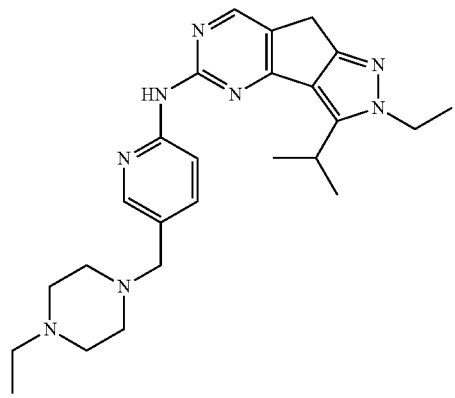
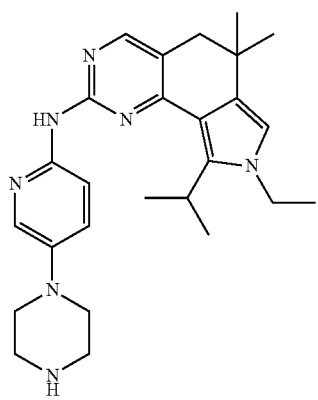
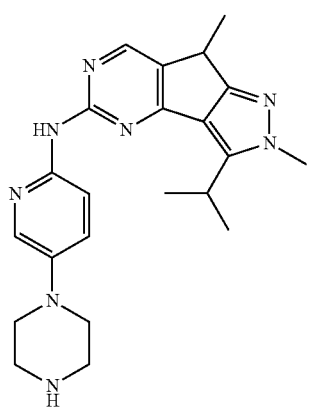
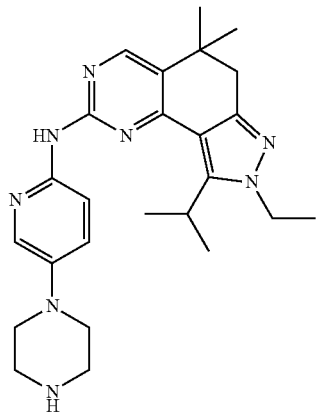
TABLE B-continued
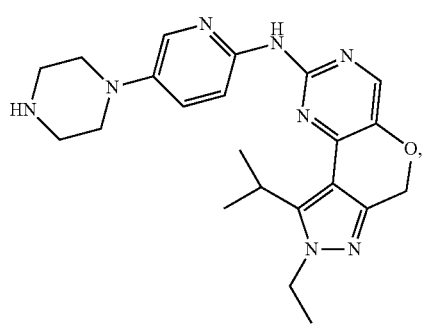 [SMILES: CCn1nc2c(c1C(C)C)-c1nc(Nc3ccc(N4CCNCC4)cn3)ncc1OC2]
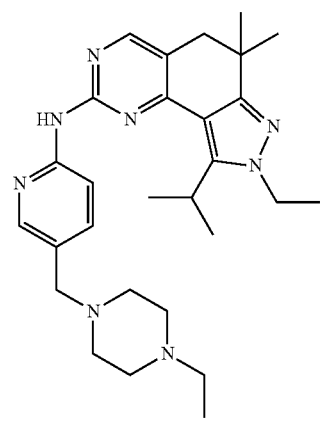
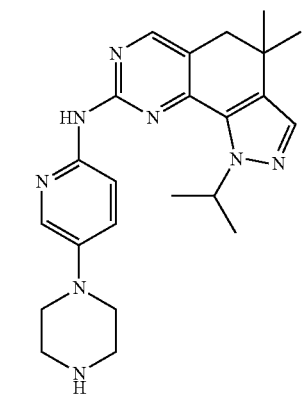
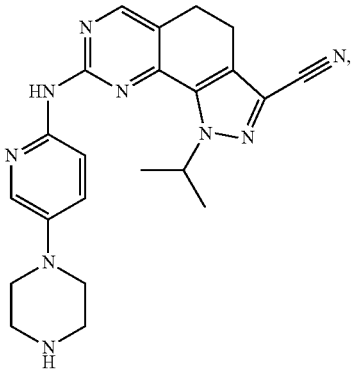 [SMILES: CC(C)n1nc(C#N)c2c1-c1nc(Nc3ccc(N4CCNCC4)cn3)ncc1CC2]

TABLE B-continued
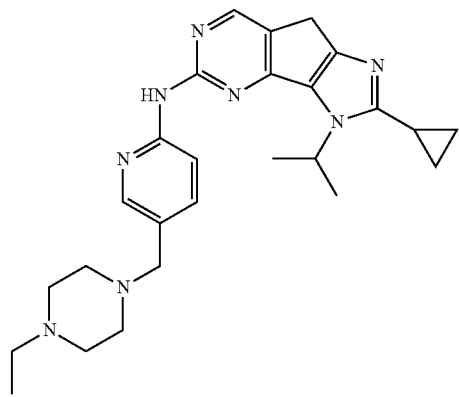
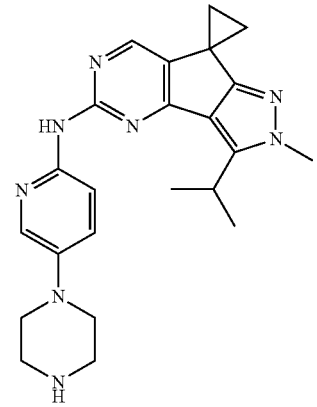
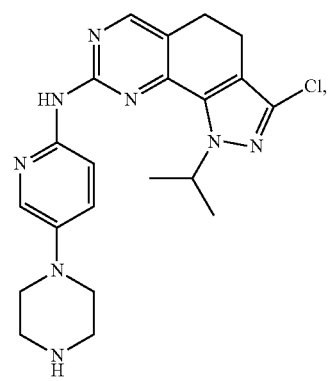 [SMILES: CC(C)n1nc(Cl)c2c1-c1nc(Nc3ccc(N4CCNCC4)cn3)ncc1CC2]
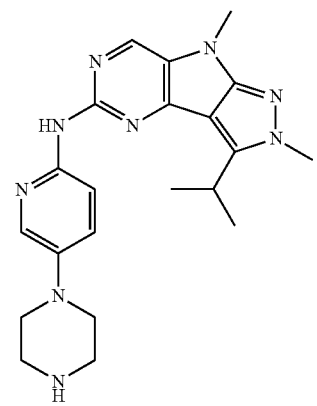
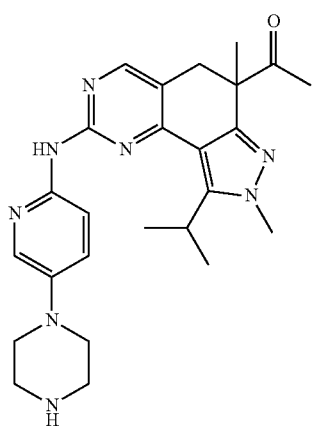
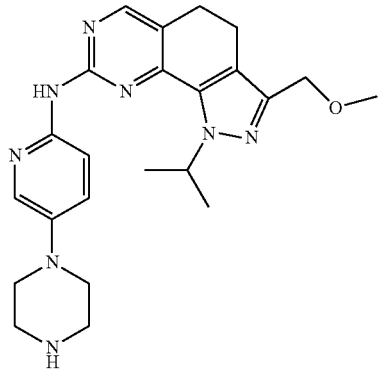
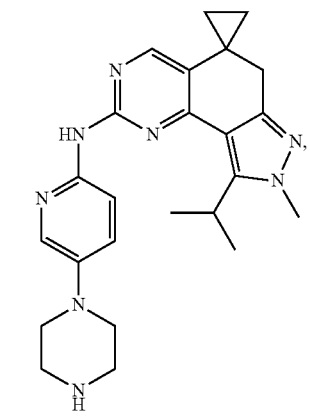 [SMILES: CC(C)c1c2c(nn1C)CC1(CC1)c1cnc(Nc3ccc(N4CCNCC4)cn3)nc1-2]
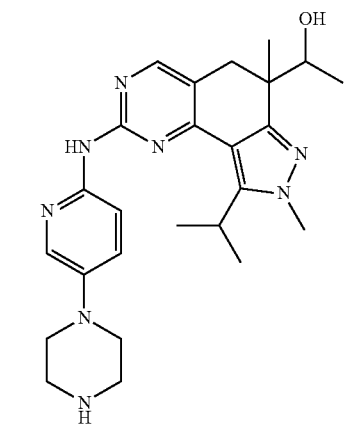

TABLE B-continued

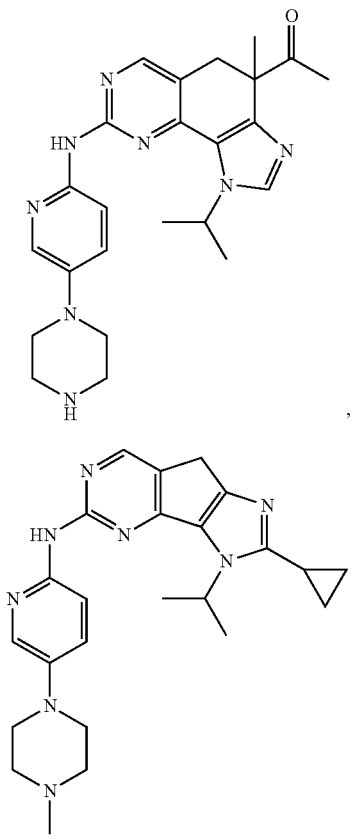

In the second aspect, the resent disclosure provides a pharmaceutical composition comprising the compound of the first aspect of the disclosure, or a pharmaceutically acceptable salt, stereoisomer, solvate or prodrug thereof, and a pharmaceutically acceptable carrier.

In the third aspect, the present disclosure provides use of the compound of the first aspect of the disclosure, or a pharmaceutically acceptable salt, stereoisomer, solvate or prodrug thereof, or the pharmaceutical composition of the second aspect of the disclosure in the preparation of a medicine for the treatment of a disease or disorder, the disease or disorder is selected from the group consisting of cancers, abnormal cell proliferative diseases, infections, inflammatory disorders, autoimmune diseases, cardiovascular diseases, neurodegenerative diseases, hematopoietic toxic diseases caused by radiation, or a combination thereof.

In another preferred example, the cancer is selected from the group consisting of breast cancer, ovarian cancer, prostate cancer, melanoma, brain tumor, esophageal cancer, stomach cancer, liver cancer, pancreatic cancer, colorectal cancer, lung cancer, kidney cancer, skin cancer, glioblastoma, neuroblastoma, sarcoma, liposarcoma, osteochondroma, osteoma, osteosarcoma, spermatocytoma, testiculoma, metrocarcinoma, head and neck tumor, multiple myeloma, malignant lymphoma, polycythemia vera, leukemia, thyroid tumor, ureteral tumor, bladder tumor, gallbladder cancer, cholangiocarcinoma, chorionic epithelioma or pediatric tumor.

In another preferred example, the radiation-induced hematopoietic toxic diseases include, but are not limited to, myelosuppression, neutropenia, leukopenia, and anemia.

In the fourth aspect, the disclosure provides a method of inhibiting CDK4 and/or CDK6 activity, comprising administering to a patient in need thereof a therapeutically effective amount of the compound of the first aspect of the disclosure, or a pharmaceutically acceptable salt, stereoisomer, solvate or prodrug thereof, or the pharmaceutical composition of the second aspect of the disclosure.

In the fifth aspect, the present disclosure provides a method of treating an abnormal cell proliferative disease, an infection (for example, viral infection such as herpe, HIV, fungal infection, etc.), an inflammatory disease (for example, rheumatoid arthritis, osteoarthritis, etc.), an autoimmune disease (such as psoriasis, lupus, type I diabete, diabetic nephropathy, multiple sclerosis, glomerulonephritis, etc.), a cardiovascular disease (such as myocardial infarction, stroke, atherosclerosis, postoperative vascular stenosis, restenosis, etc.) or a neurodegenerative disease (such as Alzheimer's disease, Parkinson's disease, etc.), comprising administering to a patient in need thereof a therapeutically effective amount of the compound of the first aspect of the disclosure, or a pharmaceutically acceptable salt, stereoisomer, solvate or prodrug thereof, or the pharmaceutical composition of the second aspect of the disclosure, wherein the abnormal cell proliferative disease may be cancer.

In the sixth aspect, the present disclosure provides a method of treating cancer, comprising administering to a patient in need thereof a therapeutically effective amount of the compound of the first aspect of the present disclosure, or a pharmaceutically acceptable salt, stereoisomer, solvate or prodrug thereof, or the pharmaceutical composition of the second aspect of the present disclosure, wherein the cancer is selected from the group consisting of breast cancer, ovarian cancer, prostate cancer, melanoma, brain tumor (e.g. gliomas with malignant astroglial and oligodendroglioma components, etc.), esophageal cancer, stomach cancer, liver cancer, pancreatic cancer, colorectal cancer (e.g., colon cancer, rectal cancer, etc.), lung cancer (e.g., non-small cell lung cancer, small cell lung cancer, primary or metastatic squamous carcinoma, etc.), kidney cancer, skin cancer, glioblastoma, neuroblastoma, sarcoma, liposarcoma, osteochondroma, osteoma, osteosarcoma, seminoma, testicular tumor, uterine cancer (for example, cervical cancer, endometrial cancer, etc.), head and neck tumors (such as maxillary cancer, laryngeal cancer, pharynx cancer, tongue cancer, intraoral cancer, etc.), multiple myeloma, malignant lymphoma (such as reticulocyte sarcoma, lymphoid sarcoma, Hodgkin's lymphoma, mantle cell lymphoma, etc.), polycythemia vera, leukemia (e.g., acute myeloblastic leukemia, chronic granulocytic leukemia, acute lymphoblastic leukemia, chronic lymphocytic leukemia, etc.), thyroid tumor, ureteral tumor, bladder tumor, gallbladder cancer, cholangiocarcinoma, chorionic epithelial carcinoma or paediatric tumor (e.g., Ewing familial sarcoma, Wilms sarcoma, rhabdomyosarcoma, hemangiosarcoma, embryonic testicular cancer, neuroblastoma, retinoblastoma, hepatoblastoma, nephroblastoma, etc.).

It should be understood that each of the above technical features of the present disclosure and each technical feature specifically described below (such as in Examples) can be combined with each other within the scope of the present disclosure so as to constitute new or preferred technical solutions which need not be specified again herein.

DETAILED DESCRIPTION OF THE INVENTION

The inventors have conducted extensive and intensive studies and have unexpectedly found that the pyridylamino substituted heterotricyclic structures of the present disclosure have a high inhibitory activity against CDK4 and CDK6, and have weaker inhibitory activities against CDK1 and CDK2, and therefore have an obvious 4/6 selectivity. Hence, this series of compounds of the present disclosure are hopefully developed as a selective CDK4 and CDK6 inhibitor for the treatment of cancer. Based on this, the inventors completed the present invention.

Definition of Terms

As used herein, "alkyl" refers to straight and branched saturated aliphatic hydrocarbon groups, $C_{1-8}$ alkyl is an alkyl containing 1 to 8 carbon atoms, preferably $C_{1-6}$ alkyl, more preferably $C_{1-3}$ alkyl with similar definitions; non-limiting examples of the alkyl include: methyl, ethyl, n-propyl, isopropyl, n-butyl, isobutyl, tert-butyl, sec-butyl, n-pentane, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and their various branched isomers.

As used herein, "cycloalkyl" refers to a saturated or partially unsaturated monocyclic cyclic hydrocarbon group, "$C_{3-8}$ cycloalkyl" refers to a cyclic hydrocarbon group containing 3 to 8 carbon atoms, preferably a $C_{3-6}$ cycloalkyl with similar definition; non-limiting examples of cycloalkyl include cyclopropyl, cyclobutyl, cyclopentyl, cyclopentenyl, cyclohexyl, cyclohexenyl, cyclohexadienyl, cycloheptyl, cycloheptatrienyl. cyclooctyl and the like, preferably cyclopropyl, cyclopentyl, cyclohexenyl.

As used herein, "spiro" refers to a polycyclic group in which two single sings share one carbon atom (spiro atom), wherein these polycyclic groups may contain one or more double bonds, but none of the rings has a completely conjugated π electron system. According to the number of rings therein, the spiros are divided into bicyclic spiros or polycyclic spiros, wherein the bicyclic spiros are preferable. And 4 membered/5 membered, 5 membered/5 membered, or 5 membered/6 membered bicyclic spiros are more preferable. For example:

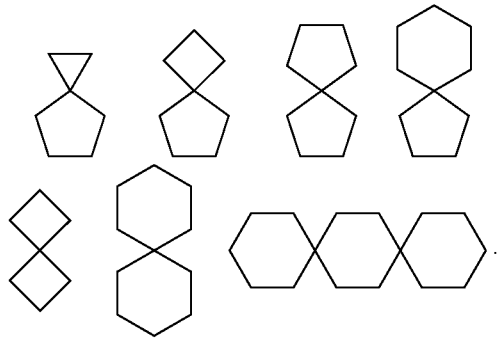

As used herein, "spiroheterocycle" refers to a polycyclic hydrocarbon in which two single rings share one atom (spiro atom), wherein one or two ring atoms are selected from heteroatoms such as nitrogen, oxygen, or $S(O)_n$ (wherein n is an integer from 0 to 2), the remaining ring atoms are carbon atoms. These spiroheterocycles may contain one or more double bonds, but none of the rings has a completely conjugated π-electron system. According to the number of rings, the spiroheterocycles are divided into bicyclic spiroheterocycles or polycyclic spiroheterocycles, wherein bicyclic spiroheterocycles are preferable. And 4 membered/5 membered, 5 membered/5 membered, or 5 membered/6 membered bicyclic spiroheterocycles are more preferable. For example:

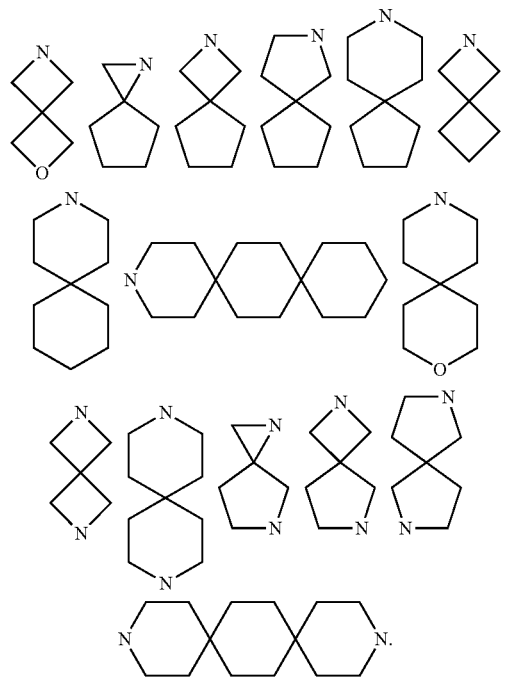

As used herein, "bridged ring" refers to a group containing multiple rings which share two or more carbon atoms. The shared carbon atoms are known as bridgehead carbons. Between two bridgehead carbons there may be a carbon chain or a bond, which is called a bridge. These bridged rings may contain one or more double bonds, but none of the rings has a completely conjugated it-electron system. Bicyclic or tricyclic bridged rings are preferred. For example:

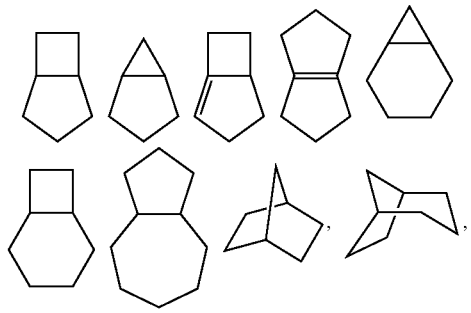

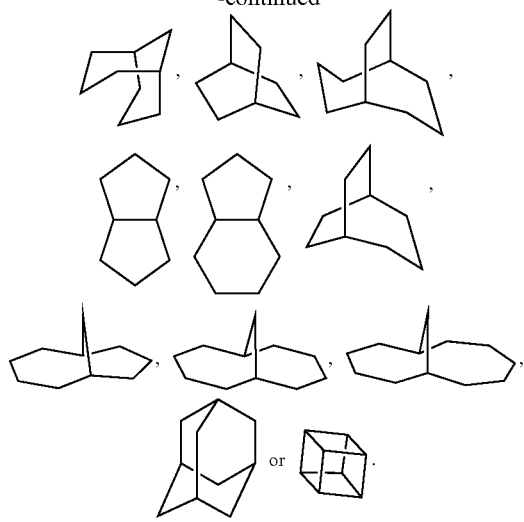

As used herein, "bridged heterocycle" refers to a group containing multiple rings which share two or more atoms and have one or more ring atoms selected from heteroatoms such as nitrogen, oxygen, or $S(O)_n$ (wherein n is an integer from 0 to 2) and the remaining ring atoms being carbon atoms. These bridged heterocycles may contain one or more double bonds, but none of the rings has a completely conjugated π-electron system. Bicyclic or tricyclic bridged heterocycles are preferred. For example:

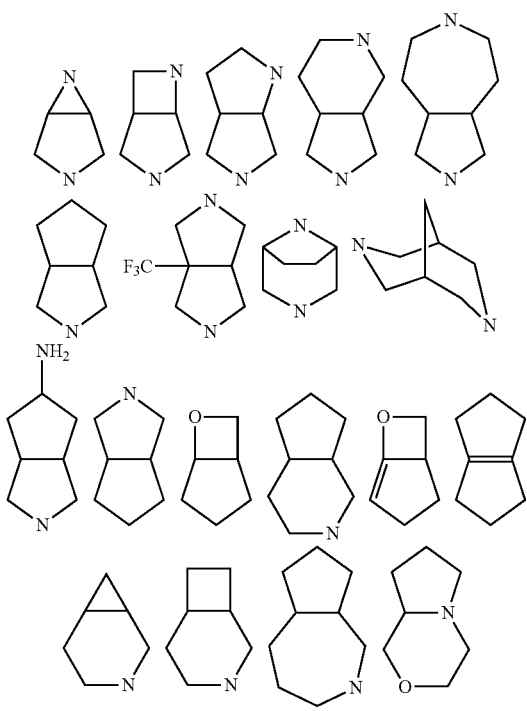

As used herein, "8 to 10 membered bicyclic ring" refers to a two-ring-containing bridged ring having 8 to 10 ring atoms. The bicyclic ring may be a saturated full-carbon bicyclic or partially unsaturated full-carbon bicyclic ring. Examples of bicyclic ring include (but not limited to):

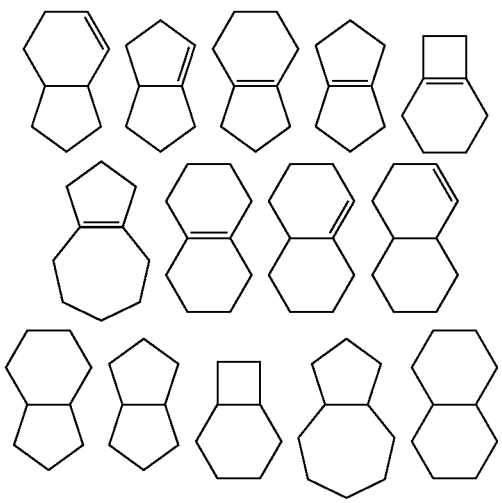

As used herein, "8 to 10 membered bis-heterocycle" refers to a two-ring-containing bridged heterocycle having 8 to 10 ring atoms, wherein 1, 2, 3, 4 or 5 carbon ring atoms are replaced by heteroatoms selected from nitrogen, oxygen or sulfur. Examples of 8 to 10 membered bis-heterocycles include, but are not limited to, tetrahydroquinoline ring, tetrahydroisoquinoline ring, decahydroquinoline ring, and the like.

As used herein, "$C_{1-8}$ alkoxy" refers to —O—($C_{1-8}$ alkyl), wherein the alkyl is as defined above. $C_{1-6}$ alkoxy is preferred, and $C_{1-3}$ alkoxy is more preferred. Non-limiting examples include methoxy, ethoxy, propoxy, isopropoxy, butoxy, tert-butoxy, isobutoxy, pentoxy, and the like.

As used herein, "$C_{3-8}$ cycloalkoxy" refers to —O—($C_{3-8}$ cycloalkyl), wherein the cycloalkyl is as defined above. $C_{3-6}$ cycloalkoxy is preferred. Non-limiting examples include cyclopropyloxy, cyclobutyloxy, cyclopentoxy, cyclohexyloxy, etc.

As used herein, "$C_{6-10}$ aryl" refers to a full-carbon monocyclic or fused polycyclic (ie, ring that shares an adjacent pair of carbon atoms) group having a conjugated π-electron system, and refers to an aryl containing 6 to 10 carbon atoms; phenyl and naphthyl are preferred, and phenyl is more preferred.

As used herein, "a bond" means that two groups connected thereby are connected by a covalent bond.

As used herein, "halogen" refers to fluorine, chlorine, bromine, or iodine.

As used herein, "halogenated" means that one or more (e.g., 1, 2, 3, 4 or 5) hydrogens in a group are substituted by halogen(s).

For example, "halogenated $C_{1-8}$ alkyl" means that the alkyl is substituted with one or more (e.g., 1, 2, 3, 4 or 5) halogens, wherein the alkyl is as defined above. Halogenated $C_{1-6}$ alkyl is preferred, and halogenated $C_{1-3}$ alkyl is more preferred. Examples of halogenated $C_{1-8}$ alkyl include, but not limited to, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, and the like.

For another example, "halogenated $C_{1-8}$ alkoxy" means that the alkoxy is substituted with one or more (e.g., 1, 2, 3, 4 or 5) halogens, wherein the alkoxy is as defined above. Halogenated $C_{1-6}$ alkoxy is preferred, and halogenated $C_{1-3}$ alkoxy is more preferred. Examples of the halogenated $C_{1-8}$ alkoxy include, but are not limited to, trifluoromethoxy, trifluoroethoxy, monofluoromethoxy, monofluoroethoxy, difluoromethoxy, difluoroethoxy, and the like.

For another example, "halogenated $C_{3-8}$ cycloalkyl" means that a cycloalkyl is substituted with one or more (e.g., 1, 2, 3, 4 or 5) halogens, wherein the cycloalkyl is as defined above. Halogenated $C_{3-6}$ cycloalkyl is preferred. Examples include, but are not limited to, trifluorocyclopropyl, monofluorocyclopropyl, monofluorocyclohexyl, difluorocyclopropyl, difluorocyclohexyl and the like.

As used herein, "deuterated $C_{1-8}$ alkyl" means that an alkyl is substituted with one or more (e.g., 1, 2, 3, 4, or 5) deuterium atoms, wherein the alkyl is as defined above. Deuterated $C_{1-6}$ alkyl is preferred, and deuterated $C_{1-3}$ alkyl is more preferred. Examples of the deuterated $C_{1-20}$ alkyl include, but not limited to, monodeuterated methyl, monodeuterated ethyl, dideuterated methyl, dideuterated ethyl, trideuterated methyl, trideuterated ethyl and the like.

As used herein, "amino" refers to $NH_2$, "cyano" refers to CN, "nitro" refers to $NO_2$, "benzyl" refers to —$CH_2$-phenyl, "oxo" refers to =O, "carboxyl" refers to —C(O)OH, "acetyl" refers to —C(O)$CH_3$, "hydroxymethyl" refers to —$CH_2OH$, "hydroxyethyl" refers to —$CH_2CH_2OH$, "hydroxy" refers to —OH, "thiol" refers to SH, the structure of "cyclopropylidene" is:

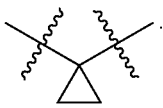

As used herein, "heteroaryl ring" and "heteroaryl" can be used interchangeably, and refer to having 5-10 carbon atoms, wherein 5 or 6 membered monocyclic heteroaryls or 8 to 10 membered bicyclic heteroaryls are preferred; 6, 10 or 14 π electrons are shared in the ring array; and other than carbon atoms, the heteroaryl also has 1 to 5 heteroatoms. "Heteroatom" refers to nitrogen, oxygen or sulfur.

As used herein, "3 to 6 membered saturated or partially unsaturated monocyclic ring" refers to a saturated or partially unsaturated full-carbon monocyclic ring containing 3 to 6 ring atoms. Examples of monocyclic rings include, but not limited to, cyclopropyl ring, cyclobutyl ring, cyclopentyl ring, cyclopentenyl ring, cyclohexyl ring, cyclohexenyl ring, cyclohexadienyl ring, cycloheptyl ring, cycloheptatrienyl ring, cyclooctyl ring and the like.

As used herein, "3 to 6 membered saturated single heterocycle" means a 3 to 6 membered monocycle in which 1, 2 or 3 carbon atoms are substituted by heteroatom(s) selected from nitrogen, oxygen, or $S(O)_t$ (wherein t is an integer from 0 to 2), but which does not include a ring portion of —O—O—, —O—S— or —S—S—, and the remaining ring atoms of which are carbons; 4 to 6 membered is preferred, and 5 to 6 membered is more preferred. Examples of saturated single heterocycles include, but not limited to, epoxypropane, azetidine, oxetane, tetrahydrofuran, tetrahydrothiophene, pyrrolidine, piperidine, pyrroline, oxazolidine, piperazine, dioxolane, dioxane, morpholine, thiomorpholine, thiomorpholine-1,1-dioxide, tetrahydropyran and the like.

As used herein, "5 to 6 membered monocyclic heteroaryl ring" refers to a monocyclic heteroaryl ring containing 5 to 6 ring atoms, examples include but not limited to, thiophene ring, N-alkylpyrrole ring, furan ring, thiazole ring, imidazole ring, oxazole ring, pyrrole ring, pyrazole ring, triazole ring, tetrazole ring, isoxazole ring, oxadiazole ring, thiadiazole ring, pyridine ring, pyridazine ring, pyrimidine ring, pyrazine ring and the like.

As used herein, "8 to 10 membered bicyclic heteroaryl ring" refers to a bicyclic heteroaryl ring containing 8 to 10 ring atoms, including, for example, but not limited to, benzofuran, benzothiophene, indole, isoindole, quinoline, isoquinoline, indazole, benzothiazole, benzimidazole, quinazoline, quinoxaline, cinnoline, phthalizine.

As used herein, "substituted" means that one or more hydrogen atoms, preferably 1-5 hydrogen atoms in a group are independently substituted by a corresponding number of substituents, and more preferably 1 to 3 hydrogen atoms are independently substituted by a corresponding number of substituents. It goes without saying that the substituents are only located in their possible chemical positions, and those skilled in the art can determine (by experiment or theory) the possible or impossible substitutions without undue effort. For example, an amino or hydroxy with a free hydrogen may be unstable when combined with a carbon atom having an unsaturated (eg olefinic) bond.

As used herein, any one of the groups described herein may be substituted or unsubstituted.

When the above groups are substituted, the substituents are preferably 1 to 5 groups independently selected from the group consisting of CN, halogen, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), halogenated $C_{1-8}$ alkoxy (preferably halogenated $C_{1-6}$ alkoxy, more preferably halogenated $C_{1-3}$ alkoxy), amino substituted with $C_{1-8}$ alkyl, amino, amino substituted with halogenated $C_{1-8}$ alkyl, 4 to 6 membered saturated single heterocycle, 5 to 6 membered monocyclic heteroaryl ring, 8 to 10 membered bicyclic heteroaryl ring, spiro, spiroheterocycle, bridged ring or bridged heterocycle.

The above-mentioned various substituents themselves of the present disclosure can also be substituted with the groups described herein.

When 4 to 6 membered saturated single heterocycles described herein are substituted, the positions of the substituents may be at their possible chemical positions, and representative substitutions of the exemplary single heterocycles are shown below:

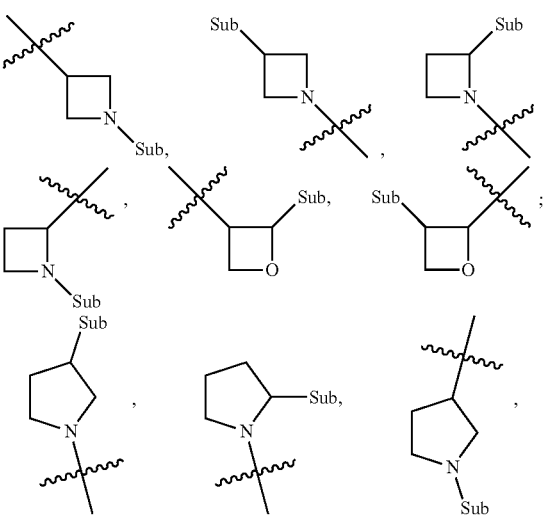

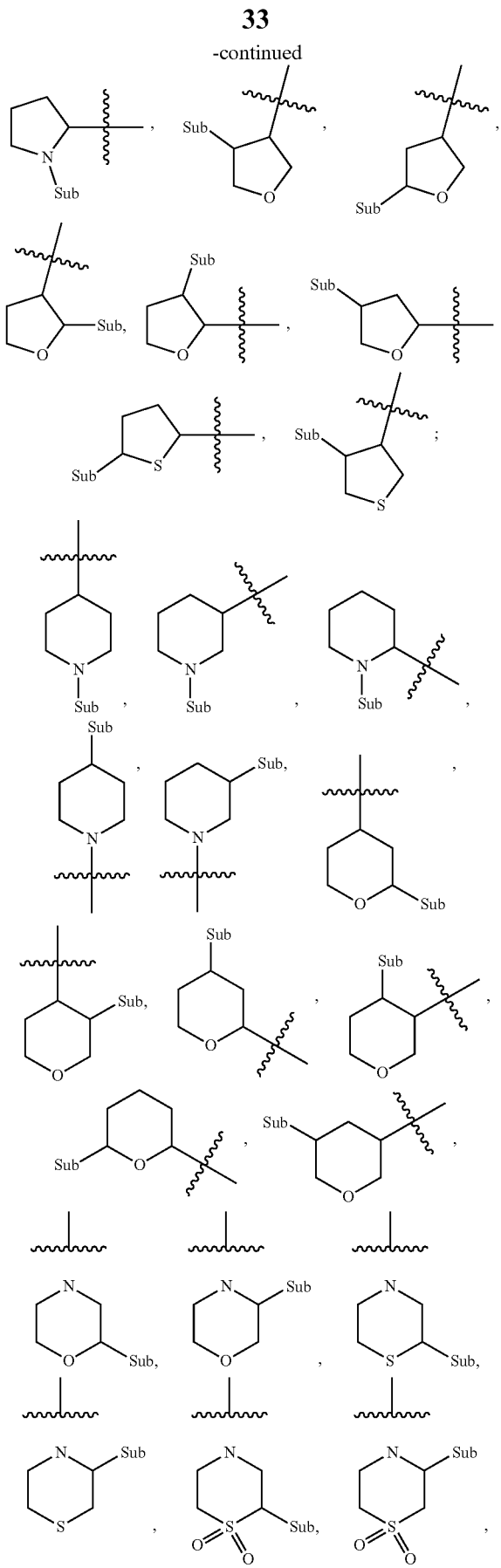

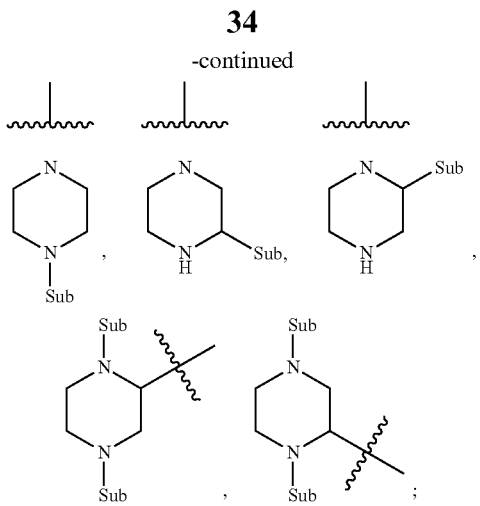

wherein "Sub" represents the various types of substituents described herein; "〰" represents connections with other atoms.

As used herein, "therapeutically effective amount" refers to an amount of the compound of the present disclosure that will elicit the biological or medical response of an individual, for example, reduction or inhibition of an enzyme or a protein activity, or amelioration of a symptom, alleviation of a condition, slow or delay disease progression, or prevention of a disease, etc.

As used herein, "pharmaceutically acceptable carrier" refers to a non-toxic, inert, solid, semi-solid substance or liquid filler, diluent, encapsulating material or auxiliary formulation or any type of excipient that is compatible with the patient which is preferably a mammal and more preferably a human. It is suitable for delivering active agent to a target without stopping the activity of the agent.

As used herein, "patient" refers to an animal, preferably a mammal, and more preferably a human being. The term "mammal" refers to a warm-blooded vertebrate mammal, including, for example, cat, dog, rabbit, bear, fox, wolf, monkey, deer, rat, pig and human.

As used herein, "treating/treatment" refers to alleviating, delaying progression, attenuating, preventing, or maintaining an existing disease or disorder (e.g., cancer). Treating/treatment also includes curing one or more symptoms of the disease or disorder, preventing its development or reducing to some extent.

PREPARATION METHOD

The present disclosure provides the preparation method of compounds of formula (I), the compounds of the present disclosure can be prepared by a variety of synthetic operations, exemplary preparation methods of these compounds may include (but not limited to) the processes described below.

Preferably, the compounds of formula (I) can be prepared through the following schemes and exemplary methods described in embodiment, as well as according to the related publications available for those skilled in the art.

The steps of the method can be expanded or combined as desired in practice.

Scheme 1:

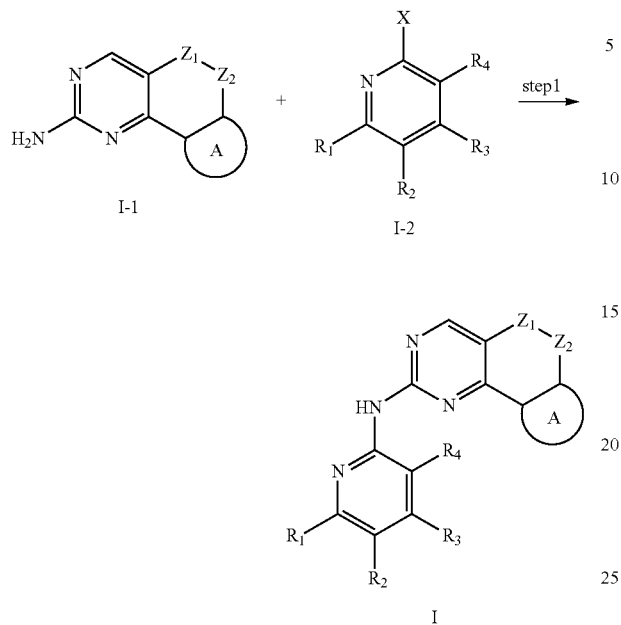

A compound of formula (I) is obtained by carbon-nitrogen coupling reaction between formula (I-1) and formula (I-2). The carbon-nitrogen coupling of arylamines and aryl halides can be performed under Pd catalyst, suitable ligand and base conditions, preferably potassium tert-butoxide or sodium tert-butoxide, and PdO-catalyzed coupling, for example, Buchwald-Hartwig reaction, to give the final compounds of formula (I). Starting materials of compounds of formula (I-1) and formula (I-2) can be commercially available or prepared by methods known to those skilled in the art according to their specific different structures.

The compound of formula (I-1) can be prepared by a method comprising the following steps:

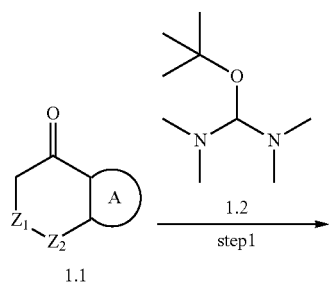

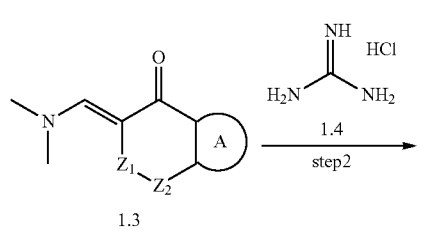

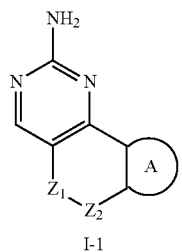

The compounds of formula (1.1) and formula (1.2) are reacted under heating to give compounds of formula (1.3). The compounds of formula (1.3) and formula (1.4) are cyclized under basic conditions to give the compounds of formula (I-1).

Intermediate compounds of formula (1.1) can be obtained by two different routes. In scheme 1 of the synthetic route, the compounds of formula (1.1) can be prepared by method 1 comprising the following steps:

Method 1

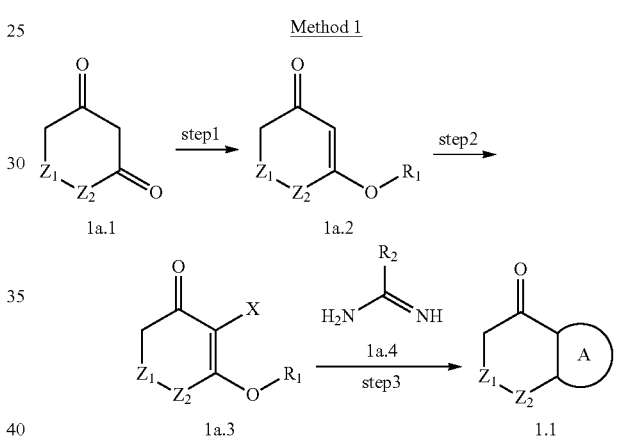

The compounds of formula (1a.1) can be reacted with corresponding alcohols to give the compounds of formula (1a.2). The compounds of formula (1a.2) may be reacted by a halogenating agent such as N-halogenated succinimide in a suitable solution such as dichloromethane to give the compounds of formula (1a.3), and the compounds of formula (1a.3) can be reacted with amidine under basic conditions to give the compounds of formula (1a.5). The compounds of formula (1.1) may be modified, for example by nucleophilic substitution, alkylation reaction, etc.

In the second scheme of the synthetic route, the compounds of formula (1.1) can be prepared by method 2 comprising the following steps:

Method 2

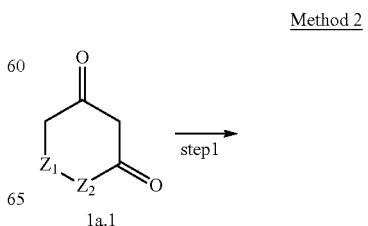

-continued

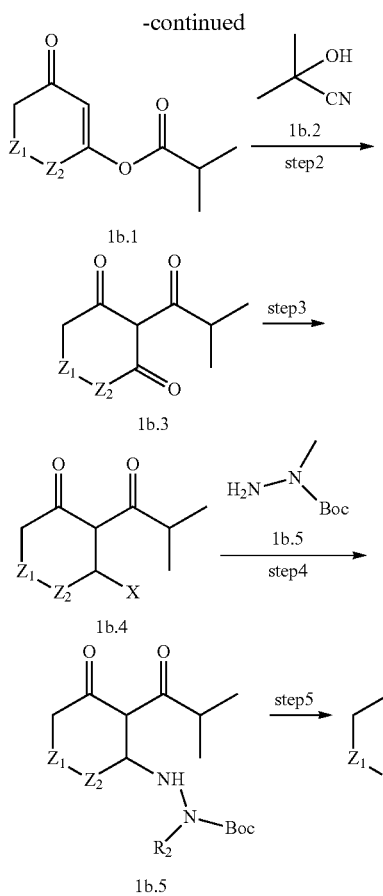

The compounds of formula (1a.1) may be reacted with an acylate such as acyl chloride to give an ester, i.e., the compound of formula (1b.1), and the compounds of formula (1b.1) may be reacted with the compounds of formula (1b.2) under basic conditions to obtain the compounds of formula (1b.3), the compounds of formula (1b.3) may be halogenated using halogenating reagents such as thionyl chloride, phosphorus oxychloride, phosphorus pentachloride, oxalyl chloride, etc. preferably oxalyl chloride, to give the compounds of formula (1b.4), the compounds of formulae (1b.4) and (1b.5) may undergo substitution reactions under basic conditions to give compounds of formula (1b.6), the compounds of formula (1b.6) may be deprotected under acidic conditions, and cyclized to get the compounds of formula (1.1).

The reactions in the above steps are all conventional reactions known to those skilled in the art. Unless otherwise specified, the reagents and raw material compounds used in the synthetic route are all commercially available, or can be prepared by those skilled in the art by referring to known methods according to the different compound structures designed.

Compared with the prior art, the main advantages of the present disclosure are to provide a series of novel pyridylamino substituted heterotricyclic compounds which have a high selective inhibitory activity on CDK4/6, in addition also have good brain permeability and can be used as drugs for the treatment of a wide range of cancers.

The present invention will be further illustrated below with reference to the specific examples. It should be understood that these examples are only to illustrate the invention but not to limit the scope of the invention. The experimental methods without specific conditions in the following embodiments are generally carried out according to conventional conditions, or in accordance with the conditions recommended by the manufacturer. Unless indicated otherwise, parts and percentage are calculated by weight. Unless otherwise defined, terms used herein are of the same meanings that are familiar to those skilled in the art. In addition, any methods and materials similar or equivalent to those described herein can be applied to the present invention.

As used herein, DMB refers to 2,4-dimethoxybenzyl, THF refers to tetrahydrofuran, EA refers to ethyl acetate, PE refers to petroleum ether, $Ac_2O$ refers to acetic anhydride, NBS refers to N-bromosuccinimide, DCM refers to dichloromethane, AIBN refers to azodiisobutyronitrile, $Pd(dppf)Cl_2$ refers to [1,1'-bis(diphenylphosphino)ferrocene]palladium dichloride, TFA refers to trifluoroacetic acid, TBSCl refers to tert-butyldimethylchlorosilane, NCS refers to N-chlorosuccinimide, DHP refers to dihydrogenpyran, $LiAlH_4$ refers to lithium aluminium hydride, PMB refers to p-methoxybenzyl, LiHMDS refers to lithium bistrimethylsilylamide, $Pd_2(dba)_3$ refers to tris(dibenzylideneacetone)dipalladium, RuPhos refers to 2-dicyclohexylphosphoryl-2',6'-diisopropoxy-1,1'-biphenyl, DMAP refers to 4-dimethylaminopyridine, THP refers to tetrahydropyran, n-BuLi refers to n-butyllithium, TMsOTf refers to trimethylsilyl trifluoromethanesulfonate, TEBAC refers to triethylbenzylammonium chloride, HATU refers to 2-(7-azobenzotriazole)-N,N,N',N'-tetramethyluronium hexafluorophosphate, DMF refers to dimethylformamide, DMSO refers to dimethylsulfoxide, DIEA refers to N,N-diisopropylethylamine, BINAP refers to (2R,3S)-2,2'-bis diphenylphosphino-1,1'-binaphthyl.

As used herein, room temperature refers to about 20-25° C.

Preparation of Intermediate 1a

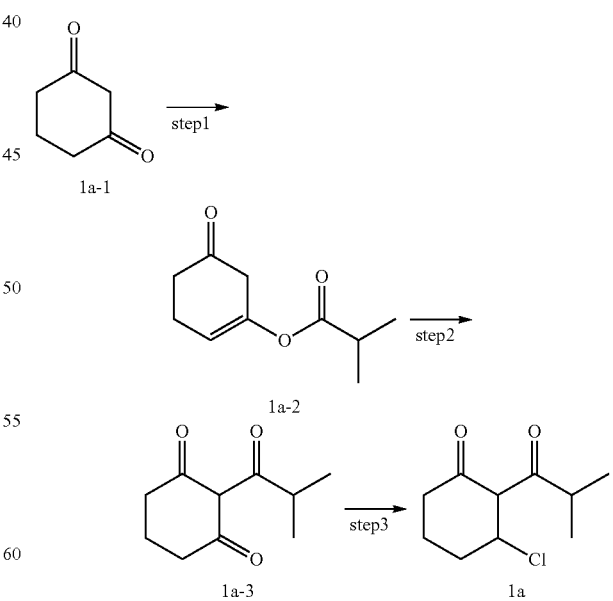

step 1: To a solution of compound 1a-1 (10 g, 89 mmol) in dichloromethane (10 mL) was added isobutyryl chloride (11.2 g, 106 mmol) and triethylamine (18 g, 178 mmol), and the mixture was stirred at room temperature for 2 hours.

TLC was used to monitor the reaction until the end of the reaction. The reaction solution was quenched with water and extracted with dichloromethane. The organic layer was dried and concentrated and then purified by CombiFlash (PE/EA=5:1) to give 8 g of compound 1a-2. MS m/z (ESI): N/A.

step 2: To a solution of compound 1a-2 (8 g, 43 mmol) in dichloromethane (100 mL) was added aluminum trichloride (11.6 g, 86 mmol) in an ice bath, and the mixture was stirred at room temperature for 2 hours. TLC was used to monitor the reaction until the end of the reaction. The reaction solution was quenched with hydrochloric acid and extracted with dichloromethane. The organic layer was dried and concentrated and then purified by combiflash (PE/EA=5:1) to give 2.5 g of compound 1a-3. MS m/z (ESI): N/A.

step 3: A solution of compound 1a-3 (200 mg, 1.1 mmol) in dichloromethane (5 mL) was added into oxalyl chloride (276 mg, 2.2 mmol) and the mixture was stirred at room temperature for 24 hours. The reaction mixture was concentrated to give compound 1a which was used directly in the next step. MS m/z (ESI): N/A.

Preparation of Intermediate 2a

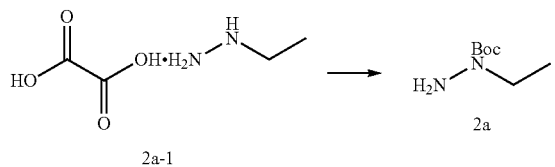

To a solution of compound 2a-1 (8.74 g, 58 mmol) in ethanol (100 mL) was added Boc$_2$O (12.7 g, 58 mmol) and triethylamine (7.7 mL, 58 mmol) in an ice bath under argon atmosphere, and the mixture was stirred at room temperature for 24 hours. The reaction mixture was concentrated and extracted with an ethyl acetate/water system, and the organic layer was dried to obtain compound 2a, which was directly used in the next step. MS m/z (ESI): N/A.

Preparation of Intermediate 3a

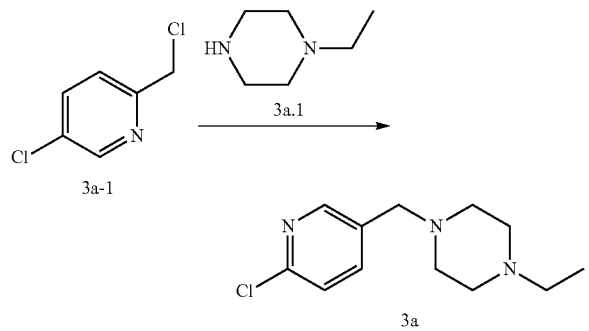

To a solution of compound 3a-1 (3.8 g, 23 mmol) in ethanol (50 mL) was added compound 3a.1 (2.67 g, 23 mmol) and potassium carbonate (4.8 g, 35 mmol), and the mixture was stirred at 65° C. for 12 hours. The reaction mixture was filtered and concentrated to give compound 3a, which was used directly in the next reaction. MS m/z (ESI): 240 [M+H]$^+$.

Preparation of Intermediate 4a

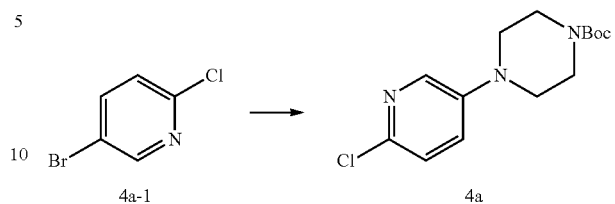

To a solution of compound 4a-1 (9.6 g, 50 mmol), N-Boc piperazine (9.3 g, 50 mmol) in toluene (60 mL) was added Xantphos (1.4 g, 2.5 mmol), Pd$_2$(dba)$_3$ (2.3 g, 2.5 mmol) and sodium t-butoxide (7.2 g, 75 mmol), and the mixture was stirred at 100° C. under nitrogen atmosphere overnight. LC-MS was used to monitor the reaction until the reaction was complete. The reaction solution was filtered, concentrated, and then purified by combiflash (PE/EA=26%) to obtain 13.4 g of compound 4a. MS m/z (ESI): 298 [M+H]$^+$.

Preparation of Intermediate 5a

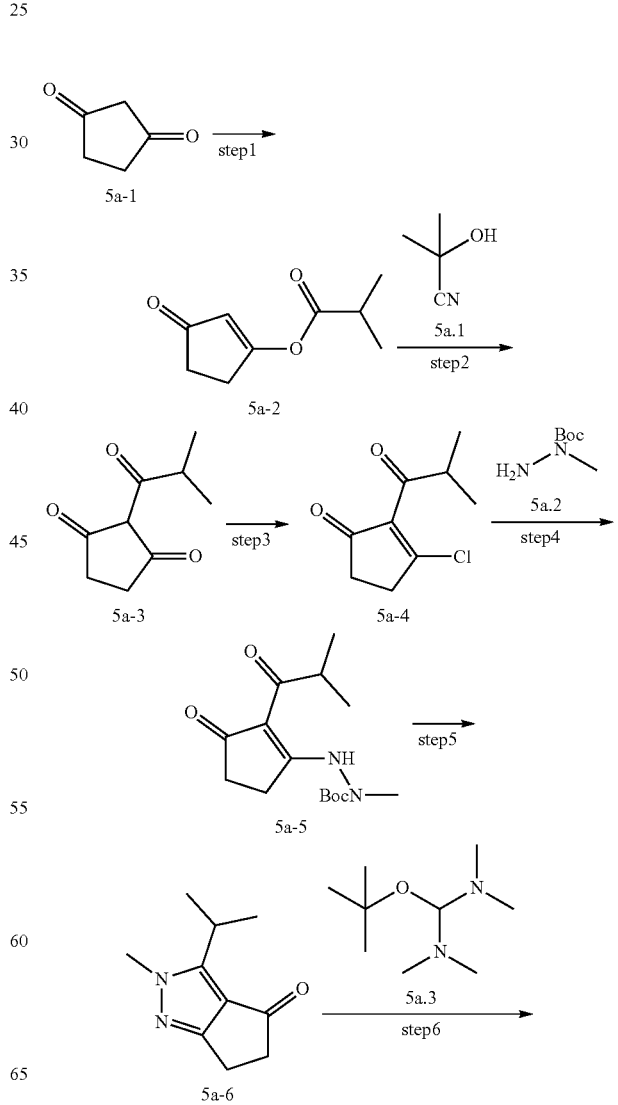

-continued

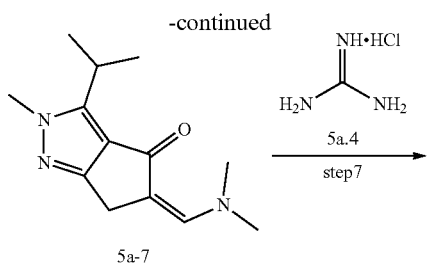

Preparation of Intermediate 6a

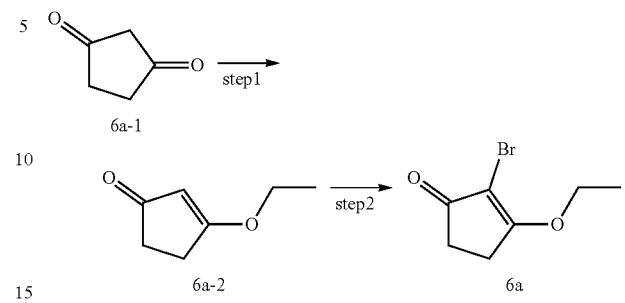

step 1: The preparation method was the same as that for compound 3-2, except that compound 3-1 in the method for 3-2 was replaced by compound 6a-1. MS m/z (ESI): 127 [M+H]$^+$.

step 2: The preparation method was the same as that for compound 3-3, except that compound 3-2 in the method for 3-3 was replaced by compound 6a-2. MS m/z (ESI): 205 [M+H]$^+$.

Preparation of intermediate 7a

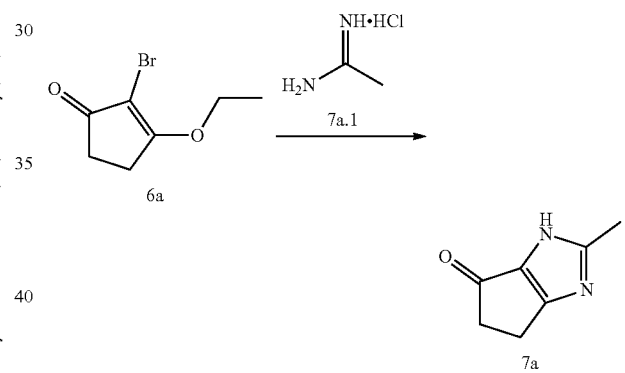

To a solution of compound 6a (2.5 g, 12 mmol) in DMF (20 mL) was added compound 7a.1 (1.13 g, 12 mmol) and potassium carbonate (4.7 g, 34.2 mmol), and the mixture was stirred at 110° C. for 2 hours. TLC was used to monitor the reaction until the reaction was complete. The reaction solution was concentrated and purified by combiflash (DCM:MeOH=15:1) to give 900 mg of compound 7a. MS m/z (ESI): 137[M+H]$^+$.

Preparation of Intermediate 8a

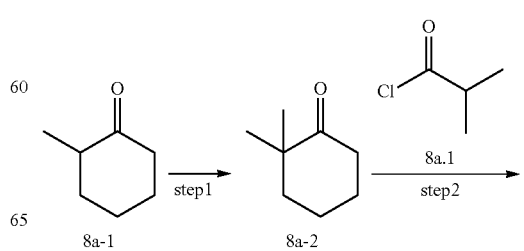

step 1: The preparation method was the same as that for compound 1a-2 except that compound 1a-1 in the method for 1a-2 was replaced by compound 5a-1. MS m/z (ESI): 169 [M+H]$^+$.

step 2: To a solution of compound 5a-2 (5 g, 29.8 mmol) in acetonitrile (50 mL) was added triethylamine (4.2 g, 41.7 mmol) and 5a.1 (1 g, 11.9 mmol), and the mixture was stirred at room temperature for 2 days. LC-MS was used to monitor the reaction until the reaction was complete. The reaction solution was quenched with hydrochloric acid and extracted with ethyl acetate. The organic layer was dried and concentrated and purified by combiflash to give 2.4 g of compound 5a-3. MS m/z (ESI): 169[M+H]$^+$.

step 3: The preparation method was the same as that for compound 1a, except that compound 1a-3 in the method for 1a was replaced by compound 5a-3. MS m/z (ESI): N/A.

step 4: To a solution of compound 5a-4 (344 mg, 1.85 mmol) in THF (5 mL) was added compound 5a.2 (270 mg, 1.85 mmol) and triethylamine (374 mg, 3.7 mmol) in an ice bath, and the mixture was stirred at room temperature for 20 hours. TLC was used to monitor the reaction until the end of the reaction. The reaction solution was concentrated and purified by combiflash to give 309 mg of compound 5a-5. MS m/z (ESI): 297[M+H]$^+$.

step 5: A solution of compound 5a-5 (309 mg, 1.04 mmol) in HCl/1,4-dioxane (4 mL) was stirred at room temperature for 24 hours. LC-MS was used to monitor the reaction until the reaction was complete. The reaction solution was concentrated, added with ethyl acetate for dissolution, and washed with saturated sodium bicarbonate. The organic layer was dried and concentrated to obtain compound 5a-6, which was directly used in the next step. MS m/z (ESI): 179[M+H]$^+$.

step 6: A solution of compound 5a-6 (185 mg, 1.04 mmol) in 5a.3 (3 mL) was stirred at 105° C. for 1 h. The reaction solution was cooled to room temperature, concentrated and dried to give compound 5a-7, which was used directly in the next reaction. MS m/z (ESI): 234[M+H]$^+$.

step 7: To a solution of compound 5a-7 (242 mg, 1.04 mmol) and compound 5a.4 (998 mg, 10.4 mmol) in ethanol (4 mL) was added sodium ethoxide (707 mg, 10.4 mmol), and the mixture was sealed and stirred at 130° C. for 2 days. LC-MS was used to monitor the reaction until the reaction was complete. The reaction was cooled to room temperature, concentrated and purified by combiflash to give 197 mg of compound 5a. MS m/z (ESI): 230[M+H]$^+$.

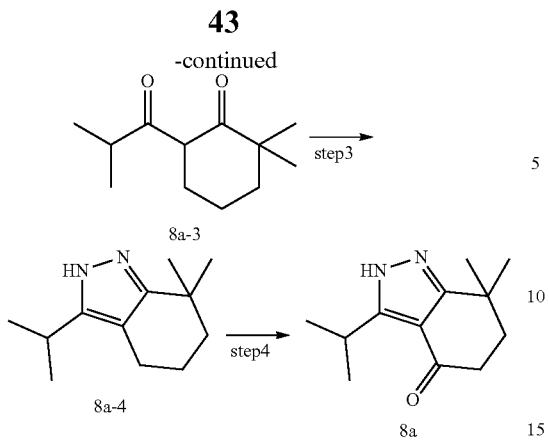

step 1: To a solution of compound 8a-1 (6 g, 53 mmol) in THF (15 mL) was added NaH (2.4 g, 58 mmol) and the mixture was stirred at 60° C. for 3 hours. The reaction solution was cooled in an ice bath, and methyl iodide (15 g, 106 mmol) was added dropwise, and the mixture was stirred at room temperature for 3 hours. The system was added saturated brine to quench the reaction, and concentrated under reduced pressure to remove THF. The aqueous phase was extracted with methyl tert-butyl ether. The organic layer was concentrated and purified by combiflash (PE:EA=25:1) to give 5.8 g of compound 8a-2. MS m/z (ESI): 127[M+H]$^+$.

step 2: To a solution of compound 8a-2 (4.8 g, 38 mmol) in THF (40 mL) was added LiHMDS (40 mL) in an ice bath under argon atmosphere, and the mixture was stirred in an ice bath for 2 minutes, then to the mixture was add compound 8a.1 (4.05 g, 38 mmol). The system slowly warmed to room temperature. The reaction solution was quenched with hydrochloric acid solution, and the organic layer was dried with saturated brine and anhydrous sodium sulfate, then concentrated, and purified by Combiflash (PE:EA=25:1) to obtain 2 g of compound 8a-3. MS m/z (ESI): 197[M+H]$^+$.

step 3: To a solution of compound 8a-3 (2 g, 10 mmol) in ethanol (10 mL) was added hydrazine hydrate (10 mL) at room temperature, and the mixture was stirred at 90° C. for 1 hour and concentrated under reduced pressure to give compound 8a-4, which was used directly in the next step. MS m/z (ESI): 193 [M+H]$^+$.

step 4: To a solution of compound 8a-4 (1.8 g, 9.3 mmol) in acetic acid (10 mL) was added chromium trioxide (1.8 g, 18.6 mmol) at room temperature, and the mixture was stirred at 60° C. for 30 minutes, concentrated under reduced pressure, and the residue was dissolved with ethyl acetate, washed with water and saturated brine, dried over anhydrous sodium sulfate and filtered. The filtrate was concentrated and purified by combiflash (PE:EA=1:1) to give 0.34 g of compound 8a. MS m/z (ESI): 207[M+H]$^+$.

Preparation of Intermediate 9a

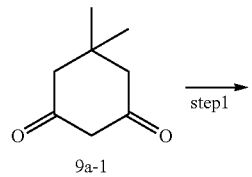

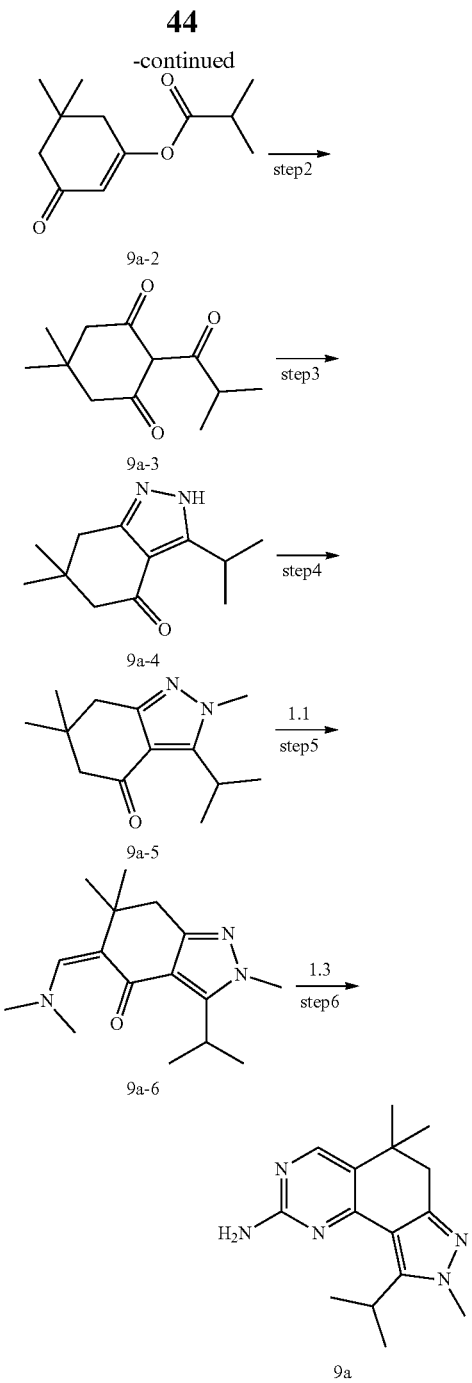

step 1: The preparation method was the same as that for compound 1a-2, except that compound 1a-1 in the method for 1a-2 was replaced by compound 9a-1. MS m/z (ESI): 211[M+H]$^+$.

step 2: The preparation method was the same as that for compound 1a-3, except that compound 1a-2 in the method for 1a-3 was replaced by compound 9a-2.

step 3: The preparation method was the same as that for compound 8a-4, except that compound 8a-3 in the method for 8a-4 was replaced by compound 9a-3. MS m/z (ESI): 207[M+H]$^+$.

step 4: To a solution of compound 9a-4 (4.12 g, 20 mmol) in tetrahydrofuran (100 mL) was added methanol (1.21 mL, 30 mmol), PPh$_3$ (6.812 g, 26 mmol), and then added DIAD (5.15 mL, 26 mmol) in an ice bath, and the mixture was stirred overnight at room temperature. LC-MS was used to monitor the reaction until the reaction was complete. The reaction solution was diluted with ethyl acetate, washed with saturated brine, and the organic layer was dried and concentrated, and then purified by combiflash to obtain compound 9a-5. MS m/z (ESI): 221[M+H]+.

step 5: The preparation method was the same as that for compound 5a-7, except that compound 5a-6 in the method for 5a-7 was replaced by compound 9a-5. MS m/z (ESI): 276[M+H]+.

step 6: The preparation method was the same as that for compound 5a, except that compound 5a-7 in the method for 5a was replaced by compound 9a-6. MS m/z (ESI): 272[M+H]+.

Preparation of Intermediate 10a

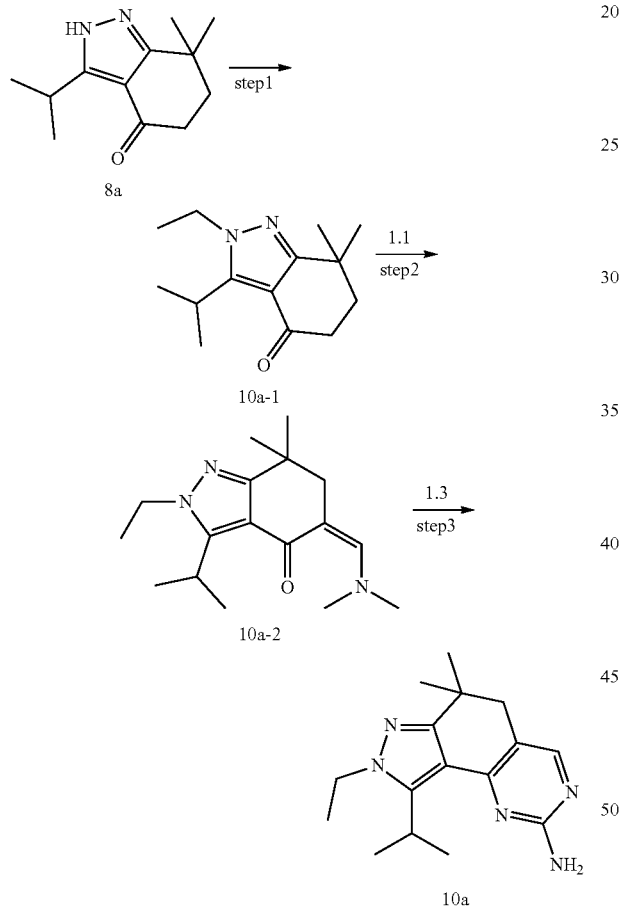

Preparation of Intermediate 11a

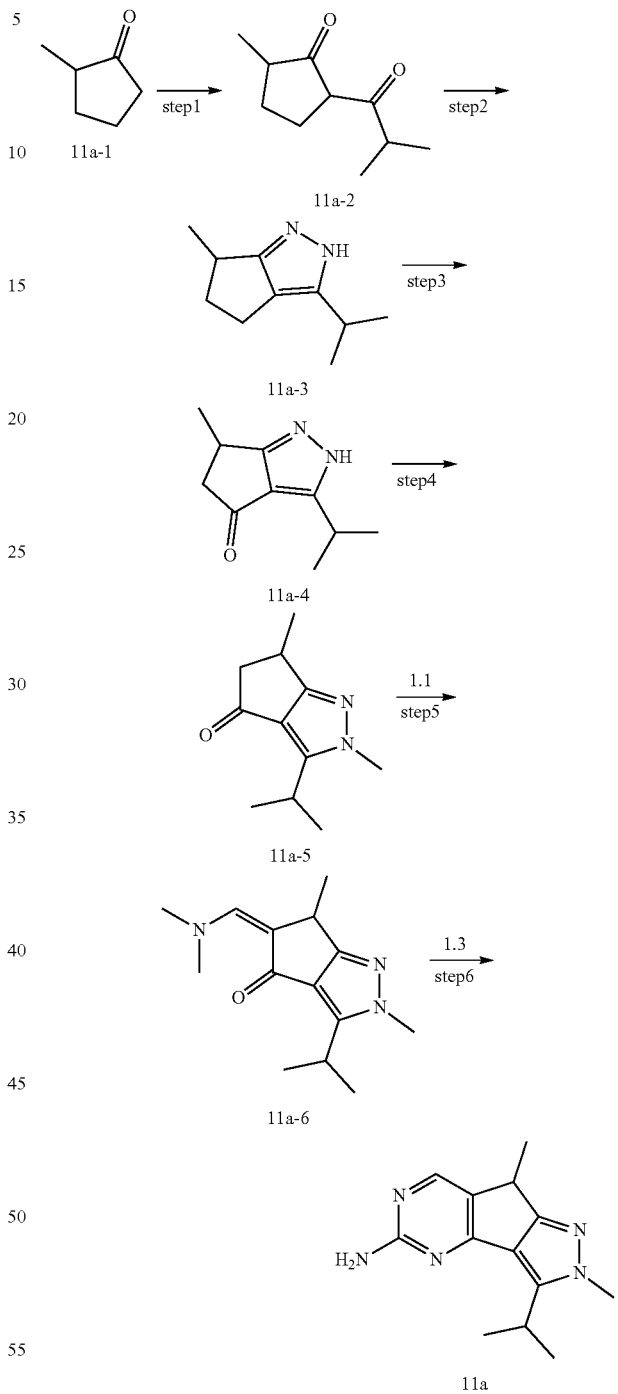

step 1: The preparation method was the same as the method for compound 3-5, except that compound 3-4 and 2-iodopropane in the method for 3-5 were replaced by compound 8a and iodoethane. MS m/z (ESI): 235[M+H]+.

step 2: The preparation method was the same as the method for compound 5a-7, except that compound 55a-6 in the method for 5a-7 was replaced by compound 10a-1. MS m/z (ESI): 290[M+H]+.

step 3: The preparation method was the same as the method for compound 5a, except that compound 5a-7 in the method for 5a was replaced by compound 10a-2. MS m/z (ESI): 286[M+H]+.

step 1: The preparation method was the same as the method for compound 8a-3, except that compound 8a-2 in the method for 8a-3 was replaced by compound 11a-1. MS m/z (ESI): 169[M+H]+.

step 2: The preparation method was the same as the method for compound 8a-4, except that compound 8a-3 in the method for 8a-4 was replaced by compound 11a-2. MS m/z (ESI): 165[M+H]+.

step 3: The preparation method was the same as the method for compound 8a, except that compound 8a-4 in the method for 8a was replaced by compound 11a-3. MS m/z (ESI): 179[M+H]⁺.

step 4: The preparation method was the same as the method for compound 3-5, except that compound 3-4 and 2-iodopropane in the method for 3-5 were replaced by compound 11a-4 and iodomethane. MS m/z (ESI): 193[M+H]⁺.

step 5: The preparation method was the same as the method for compound 5a-7, except that compound 5a-6 in the method for 5a-7 was replaced by compound 11a-5. MS m/z (ESI): 248[M+H]⁺.

step 6: The preparation method was the same as the method for compound 5a, except that compound 5a-7 in the method for 5a was replaced by compound 1 1a-6. MS m/z (ESI): 244[M+H]⁺.

Preparation of Intermediate 12a

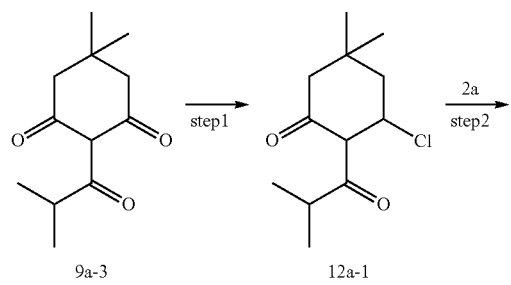

9a-3    12a-1

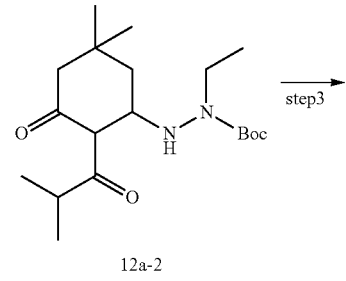

12a-2

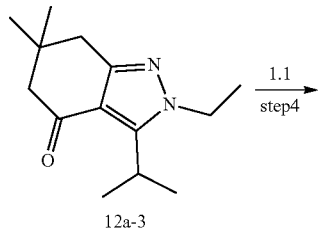

12a-3

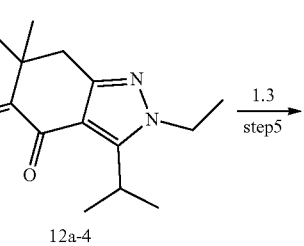

12a-4

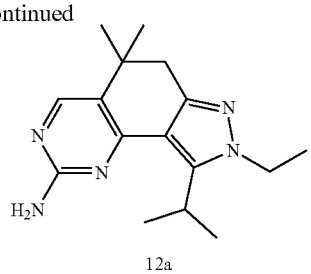

12a step 1: The preparation method was the same as the method for compound 1a, except that compound 1a-3 in the method for 1a was replaced by compound 9a-3. MS m/z (ESI): 229[M+H]⁺.

step 2: The preparation method was the same as the method for compound 5a-5, except that compound 5a-4 and compound 5a.2 in the method for 5a-5 were replaced by compound 12a-1 and compound 2a. MS m/z (ESI): 353[M+H]⁺.

step 3: The preparation method was the same as the method for compound 5a-6, except that compound 5a-5 in the method for 5a-6 was replaced by compound 12a-2. MS m/z (ESI): 235[M+H]⁺.

step 4: The preparation method was the same as the method for compound 5a-7, except that compound 5a-6 in the method for 5a-7 was replaced by compound 12a-3. MS m/z (ESI): 290[M+H]⁺.

step 5: The preparation method was the same as the method for compound 5a, except that compound 5a-7 in the method for 5a was replaced by compound 12a-4. MS m/z (ESI): 286[M+H]⁺.

Preparation of Intermediate 13a

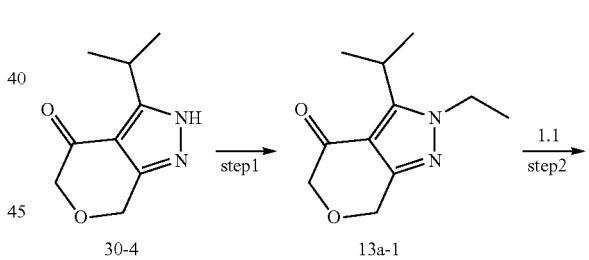

30-4    13a-1

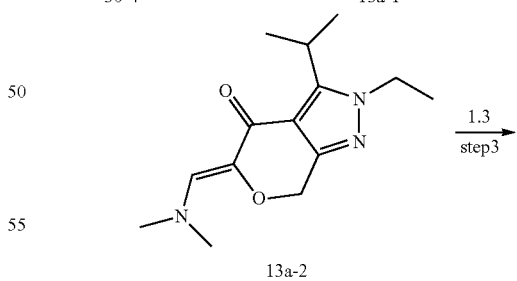

13a-2

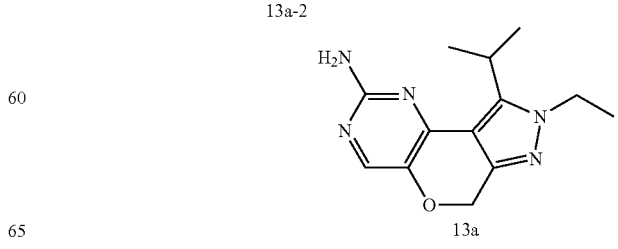

13a step 1: The preparation method was the same as the method for compound 3-5, except that compound 3-4 and 2-iodopropane in the method for 3-5 were replaced by compound 30-4 and iodoethane. MS m/z (ESI): 209[M+H]⁺.

step 2: The preparation method was the same as the method for compound 5a-7, except that compound 5a-6 in the method for 5a-7 was replaced by compound 13a-1. MS m/z (ESI): 264[M+H]⁺.

step 3: The preparation method was the same as the method for compound 5a, except that compound 5a-7 in the method for 5a was replaced by compound 13a-2. MS m/z (ESI): 260[M+H]⁺.

Preparation of Intermediate 14a

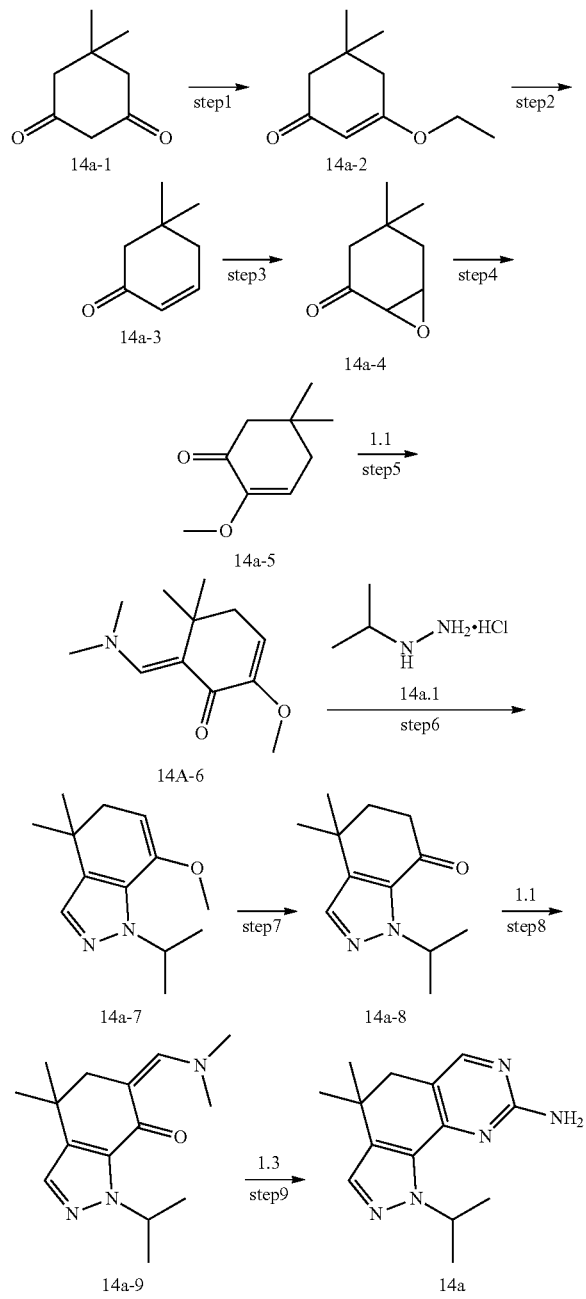

step 1: The preparation method was the same as the method for compound 1-2, except that compound 1-1 in the method for 1-2 was replaced by compound 14a-1. MS m/z (ESI): 169[M+H]⁺.

step 2: To a solution of compound 14a-2 (1 g, 5.94 mmol) in dry THF (6 mL) was added dropwise to LiAlH₄ (90 mg, 2.38 mmol) at 0-5° C. under an argon atmosphere. The mixture was warmed to 25° C. and stirred for 4 hours. The reaction solution was cooled in an ice bath and quenched with ethyl acetate. The mixture was slowly poured into a cooled H₂SO₄ (2M) solution. The resulting solution was extracted twice with methyl tert-butyl ether, dried over anhydrous sodium sulfate and filtered. The filtrate was concentrated under reduced pressure to obtain crude product 14a-3, which was used directly in the next step. MS m/z (ESI): 125[M+H]⁺.

step 3: To a solution of compound 14a-3 (736 mg, 5.94 mmol) in methanol (5 mL) was added dropwise H₂O₂ (3 mL, 29.63 mmol) at 0° C. and the resulting mixture was added to a 2% NaOH solution (1.6 mL) at 0° C. The reaction was stirred at room temperature for 20 h. LC-MS was used to monitor the reaction until the reaction was complete. The mixture was diluted with water and extracted with methyl tert-butyl ether. The organic layers were combined, washed with 5% sodium thiosulfate and saturated brine, respectively, dried over anhydrous sodium sulfate, and concentrated under reduced pressure to give compound 14a-4 as a colorless oil. MS m/z (ESI): 141[M+H]⁺.

step 4: Compound 14a-4 (300 mg, 2.14 mmol) was added to a solution of KOH (120 mg, 2.14 mmol) in methanol (4 mL) at room temperature, and the reaction was stirred at room temperature for 2 days. LC-MS was used to monitor the reaction until the reaction was complete. The mixture was cooled, diluted with water, and extracted with methyl tert-butyl ether. The organic layers were combined, washed with saturated brine, dried over anhydrous sodium sulfate, and concentrated under reduced pressure to give compound 14a-5 as a yellow oil. MS m/z (ESI): 155[M+H]⁺.

step 5: The preparation method was the same as the method for compound 5a-7, except that compound 5a-6 in the method for 5a-7 was replaced by compound 14a-5. MS m/z (ESI): 210[M+H]⁺.

step 6: The preparation method was the same as the method for compound 5a, except that compound 5a-7 and compound 1.3 in the method for 5a were replaced by compound 14a-6 and compound 14a.1. MS m/z (ESI): 221[M+H]⁺.

step 7: The preparation method was the same as the method for compound 43-3, except that compound 43-2 in the method for 43-3 was replaced by compound 14a-7. MS m/z (ESI): 207[M+H]⁺.

step 8: The preparation method was the same as the method for compound 5a-7, except that compound 5a-6 in the method for 5a-7 was replaced by compound 14a-8. MS m/z (ESI): 262[M+H]⁺.

step 9: The preparation method was the same as the method for compound 5a, except that compound 5a-7 in the method for 5a was replaced by compound 14a-9. MS m/z (ESI): 258[M+H]⁺.

Preparation of Intermediate 15a

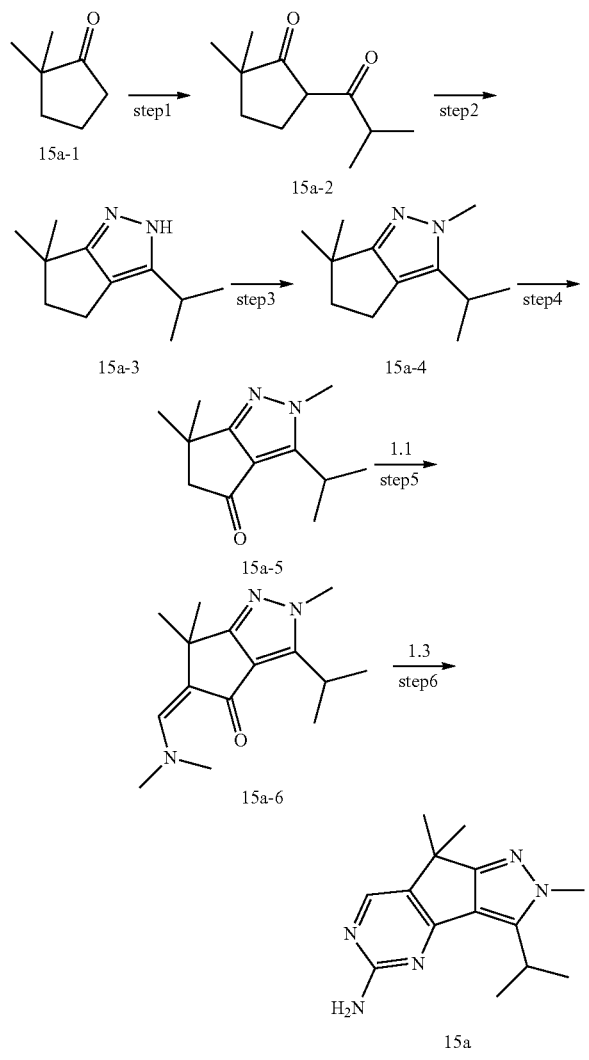

step 1: The preparation method was the same as the method or compound 8a-3, except that compound 8a-2 in the method for 8a-3 was replaced by compound 15a-1.

step 2: The preparation method was the same as the method for compound 8a-4, except that compound 8a-3 in the method for 8a-4 was replaced by compound 15a-2. MS m/z (ESI): 179.2[M+H]$^+$.

step 3: The preparation method was the same as the method for compound 3-5, except that compound 3-4 and 2-iodopropane in the method for 3-5 were replaced by compound 15a-3 and iodomethane. m/z (ESI): 193.3[M+H]$^+$.

step 4: The preparation method was the same as the method for compound 8a, except that compound 8a-4 in the method for 8a was replaced by compound 15a-4. m/z (ESI): 207.3[M+H]$^+$.

step 5: The preparation method was the same as the method for compound 5a-7, except that compound 5a-6 in the method for 5a-7 was replaced by compound 15a-5. MS m/z (ESI): 262.2[M+H]$^+$.

step 6: The preparation method was the same as the method for compound 5a, except that compound 5a-7 in the method for 5a was replaced by compound 15a-6. MS m/z (ESI): 258.2[M+H]$^+$.

Preparation of Intermediate 16a

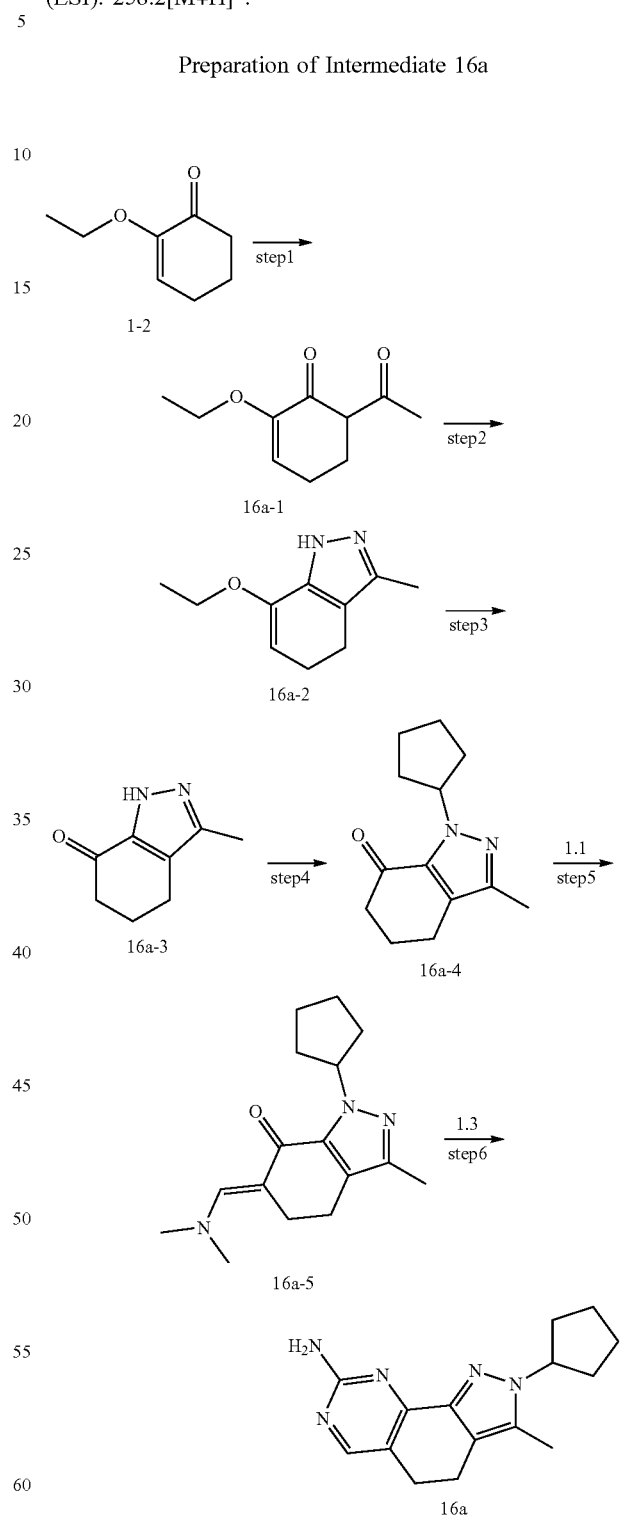

step 1: The preparation method was the same as the method for compound 8a-3, except that compound 8a-2 and isobutyryl chloride in the method for 8a-3 were replaced by compound 1-2 and acetyl chloride. m/z (ESI): 183[M+H]$^+$.

step 2: The preparation method was the same as the method for compound 8a-4, except that compound 8a-3 in the method for 8a-4 was replaced by compound 16a-1. MS m/z (ESI): 179 [M+H]+.

step 3: To a solution of compound 16a-1 (391.6 mg, 2.2 mmol) in ethanol (5 mL) was added dropwise hydrochloric acid (36%, 2 mL) at room temperature and the mixture was stirred at room temperature for 2 h. LC-MS was used to monitor the reaction until the reaction was complete. The reaction solution was concentrated under reduced pressure and then purified by combiflash (volume of PE/EA=40/60) to give compound 16a-3 (133 mg, yield 40%) as a yellow oil. MS m/z (ESI): 151 [M+H]+.

step 4: The preparation method was the same as the method for compound 3-5, except that compound 3-4 and 2-iodopropane in the method for 3-5 were replaced by compound 16a-3 and bromocyclopentane. m/z (ESI): 219 [M+H]+.

step 5: The preparation method was the same as the method for compound 5a-7, except that compound 5a-6 in the method for 5a-7 was replaced by compound 16a-4. MS m/z (ESI): 274[M+H]+.

step 6: The preparation method was the same as the method for compound 5a, except that compound 5a-7 in the method for 5a was replaced by compound 16a-5. MS m/z (ESI): 270[M+H]+.

Preparation of Intermediate 17a step 1: The preparation method was the same as the method for compound 3-5, except that compound 3-4 and 2-iodopropane in the method for 3-5 were replaced by compound 9a-4 and iodomethane. MS m/z (ESI): 221[M+H]+.

step 2: The preparation method was the same as the method for compound 5a-7, except that compound 5a-6 in the method for 5a-7 was replaced by compound 17a-1. MS m/z (ESI): 276[M+H]+.

step 3: The preparation method was the same as the method for compound 5a, except that compound 5a-7 in the method for 5a was replaced by compound 17a-2. MS m/z (ESI): 272[M+H]+.

Preparation of Intermediate 18a

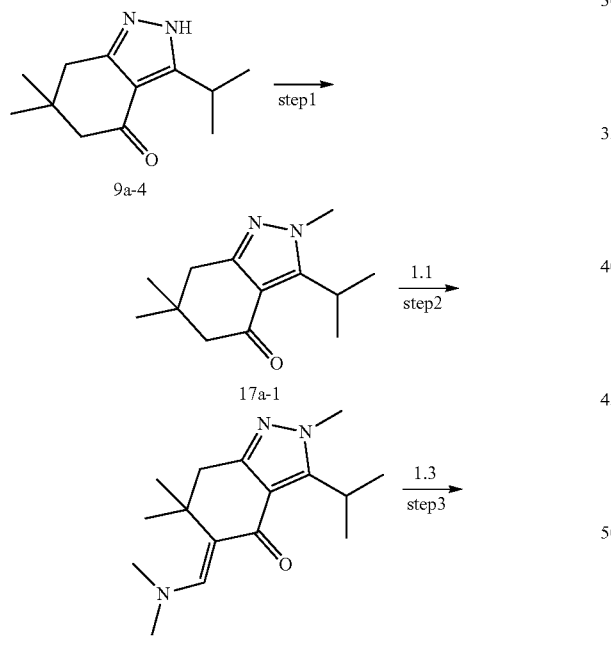

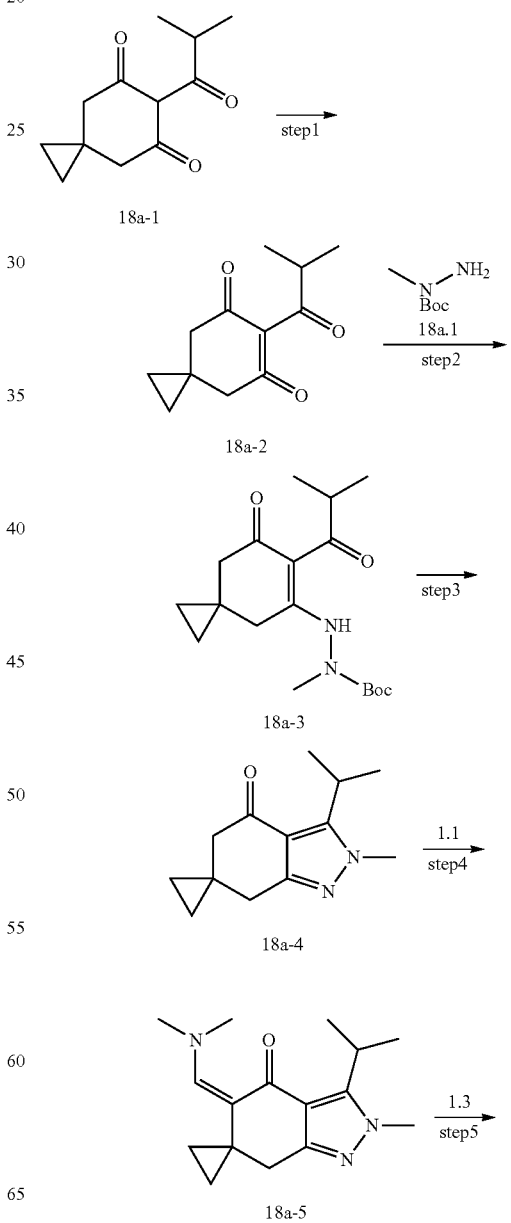

-continued

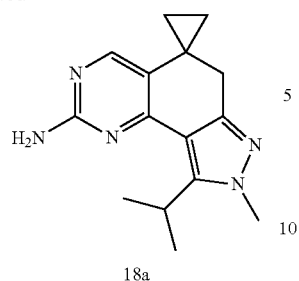

18a

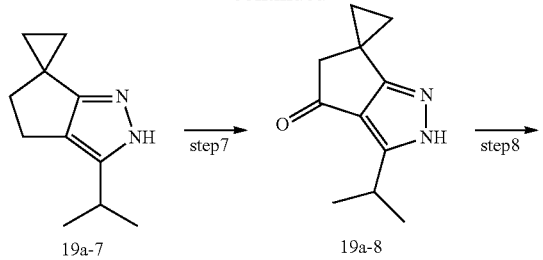

step 1: The preparation method was the same as the method for compound 1a, except that compound 1a-3 in the method for 1a was replaced by compound 18a-1. MS m/z (ESI): 227[M+H]⁺.

step 2: The preparation method was the same as the method for compound 5a-5, except that compound 5a-4 in the method for 5a-5 was replaced by compound 18a-2. MS m/z (ESI): 337[M+H]⁺.

step 3: The preparation method was the same as the method for compound 5a-6, except that compound 5a-5 in the method for 5a-6 was replaced by compound 18a-3. MS m/z (ESI): 219[M+H]⁺.

step 4: The preparation method was the same as the method for compound 5a-7, except that compound 5a-6 in the method for 5a-7 was replaced by compound 18a-4. MS m/z (ESI): 274[M+H]⁺.

step 5: The preparation method was the same as the method for compound 5a, except that compound 5a-7 in the method for 5a was replaced by compound 18a-5. MS m/z (ESI): 270[M+H]⁺.

Preparation of Intermediate 19a

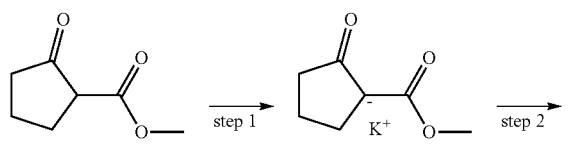

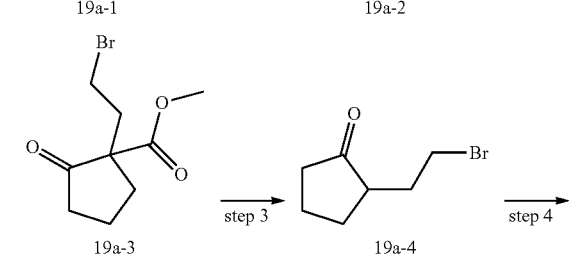

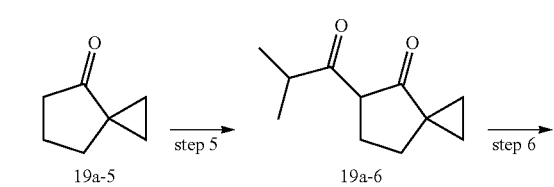

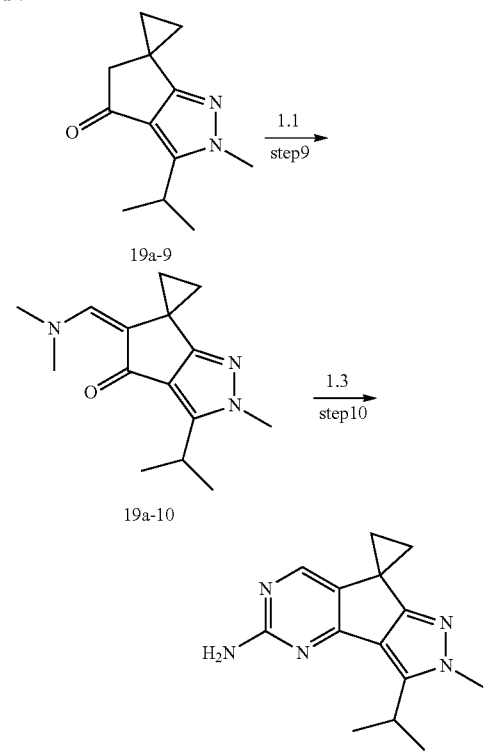

step 1: To a solution of KOH (14.98 g, 267.6 mmol) in water (3.6 mL) and ethanol (67 mL) was added compound 19a-1 (38 g, 267.6 mmol) at 0° C. TME was added after 2 min, the mixture was stirred for 15 min, and filtered. The filter cake was successively washed with ice-ethanol and TME, and then dried to obtain compound 19a-2 (46.7 g, yield 97%).

step 2: A solution of compound 19a-2 (46.7 g, 259 mmol) and 1,2-dibromoethane in DMSO (376 mL) was stirred at room temperature for 2 days. The mixture was added with water, extracted with petroleum ether, and the extractant was dried over anhydrous sodium sulfate, concentrated under reduced pressure and then purified by combiflash to give compound 19a-3 (26 g, yield 41%). MS m/z (ESI): 249[M+H]⁺.

step 3: A solution of compound 19a-3 (9 g, 36.3 mmol) in HBr (40 mL) was heated at reflux for 2 h. The mixture was added water and extracted with ethyl acetate. The organic layer was washed with water, saturated sodium bicarbonate and saturated brine, and then concentrated under reduced pressure. The resulting mixture was purified by combiflash to give compound 19a-4 (4 g, yield 58%). MS m/z (ESI): 249[M+H]⁺.

step 4: A solution of compound 19a-4 (1 g, 5.3 mmol) and K₂CO₃ (2.2 g, 15.8 mmol) in ethanol (18 mL) was heated at reflux for 3 h. The mixture was added water and extracted with petroleum ether. The organic layer was dried over anhydrous sodium sulfate and then concentrated under reduced pressure to give the compound 19a-5, which was directly used in the next step.

step 5: The preparation method was the same as the method for compound 8a-3, except that compound 8a-2 in the method for 8a-3 was replaced by compound 19a-5.

step 6: The preparation method was the same as the method for compound 8a-4, except that compound 8a-3 in the method for 8a-4 was replaced by compound 19a-6. MS m/z (ESI): 177 [M+H]$^+$.

step 7: The preparation method was the same as the method for compound 8a, except that compound 8a-4 in the method for 8a was replaced by compound 19a-7. m/z (ESI): 191[M+H]$^+$.

step 8: The preparation method was the same as the method for compound 3-5, except that compound 3-4 and 2-iodopropane in the method for 3-5 were replaced by compound 19a-8 and iodomethane. m/z (ESI): 205[M+H]$^+$.

step 9: The preparation method was the same as the method for compound 5a-7, except that compound 5a-6 in the method for 5a-7 was replaced by compound 19a-9. MS m/z (ESI): 260[M+H]$^+$.

step 10: The preparation method was the same as the method for compound 5a, except that compound 5a-7 in the method for 5a was replaced by compound 19a-10. MS m/z (ESI): 256[M+H]$^+$.

Preparation of Intermediate 20a

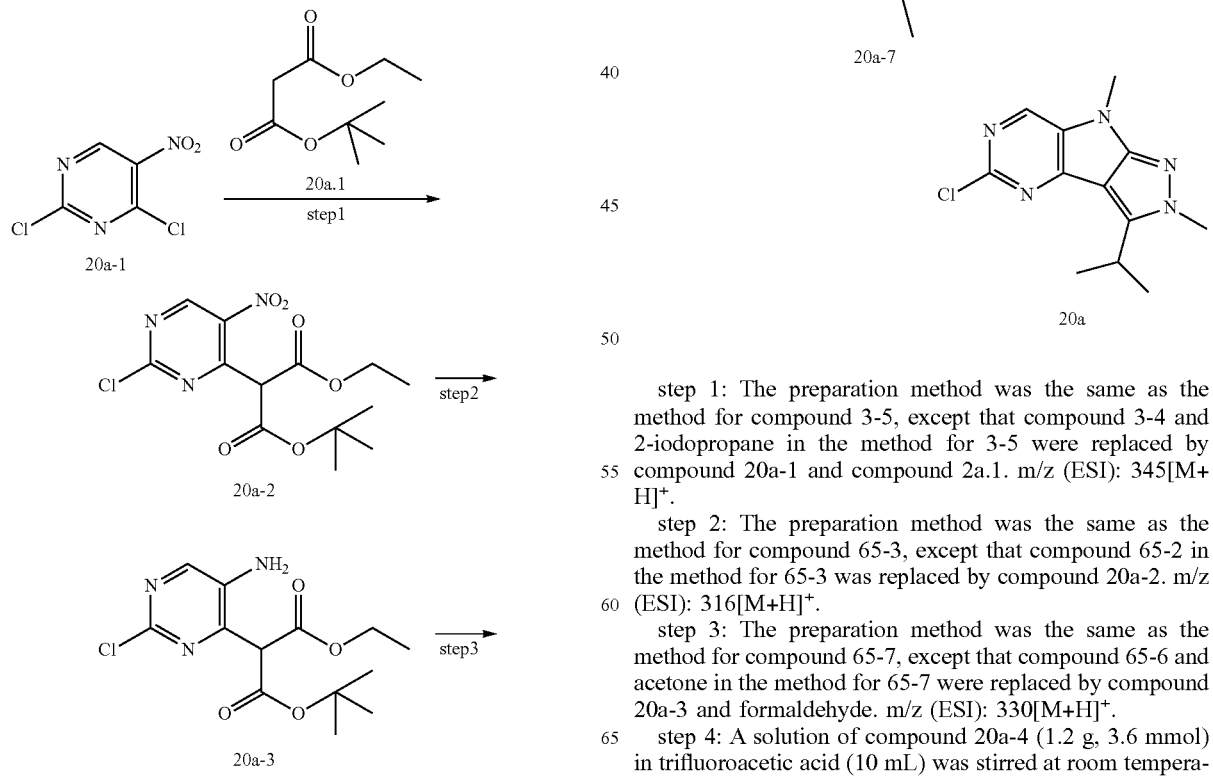

step 1: The preparation method was the same as the method for compound 3-5, except that compound 3-4 and 2-iodopropane in the method for 3-5 were replaced by compound 20a-1 and compound 2a.1. m/z (ESI): 345[M+H]$^+$.

step 2: The preparation method was the same as the method for compound 65-3, except that compound 65-2 in the method for 65-3 was replaced by compound 20a-2. m/z (ESI): 316[M+H]$^+$.

step 3: The preparation method was the same as the method for compound 65-7, except that compound 65-6 and acetone in the method for 65-7 were replaced by compound 20a-3 and formaldehyde. m/z (ESI): 330[M+H]$^+$.

step 4: A solution of compound 20a-4 (1.2 g, 3.6 mmol) in trifluoroacetic acid (10 mL) was stirred at room temperature for 4 h. LC-MS was used to monitor the reaction until the reaction was complete. The reaction solution was concentrated to give compound 20a-5, which was used directly for the next reaction. MS m/z (ESI): 184[M+H]+.

step 5: The preparation method was the same as the method for compound 3-5, except that compound 3-4 and 2-iodopropane in the method for 3-5 were replaced by compound 20a-5 and compound 20a.2. m/z (ESI): 254[M+H]+.

step 6: Compound 20a-6 (650 mg, 2.6 mmol) was added phosphorus oxychloride (30 mL), and the mixture was stirred at 120° C. for 2 h. The reaction solution was concentrated to give compound 20a-7, which was used directly for the next reaction. m/z (ESI): 292[M+H]+.

step 7: The preparation method was the same as the method for compound 8a-4, except that compound 8a-3 in the method for 8a-4 was replaced by compound 20a-7. 50 mg of compound 20a was obtained by purifying through combiflash. m/z (ESI): 250[M+H]+.

Preparation of Intermediate 21a

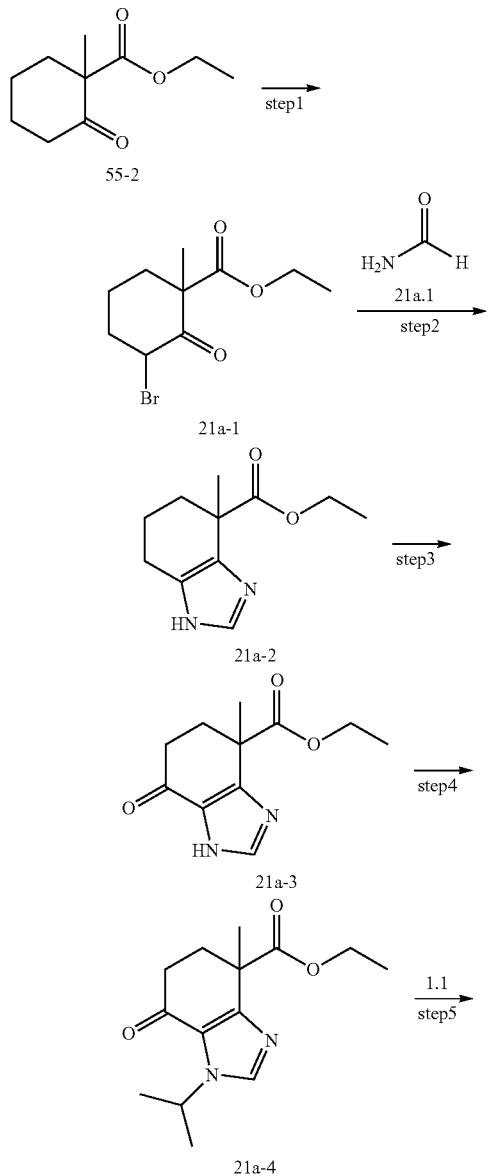

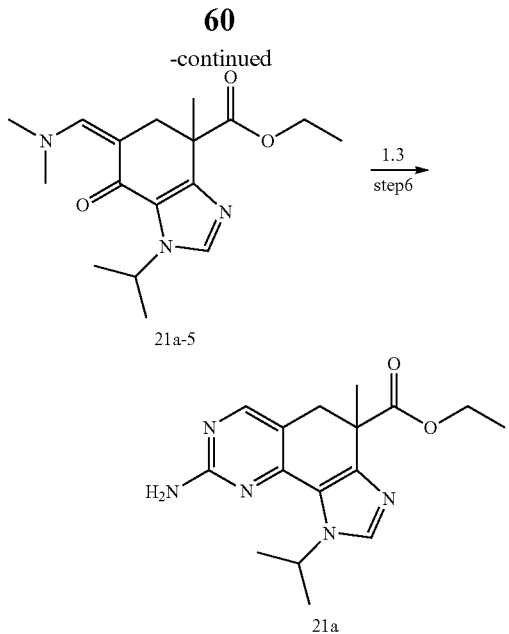

step 1: The preparation method was the same as the method for compound 3-3, except that compound 3-2 in the method for 3-3 was replaced by compound 55-2. MS m/z (ESI): 263[M+H]+.

step 2: To compound 21a-1 (2.5 g, 9.5 mmol) was added compound 21a.1 (5 mL) and the mixture was microwaved at 180° C. for 30 min. The reaction solution was concentrated and purified by combiflash to give compound 21a-2 (1 g, yield 52%). MS m/z (ESI): 209[M+H]+.

step 3: The preparation method was the same as the method for compound 8a, except that compound 8a-4 in the method for 8a was replaced by compound 21a-2. MS m/z (ESI): 223[M+H]+.

step 4: The preparation method was the same as the method for compound 3-5, except that compound 3-4 in the method for 3-5 was replaced by compound 21a-3. MS m/z (ESI): 265[M+H]+.

step 5: The preparation method was the same as the method for compound 5a-7, except that compound 5a-6 in the method for 5a-7 was replaced by compound 21a-4. MS m/z (ESI): 320[M+H]+.

step 6: The preparation method was the same as the method for compound 5a, except that compound 5a-7 in the method for 5a was replaced by compound 21a-5. MS m/z (ESI): 316[M+H]+.

Example 1: Preparation of N-(5-(piperazin-1-yl)pyridin-2-yl)-1-(tetrahydro-2H-pyran-4-yl)-4,5-dihydro-1Hydro-pyrazolo[4,3-H]quinazolin-8-amine (Compound P-1)

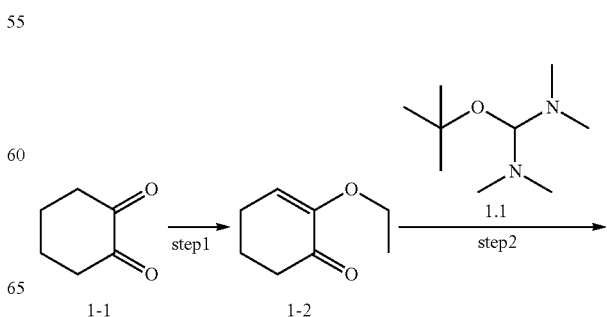

-continued

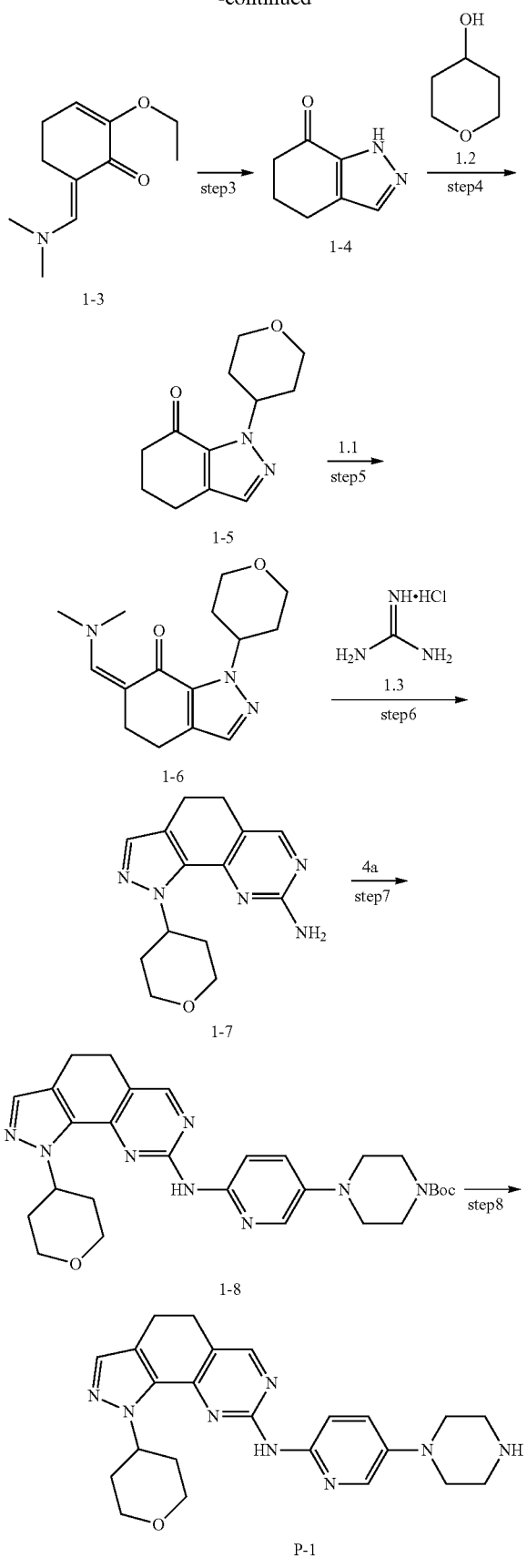

step 1: To a solution of compound 1-1 (15 g, 134 mmol) in ethanol (260 mL) and toluene (150 mL) was added 1.1 g of TsOH, and the mixture was stirred at 110° C. overnight. The reaction solution was cooled to room temperature, concentrated and then purified by combiflash (PE/EA=20%) to obtain 17 g of Compound 1-2. MS m/z (ESI): 141[M+H]$^+$.

step 2: Compound 1-2 (17 g, 121 mmol) was added 60 mL of compound 1.1 and the mixture was stirred at 110° C. for 2 hours. The reaction solution was cooled to room temperature, concentrated and dried to give compounds 1-3, which were used directly in the next reaction step. MS m/z (ESI): 196[M+H]$^+$.

step 3: To a solution of compound 1-3 (20 g, 103 mmol) in ethanol (200 mL) was added hydrazine hydrate (6 g, 103 mmol) and the mixture was stirred at 80° C. overnight. The reaction solution was cooled to room temperature, concentrated and purified by combiflash (PE/EA=37%) to give 8.4 g of compound 1-4. MS m/z (ESI): 137[M+H]$^+$.

step 4: To a solution of compound 1-4 (500 mg, 3.67 mmol), compound 1.2 (750 mg, 7.35 mmol) and PPh$_3$ (1.9 g, 7.35 mmol) in tetrahydrofuran (15 mL) was added DIAD (1.5 g, 7.35 mmol) in an ice bath. The mixture was stirred at room temperature overnight. LC-MS was used to monitor the reaction until the reaction was complete. The reaction solution was concentrated and purified by combiflash (PE/EA=25%) to obtain 200 mg of compound 1-5. MS m/z (ESI): 221[M+H]$^+$.

step 5: The preparation method was the same as the method for compound 1-3, except that compound 1-2 in the method for 1-3 was replaced by compound 1-5. MS m/z (ESI): 276[M+H]$^+$.

step 6: To a solution of compound 1-6 (220 mg, 0.8 mmol) and compound 1.3 (800 mg, 8 mmol) in ethanol (8 mL) was added sodium ethoxide (560 mg, 8 mmol) and the mixture was stirred at 130° C. overnight. LC-MS was used to monitor the reaction until the reaction was complete. The reaction solution was cooled to room temperature, concentrated and purified by combiflash (PE/EA=26%) to give 130 mg of compound 1-7. MS m/z (ESI): 273[M+H]$^+$.

step 7: To a solution of compound 1-7 (130 mg, 0.48 mmol), 4a (150 mg, 0.48 mmol) in 1,4-dioxane (5 mL) was added to Xantphos (14 mg, 0.024 mmol), Pd$_2$(dba)$_3$ (22 mg, 0.024 mmol) and sodium tert-butoxide (95 mg, 0.96 mmol), and the mixture was microwaved at 150° C. under a nitrogen atmosphere for 45 minutes. LC-MS was used to monitor the reaction until the reaction was complete. The reaction solution was filtered, and the filtrate was concentrated and purified by combiflash (DCM/MeOH=30%) to obtain 90 mg of compound 1-8. MS m/z (ESI): 533[M+H]$^+$.

step 8: To a solution of compound 1-8 (90 mg, 0.169 mmol) in dichloromethane (5 mL) was added 2 mL of trifluoroacetic acid, and the mixture was stirred at room temperature for 30 minutes. LC-MS was used to monitor the reaction until the reaction was complete. The reaction solution was concentrated and purified by Prep-HPLC to give compound P-1 (27.3 mg, 37%) as a white solid. MS m/z (ESI): 433[M+H]$^+$; $^1$H NMR (400 MHz, CDCl$_3$) □9.92 (s, 1H), 8.73 (s, 2H), 8.36 (s, 1H), 8.02-8.03 (d, 1H), 7.88-7.90 (d, 1H), 7.52-7.55 (t, 1H), 7.44 (s, 1H), 5.67-5.72 (m, 1H), 3.87-3.91 (m, 2H), 3.42-3.47 (t, 2H), 3.24-3.33 (t, 8H), 2.68-2.76 (m, 4H), 1.96-2.06 (m, 2H), 1.81-1.83 (d, 2H).

Example 2: Preparation of 8-ethyl-N-(5-((4-methylpiperazin-1-yl)methyl)pyridin-2-yl)-9-isopropyl-6,8-dihydro-5H-pyrazolo[3,4-H]quinolin-2-amine (Compound P-2)

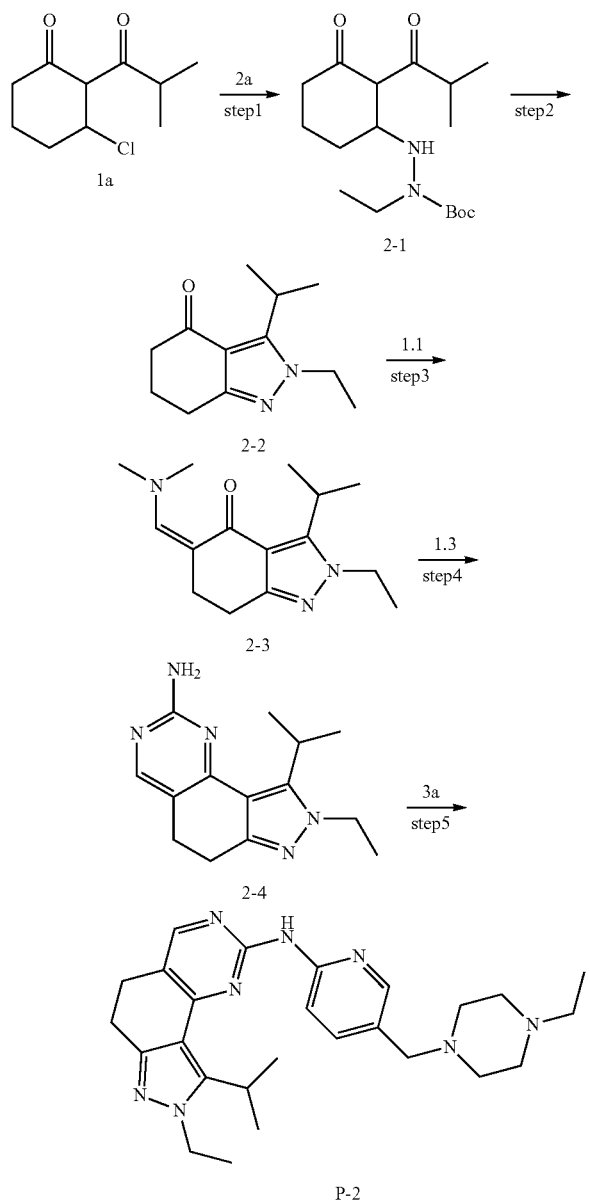

step 1: To a solution of compound 1a (5.5 g, 27 mmol) in THF (100 mL) was added compound 2a (4.4 g, 27 mmol) and triethylamine (5.5 g, 54 mmol) at −35° C., and the mixture was stirred at room temperature for 24 hours. TLC was used to monitor the reaction until the end of the reaction. The reaction solution was concentrated and purified by combiflash (PE:EA=5:1) to obtain 4.6 g of compound 2-1. MS m/z (ESI): N/A.

step 2: To a solution of compound 2-1 (4.6 g, 14.1 mmol) in 1,4-dioxane (12 mL) was added hydrochloric acid/1,4-dioxane (20 mL), and the mixture was stirred at room temperature for 24 hours. LC-MS was used to monitor the reaction until the reaction was complete. The reaction solution was concentrated, and the residue was dissolved in methylene chloride, and the mixture was washed with sodium hydroxide (1N) and saturated brine, and dried to obtain compound 2-2. MS m/z (ESI): 207[M+H]$^+$.

step 3: The preparation method was the same as the method for compound 1-3, except that compound 1-2 in the method for 1-3 was replaced by compound 2-2. MS m/z (ESI): 207[M+H]$^+$.

step 4: To a solution of compound 2-3 (3.3 g, 12.6 mmol) in ethanol (20 mL) was added compound 1.3 (12.8 g, 126 mmol) and sodium ethoxide (9 g, 126 mmol), and the mixture was stirred in a sealed tube at 110° C. for 16 hours. LC-MS was used to monitor the reaction until the reaction was complete. The reaction solution was concentrated and purified by combiflash (PE:EA=3:1) to give 1.7 g of compound 2-4. MS m/z (ESI): 258[M+H]$^+$.

step 5: The preparation method was the same as the method for compound 1-8, except that compounds 1-7 and 4a in the method for 1-8 were replaced by compounds 2-4 and 3a. Compound P-2 (52 mg, 67%) as a white solid was obtained by purifying through Prep-HPLC. MS m/z (ESI): 461[M+H]$^+$; $^1$H NMR (400 MHz, DMSO) δ 9.24 (s, 1H), 8.22 (s, 1H), 8.11 (d, 1H), 8.08 (d, 1H), 7.60 (dd, 1H), 4.13 (q, 2H), 3.92 (dt, 1H), 3.39 (s, 2H), 2.77 (t, 2H), 2.67 (t, 2H), 2.45-2.15 (m, 10H), 1.38 (d, 6H), 1.32 (t, 3H), 0.94 (t, 3H).

Example 3: Preparation of 2-ethyl-N-(5-((4-methylpiperazin-1-yl)methyl)pyridin-2-yl)-1-isopropyl-4,5-dihydro-1H-imidazo[4,5-H]quinazolin-8-amine (Compound P-3)

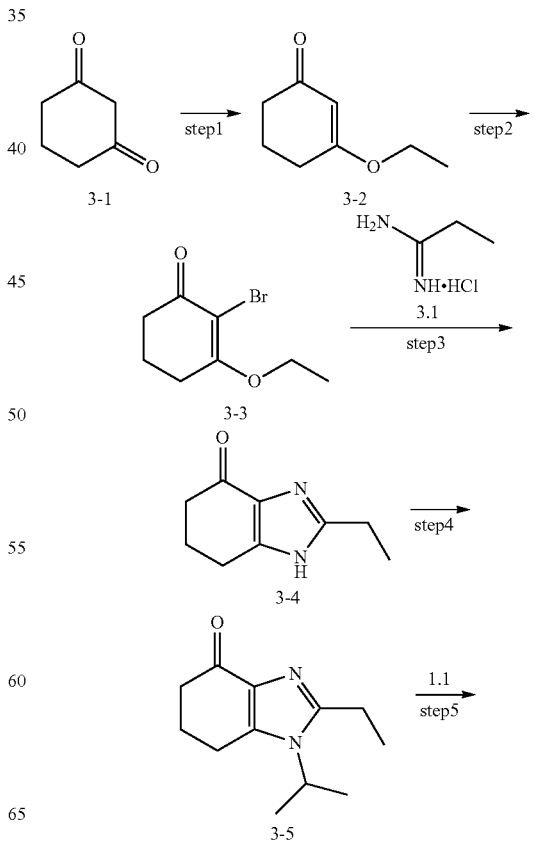

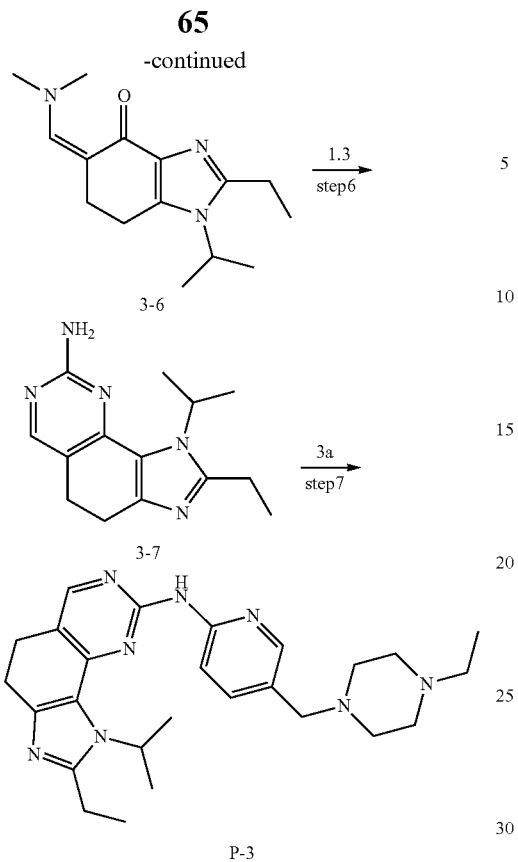

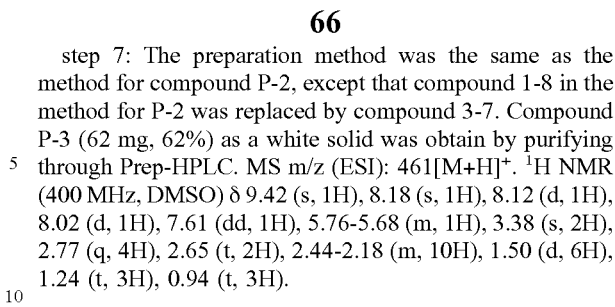

step 7: The preparation method was the same as the method for compound P-2, except that compound 1-8 in the method for P-2 was replaced by compound 3-7. Compound P-3 (62 mg, 62%) as a white solid was obtain by purifying through Prep-HPLC. MS m/z (ESI): 461[M+H]+. 1H NMR (400 MHz, DMSO) δ 9.42 (s, 1H), 8.18 (s, 1H), 8.12 (d, 1H), 8.02 (d, 1H), 7.61 (dd, 1H), 5.76-5.68 (m, 1H), 3.38 (s, 2H), 2.77 (q, 4H), 2.65 (t, 2H), 2.44-2.18 (m, 10H), 1.50 (d, 6H), 1.24 (t, 3H), 0.94 (t, 3H).

Example 4: Preparation of 8-ethyl-9-isopropyl-N-(5-(piperazin-1-yl)pyridin-2-yl)-6,8-dihydro-5H-pyrazolo[3,4-H]quinazolin-2-amine (Compound P-4)

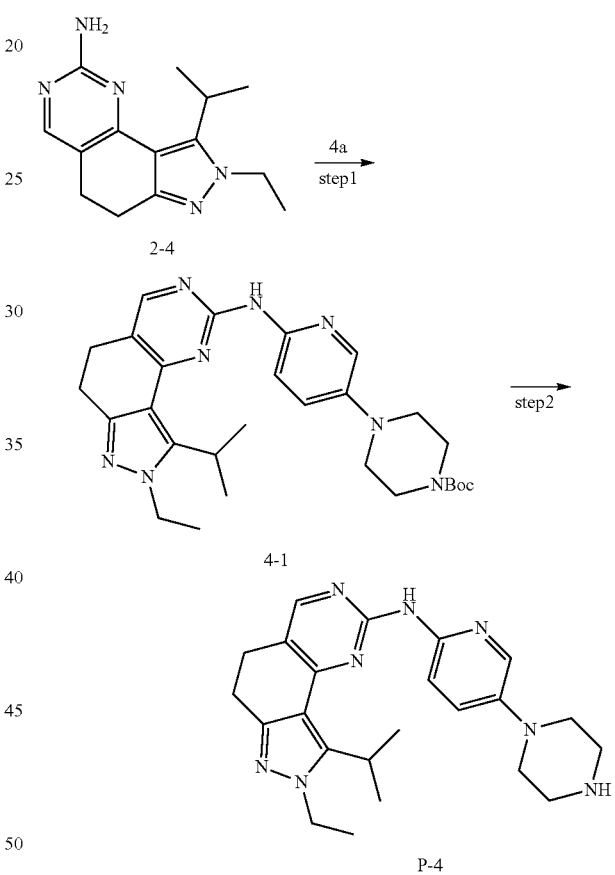

step 1: The preparation method was the same as the method for compound 1-2, except that compound 1-1 in the method for 1-2 was replaced by compound 3-1. MS m/z (ESI): N/A.

step 2: To a solution of compound 3-2 (3 g, 21 mmol) in dichloromethane (30 mL) was added NBS (4.2 g, 23 mmol) and the mixture was stirred at room temperature for 2 hours. LC-MS was used to monitor the reaction until the reaction was complete. The reaction solution was concentrated and purified by combiflash (PE:EA=3:1) to give 3.5 g of compound 3-3. MS m/z (ESI): 219[M+H]+.

step 3: To a solution of compound 3-3 (2.5 g, 11.4 mmol) in DMF (20 mL) was added compound 3.1 (1.25 g, 11.4 mmol) and potassium carbonate (5.7 g, 34.2 mmol), and the mixture was stirred at 110° C. for 2 hours. TLC was used to monitor the reaction until the reaction was complete. The reaction mixture was concentrated and purified by combiflash (DCM:MeOH=15:1) to give 900 mg of compound 3-4. MS m/z (ESI): N/A.

step 4: To a solution of compound 3-4 (125 mg, 0.08 mmol) in DMF (10 mL) was added NaH (91 mg, 0.24 mmol) and 2-iodopropane (388 mg, 0.24 mmol) and the mixture was stirred at 80° C. for 2 hours. LC-MS was used to monitor the reaction until the reaction was complete. The reaction solution was quenched with ammonium chloride, concentrated and purified by combiflash (DCM:MeOH=20:1) to obtain 60 mg of compound 3-5. MS m/z (ESI): 207[M+H]+.

step 5: The preparation method was the same as the method for compound 1-3, except that compound 1-2 in the method for 1-3 was replaced by compound 3-5. MS m/z (ESI): 262[M+H]+.

step 6: The preparation method was the same as the method for compound 2-4, except that compound 2-3 in the method for 2-4 was replaced by compound 3-6. MS m/z (ESI): 258[M+H]+.

step 1: The preparation method was the same as the method for compound 1-8, except that compound 1-7 in the method for 1-8 was replaced by compound 2-4. MS m/z (ESI): 519[M+H]+.

step 2: The preparation method was the same as the method for compound P-1, except that compound 1-8 in the method for P-1 was replaced by compound 4-1. Compound P-4 (1.3 g, 81%) as a white solid was obtained. MS m/z (ESI): 419[M+H]+; 1H NMR (400 MHz, DMSO) δ 8.91 (s, 1H), 8.17 (s, 1H), 7.93 (d, 1H), 7.92 (s, 1H), 7.35 (dd, 1H), 4.12 (q, 2H), 3.89 (dt, 1H), 3.03-2.89 (m, 4H), 2.80 (dd, 4H), 2.78-2.70 (m, 2H), 2.70-2.56 (m, 2H), 1.37 (d, 6H), 1.31 (t, 3H).

Example 5

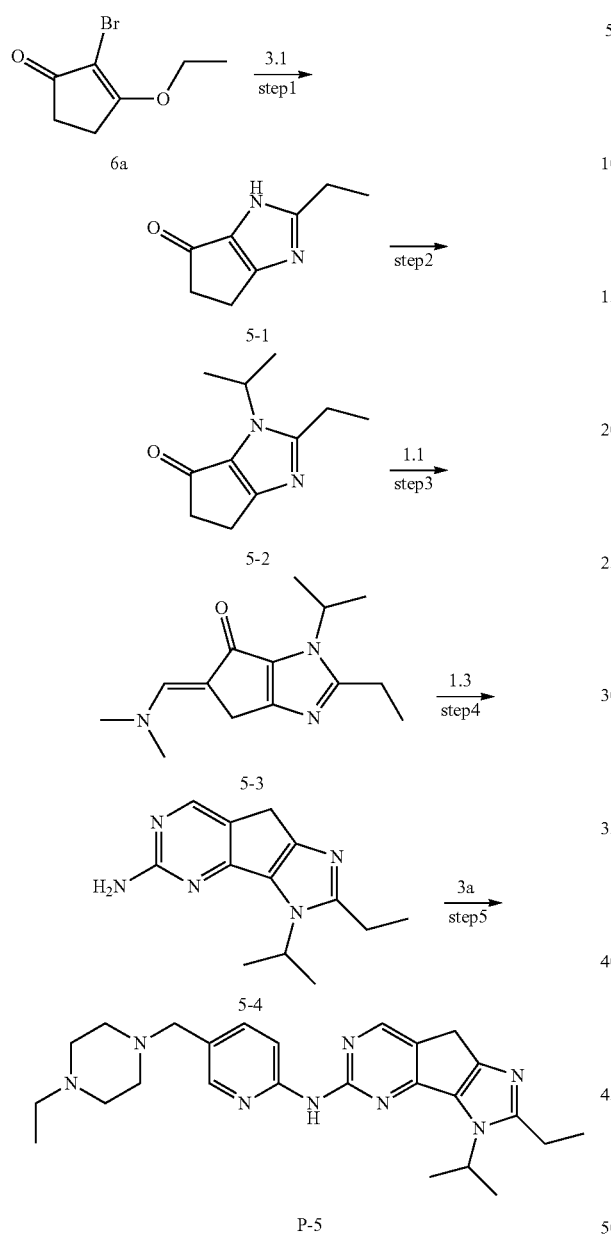

step 1: The preparation method was the same as the method for compound 3-4, except that compound 3-3 in the method for 3-4 was replaced by compound 6a. MS m/z (ESI): N/A.

step 2: The preparation method was the same as the method for compound 3-5, except that compound 3-4 in the method for 3-5 was replaced by compound 5-1. MS m/z (ESI): 193[M+H]+.

step 3: The preparation method was the same as the method for compound 3-6, except that compound 3-5 in the method for 3-6 was replaced by compound 5-2. MS m/z (ESI): 248[M+H]+.

step 4: The preparation method was the same as the method for compound 3-7, except that compound 3-6 in the method for 3-7 was replaced by compound 5-3. MS m/z (ESI): 244[M+H]+.

step 5: The preparation method was the same as the method for compound P-3, except that compound 3-7 in the method for P-3 was replaced by compound 5-4. Compound P-5 (13 mg, 14%) as a white solid was obtained by purification through Prep-HPLC. MS m/z (ESI): 447[M+H]+; 1H NMR (400 MHz, DMSO) δ 9.44 (s, 1H), 8.35-8.33 (m, 2H), 8.15 (s, 1H), 7.67 (d, 1H), 4.66-4.63 (m, 1H), 3.49 (s, 2H), 3.42 (s, 2H), 2.86 (q, 2H), 2.49-2.26 (m, 10H), 1.65 (d, 6H), 1.27 (t, 3H), 0.97 (t, 3H).

Example 6

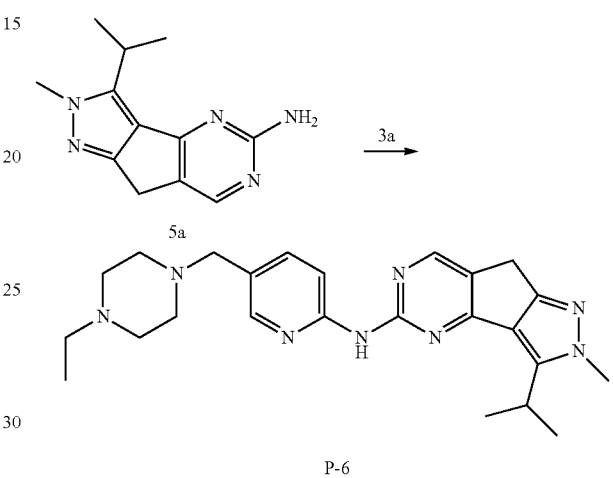

The preparation method was the same as the method for compound P-3, except that compound 3-7 in the method for P-3 was replaced by compound 5a. Compound P-6 (14 mg, 11.2%) as a white solid was obtained by purification through Prep-HPLC. MS m/z (ESI): 433[M+H]+; 1H NMR (400 MHz, DMSO) δ9.37 (s, 1H), 8.38 (s, 1H), 8.23 (d, 1H), 8.14 (s, 1H), 7.63 (d, 1H), 3.90 (s, 3H), 3.62 (s, 2H), 3.42 (s, 2H), 3.30-3.25 (m, 1H), 2.40-2.26 (m, 10H), 1.48 (d, 6H), 0.97 (t, 3H).

Example 7

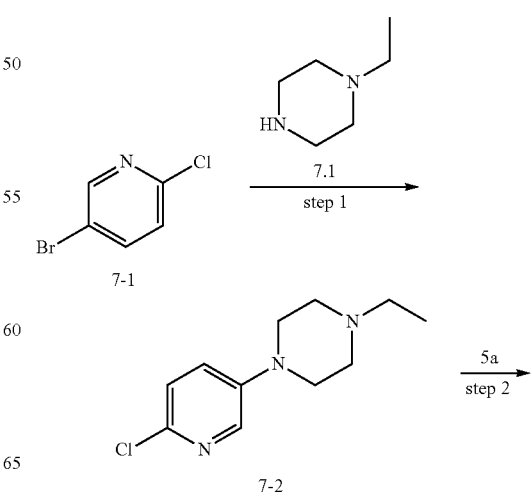

-continued

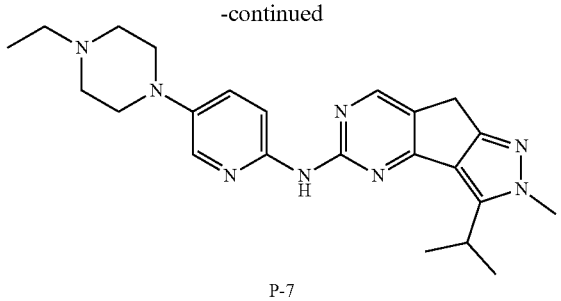

P-7 step 1: The preparation method was the same as the method for compound 4a, except that compound N-Boc piperazine in the method for 4a was replaced by compound 7.1. MS m/z (ESI): 226[M+H]).

step 2: The preparation method was the same as the method for P-6, except that compound 3a in the method for P-6 was replaced by compound 7-2. Compound P-7 (358 mg, 47%) as a white solid was obtained by purification through Prep-HPLC. MS m/z (ESI): 419[M+H]$^+$; $^1$H NMR (400 MHz, DMSO) δ 9.00 (s, 1H), 8.33 (s, 1H), 8.19 (d, 1H), 7.97 (s, 1H), 7.40 (d, 1H), 3.89 (s, 3H), 3.59 (s, 2H), 3.30-3.27 (m, 1H), 3.12-3.09 (m, 4H), 2.54-2.47 (m, 4H), 2.37 (q, 2H), 1.48 (d, 6H), 1.03 (t, 3H).

Example 8

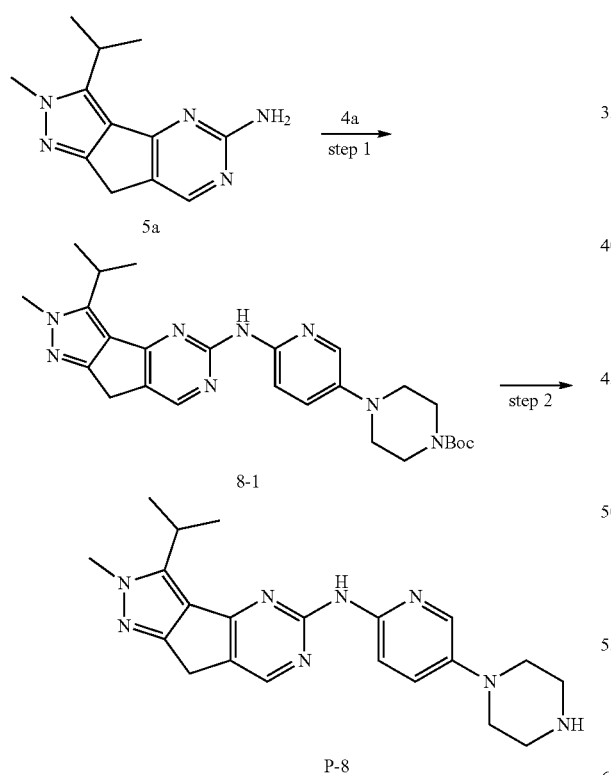

step 1: The preparation method was the same as the method for P-6, except that compound 3a in the method for P-6 was replaced by compound 4a. MS m/z (ESI): 491[M+H]$^+$.

step 2: The preparation method was the same as the method for P-1, except that compound 1-8 in the method for P-1 was replaced by compound 8-1. Compound P-8 (965 mg, 59%) as a white solid was obtained by purification through Prep-HPLC. MS m/z (ESI): 391[M+H]$^+$; $^1$H NMR (400 MHz, DMSO) δ 9.09 (s, 1H), 8.33 (s, 1H), 8.18 (d, 1H), 7.96 (s, 1H), 7.38 (d, 1H), 3.89 (s, 3H), 3.60 (s, 2H), 3.30-3.25 (m, 1H), 3.05-3.27 (m, 4H), 2.91-2.84 (m, 4H), 1.48 (d, 6H).

Example 9: Preparation of 1-cyclopentyl-N-(5-(piperazin-1-yl)pyridin-2-yl)-4,5-dihydro-1H-pyrazolo[4,3H]quinazolin-8-amine (Compound P-9)

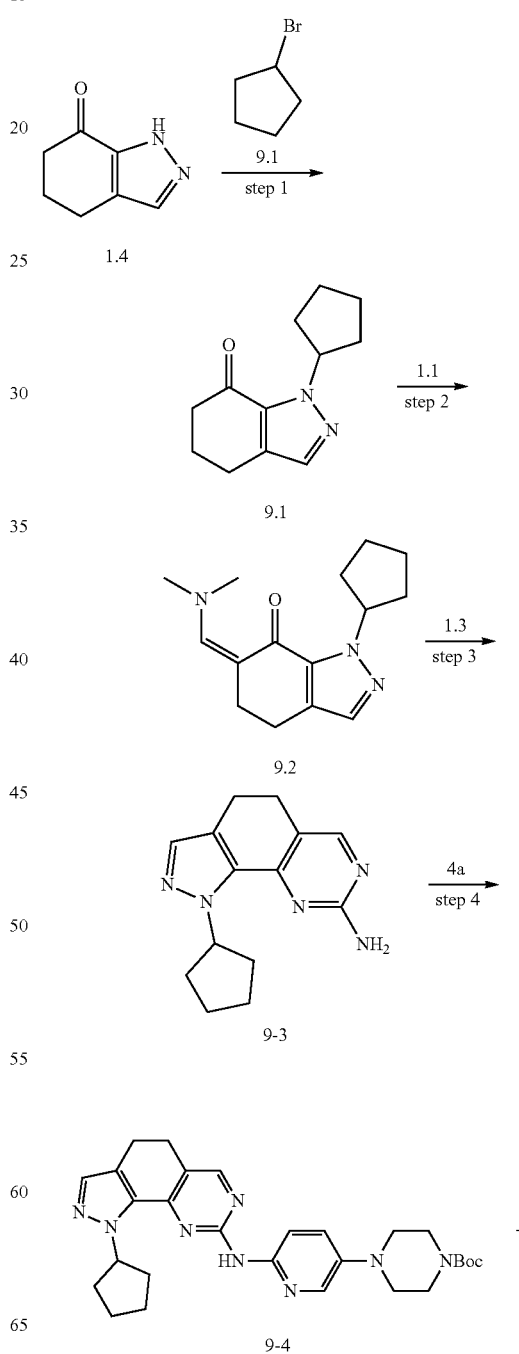

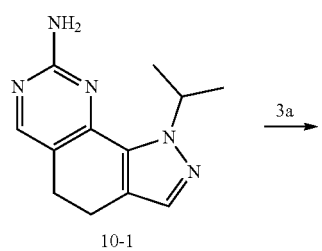

P-9 step 1: The preparation method was the same as the method for compound 3-5, except that compound 3-4 and 2-iodopropane in the method for 3-5 were replaced by compound 1-4 and 9.1. MS m/z (ESI): 205[M+H]$^+$.

step 2: The preparation method was the same as the method for compound 1-3, except that compound 1-2 in the method for 1-3 was replaced by compound 9-1. MS m/z (ESI): 260[M+H]$^+$.

step 3: The preparation method was the same as the method for compound 2-4, except that compound 2-3 in the method for 2-4 was replaced by compound 9-2. MS m/z (ESI): 256[M+H]$^+$.

step 4: The preparation method was the same as the method for compound 1-8, except that compound 1-7 in the method for 1-8 was replaced by compound 9-3. MS m/z (ESI): 517[M+H]$^+$.

step 5: The preparation method was the same as the method for compound P-1, except that compound 1-8 in the method for P-1 was replaced by compound 9-4. Compound P-9 (23 mg, 3%) as a white solid was obtained by purification through Prep-HPLC. MS m/z (ESI): 417[M+H]$^+$; $^1$H NMR (400 MHz, CDCl$_3$) 9.49 (s, 1H), 8.33 (s, 1H), 7.95-7.96 (d, 1H), 7.84-7.87 (d, 1H), 7.32-7.39 (m, 2H), 6.01-6.09 (m, 1H), 2.97-3.00 (t, 4H), 2.82-2.83 (d, 4H), 2.72-2.77 (t, 2H), 2.66-2.69 (t, 2H), 2.02 (s, 2H), 1.81-1.92 (m, 4H), 1.60-1.61 (d, 2H).

Example 10: Preparation of N-(5-((4-methylpiperazin-1-yl)methyl)pyridin-2-yl)-1-isopropyl-4,5-dihydro-1H-pyrazolo[4,3H]quinazolin-8-amine (Compound P-10)

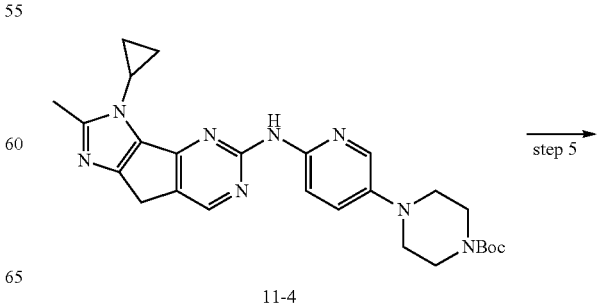

P-10

The preparation method was the same as the method for compound P-3, except that compound 3-7 in the method for P-3 was replaced by compound 10-1. Compound P-10 (10 mg, 11.6%) as a white solid was obtained by purification through Prep-HPLC. MS m/z (ESI): 433[M+H]$^+$; $^1$H NMR (400 MHz, CDCl$_3$) δ 9.77 (s, 1H), 8.39 (s, 1H), 8.14 (s, 1H), 8.02-8.04 (d, 1H), 7.62-7.64 (m, 1H), 7.42 (s, 1H), 5.90-5.97 (m, 1H), 3.40 (s, 2H), 2.77-2.79 (d, 2H), 2.69-2.71 (d, 2H) 2.25-2.31 (m, 10H), 1.39- 1.40 (d, 6H), 0.92-0.96 (t, 3H).

Example 11

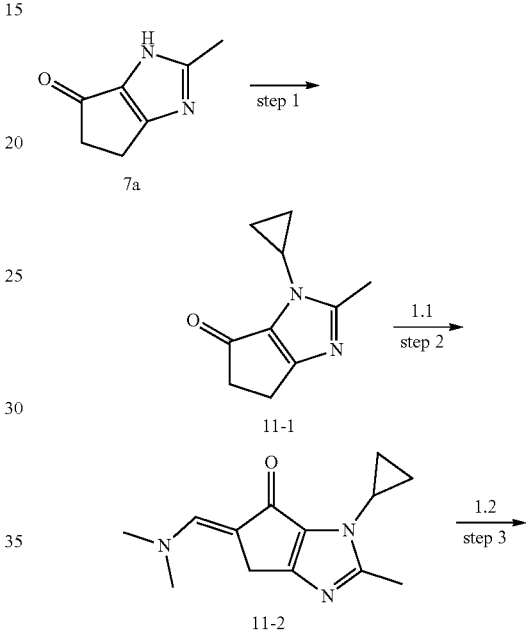

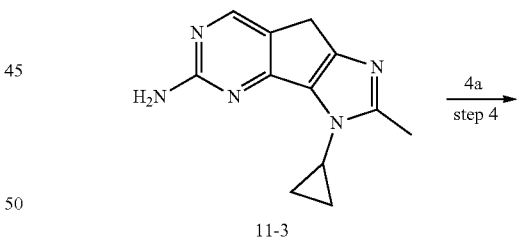

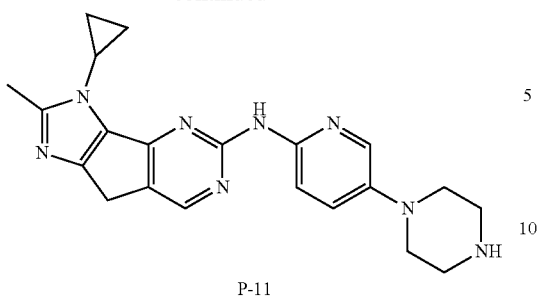

P-11

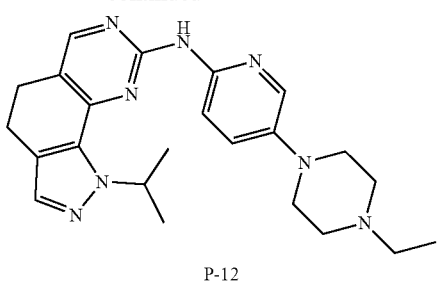

P-12 step 1: To a solution of compound 7a (400 mg, 3 mmol) in dichloroethane (30 mL) was added cyclopropylboronic acid (480 mg, 6 mmol), copper acetate (560 mg, 3 mmol), 2,2'-bipyridine (440 mg, 3 mmol) and potassium carbonate (800 mg, 6 mmol). The mixture was stirred at 70° C. for 4 hours. LC-MS was used to monitor the reaction until the reaction was complete. The reaction solution was concentrated and purified by combiflash (DCM:MeOH=20:1) to give 130 mg of compound 11-2. MS m/z (ESI): 177[M+H]$^+$.

step 2: The preparation method was the same as the method for compound 1-3, except that compound 1-2 in the method for 1-3 was replaced by compound 11-1. MS m/z (ESI): 231[M+H]$^+$.

step 3: The preparation method was the same as the method for compound 2-4, except that compound 2-3 in the method for 2-4 was replaced by compound 11-2. MS m/z (ESI): 228[M+H]$^+$.

step 4: The preparation method was the same as the method for compound 1-8, except that compound 1-7 in the method for 1-8 was replaced by compound 11-3. MS m/z (ESI): 489[M+H]$^+$.

step 5: The preparation method was the same as the method for compound P-1, except that compound 1-8 in the method for P-1 was replaced by compound 11-4. Compound P-11 (13 mg, 55%) as a white solid was obtained by purification through Prep-HPLC. MS m/z (ESI): 389[M+H]$^+$; $^1$H NMR (400 MHz, DMSO) δ 9.06 (s, 1H), 8.26 (d, 1H), 8.24 (s, 1H), 7.92 (d, 1H), 7.41 (dd, 1H), 3.49-3.39 (m, 1H), 3.38 (s, 2H), 3.02-2.96 (m, 4H), 2.86-2.76 (m, 4H), 2.50 (s, 3H), 1.29-1.15 (m, 4H).

Example 12: Preparation of N-(5-(4-methylpiperazin-1-yl)pyridin-2-yl)-1-isopropyl-4,5-dihydro-1H-pyrazolo[4,3H]quinazolin-8-amine (Compound P-12)

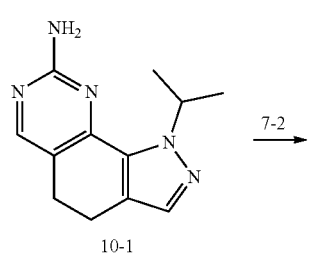

The preparation method was the same as the method for compound P-3, except that compound 3-7 and 3a in the method for P-3 were replaced by compound 10-1 and 7-2. Compound P-10 (5 mg, 6%) as a white solid was obtained by purification through Prep-HPLC. MS m/z (ESI): 419[M+H]$^+$; $^1$H NMR (400 MHz, CDCl$_3$) δ 9.44 (s, 1H), 8.33 (s, 1H), 7.96 (s, 1H), 7.88-7.90 (d, 1H), 7.38-7.41 (m, 2H), 5.87-5.94 (m, 1H), 3.08-3.11 (d, 4H), 2.75-2.77 (d, 2H), 2.48-2.50 (d, 4H), 2.34-2.38 (m, 2H), 1.38-1.40 (d, 6H), 0.99-1.02 (t, 3H).

Example 13

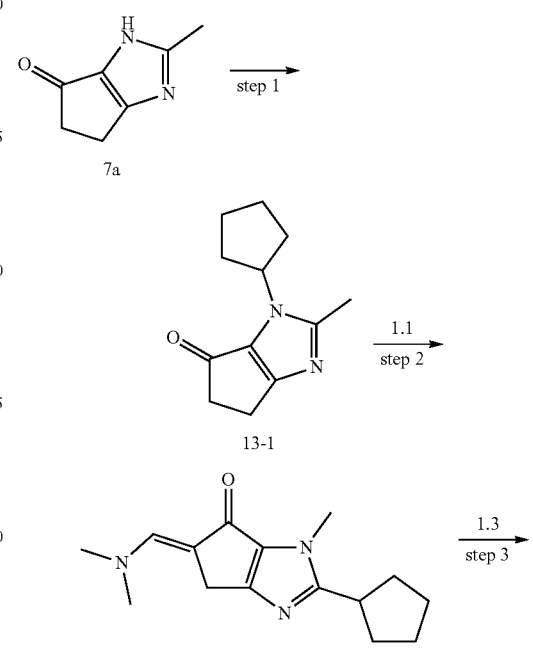

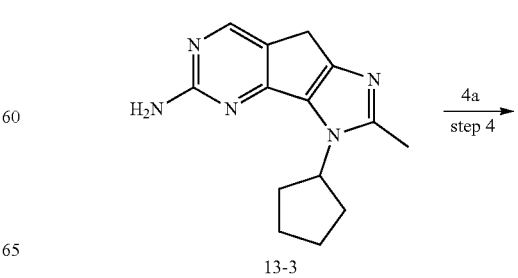

75
-continued

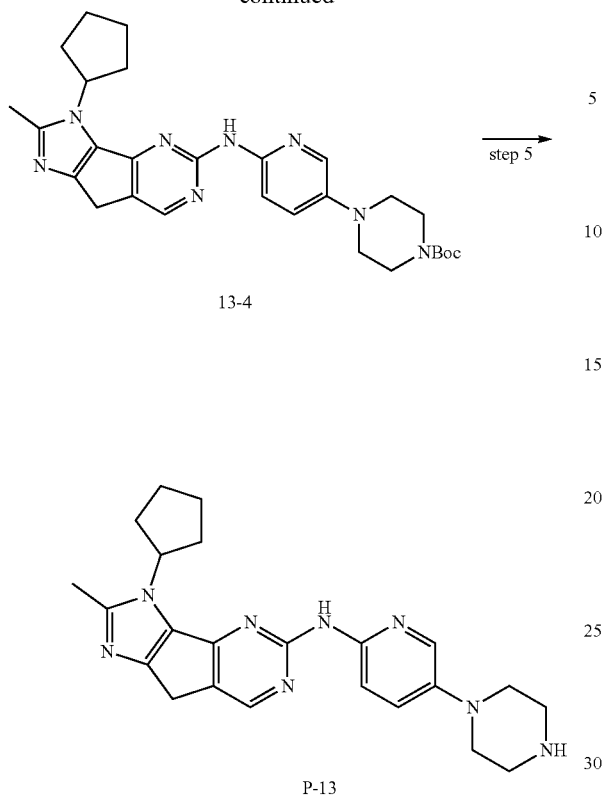

13-4

P-13 step 1: The preparation method was the same as the method for compound 3-5, except that compound 3-4 and 2-iodopropane in the method for 3-5 were replaced by compound 7a and bromopentane. MS m/z (ESI): 205[M+H]+.

step 2: The preparation method was the same as the method for compound 1-3, except that compound 1-2 in the method for 1-3 was replaced by compound 13-1. MS m/z (ESI): 260[M+H]+.

step 3: The preparation method was the same as the method for compound 2-4, except that compound 2-3 in the method for 2-4 was replaced by compound 13-2. MS m/z (ESI): 256[M+H]+.

step 4: The preparation method was the same as the method for compound 1-8, except that compound 1-7 in the method for 1-8 was replaced by compound 13-3. MS m/z (ESI): 517[M+H]+.

step 5: The preparation method was the same as the method for compound P-1, except that compound 1-8 in the method for P-1 was replaced by compound 13-4. Compound P-13 (313 mg, 64%) as a white solid was obtained by purification through Prep-HPLC. MS m/z (ESI): 417[M+H]+; $^1$H NMR (400 MHz, DMSO) δ 9.08 (s, 1H), 8.24 (s, 1H), 8.00-7.95 (m, 2H), 7.34 (dd, 1H), 4.61-4.55 (m, 1H), 3.41 (s, 2H), 3.00-2.98 (m, 4H), 2.84-2.83 (m, 4H), 2.48-2.47 (m, 3H), 2.25-2.22 (m, 2H), 2.01-1.97 (m, 5H), 1.66-1.64 (m, 2H).

76

Example 14: Preparation of 9-isopropyl-8-methyl-N-(5-(piperazin-1-yl)pyridin-2-yl)-6,8-dihydro-5H-pyrazolo[3,4-H]quinazolin-2-amine (Compound P-14)

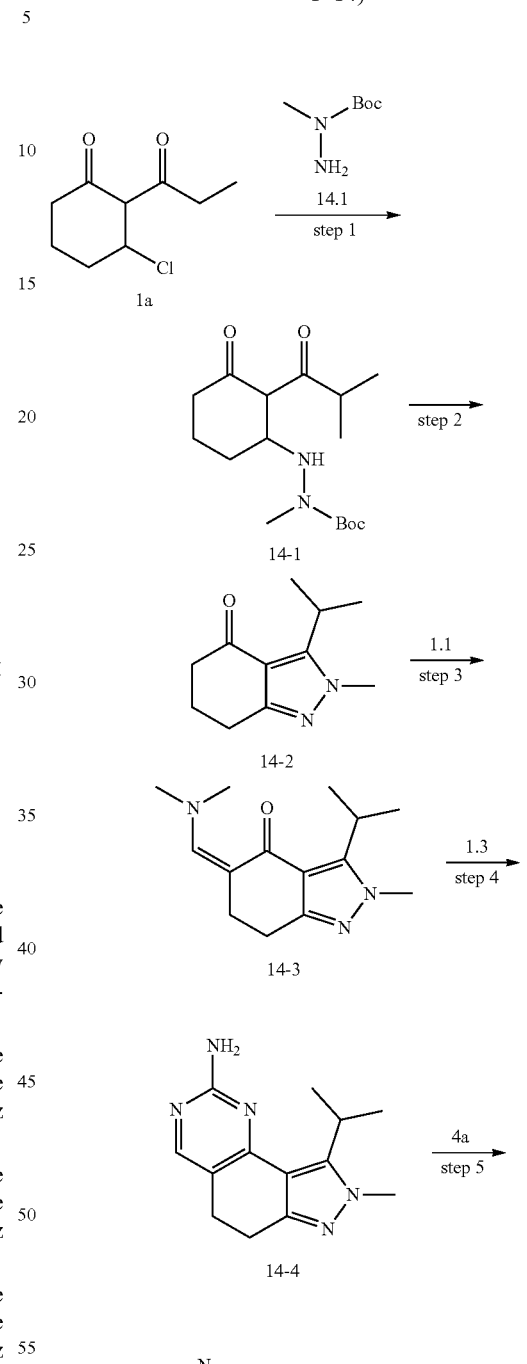

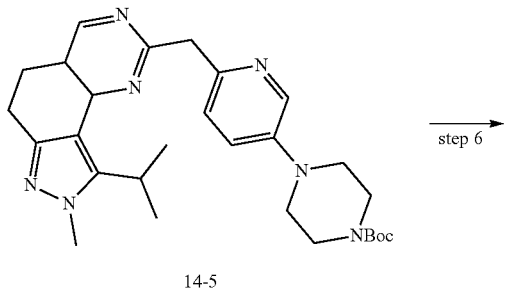

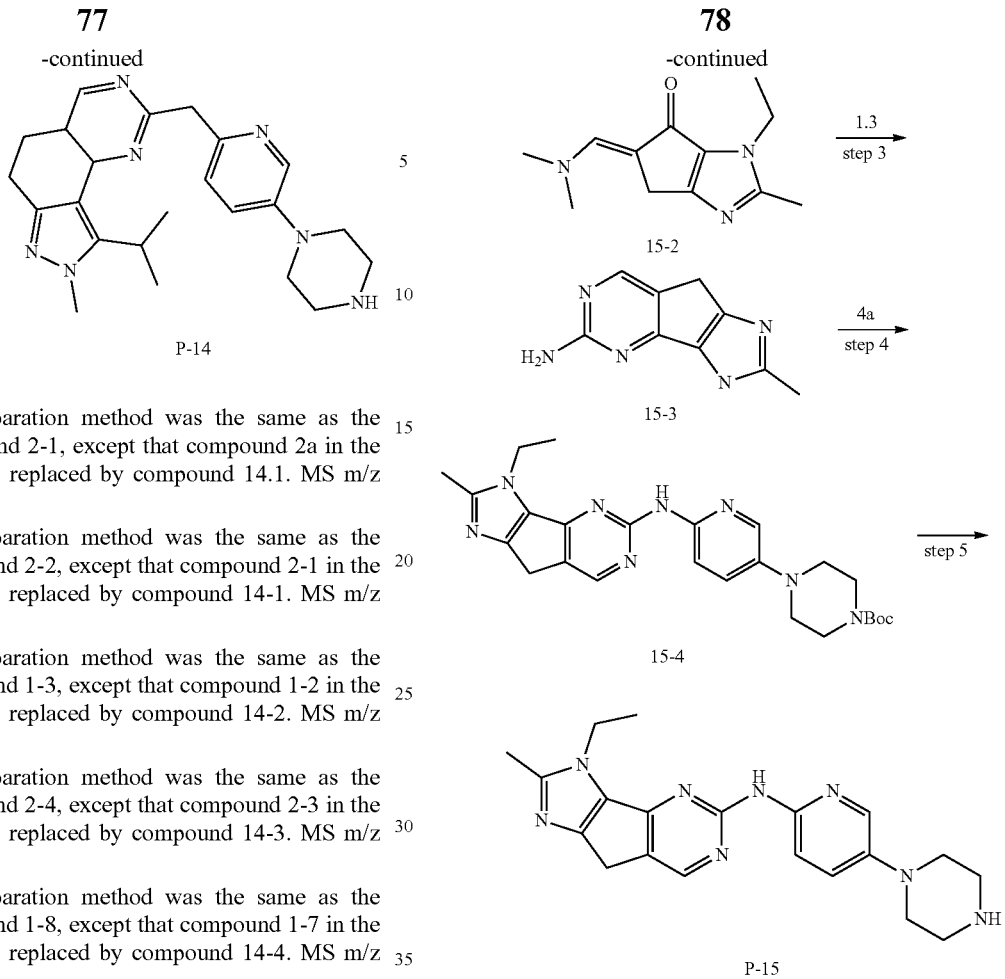

step 1: The preparation method was the same as the method for compound 2-1, except that compound 2a in the method for 2-1 was replaced by compound 14.1. MS m/z (ESI): 313[M+H]⁺.

step 2: The preparation method was the same as the method for compound 2-2, except that compound 2-1 in the method for 2-2 was replaced by compound 14-1. MS m/z (ESI): 193[M+H]⁺.

step 3: The preparation method was the same as the method for compound 1-3, except that compound 1-2 in the method for 1-3 was replaced by compound 14-2. MS m/z (ESI): 248[M+H]⁺.

step 4: The preparation method was the same as the method for compound 2-4, except that compound 2-3 in the method for 2-4 was replaced by compound 14-3. MS m/z (ESI): 244[M+H]⁺.

step 5: The preparation method was the same as the method for compound 1-8, except that compound 1-7 in the method for 1-8 was replaced by compound 14-4. MS m/z (ESI): 505[M+H]⁺.

step 6: The preparation method was the same as the method for compound P-1, except that compound 1-8 in the method for P-1 was replaced by compound 14-5. Compound P-14 (280 mg, 87%) as a white solid was obtained by purification through Prep-HPLC. MS m/z (ESI): 405[M+H]⁺; ¹H NMR (400 MHz, DMSO) δ 8.97 (s, 1H), 8.17 (s, 1H), 7.95 (d, 1H), 7.92 (d, 1H), 7.35 (dd, 1H), 3.99 (dt, 1H), 3.81 (s, 3H), 3.06-2.92 (m, 4H), 2.89-2.78 (m, 4H), 2.74 (t, 2H), 2.65 (t, 2H), 1.35 (d, 6H).

Example 15

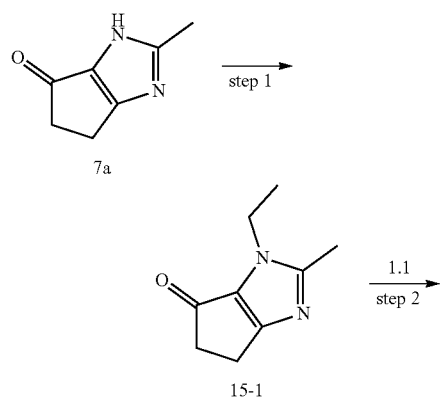

step 1: The preparation method was the same as the method for compound 3-5, except that compound 3-4 and 2-iodopropane in the method for 3-5 were replaced by compound 7a and iodoethane. MS m/z (ESI): 165[M+H]⁺.

step 2: The preparation method was the same as the method for compound 1-3, except that compound 1-2 in the method for 1-3 was replaced by compound 15-1. MS m/z (ESI): 219[M+H]⁺.

step 3: The preparation method was the same as the method for compound 2-4, except that compound 2-3 in the method for 2-4 was replaced by compound 15-2. MS m/z (ESI): 216[M+H]⁺.

step 4: The preparation method was the same as the method for compound 1-8, except that compound 1-7 in the method for 1-8 was replaced by compound 15-3. MS m/z (ESI): 477[M+H]⁺.

step 5: The preparation method was the same as the method for compound P-1, except that compound 1-8 in the method for P-1 was replaced by compound 15-4. Compound P-15 (19 mg, 50%) as a white solid was obtained by purification through Prep-HPLC. MS m/z (ESI): 377[M+H]⁺; ¹H NMR (400 MHz, DMSO) δ 9.07 (s, 1H), 8.24 (s, 1H), 8.16 (d, 1H), 7.93 (s, 1H), 7.39 (d, 1H), 4.20 (q, 2H), 3.41 (s, 2H), 3.05 (s, 4H), 2.91 (s, 4H), 2.44 (s, 3H), 1.46 (t, 3H).

Example 16

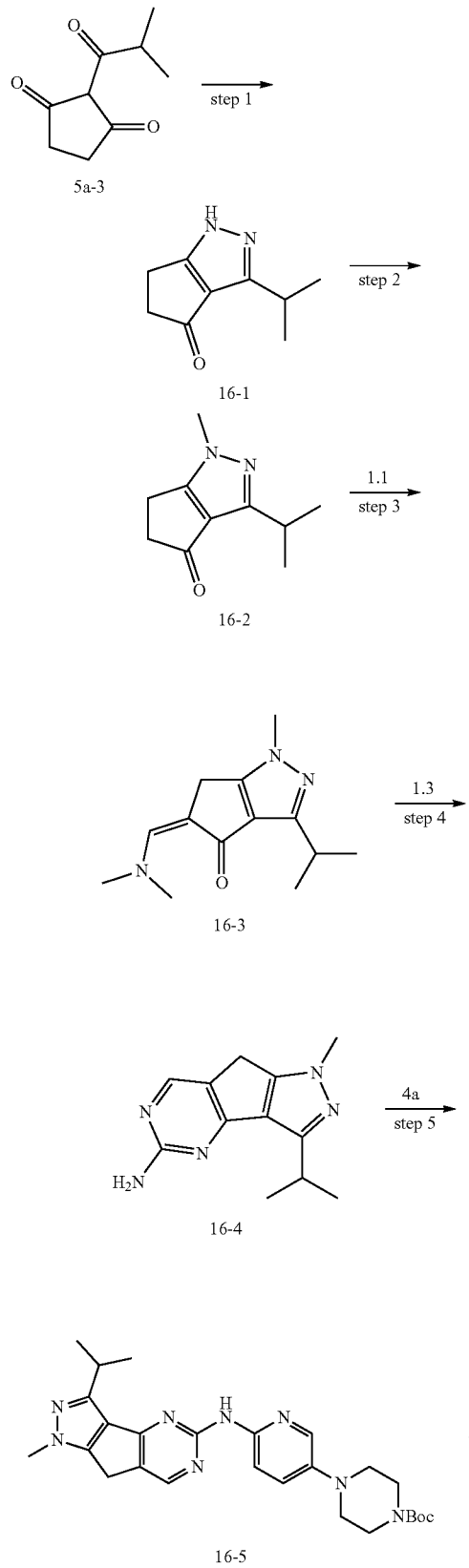

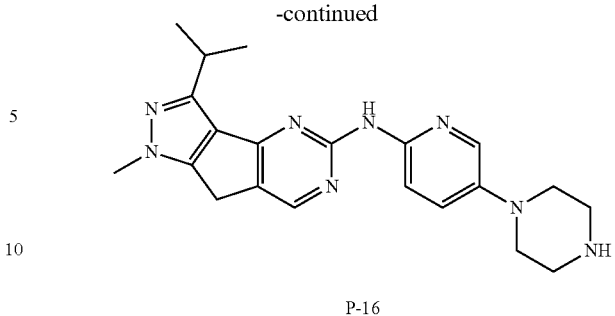

step 1: The preparation method was the same as the method for compound 1-4, except that compound 1-3 in the method for 1-4 was replaced by compound 5a-3. MS m/z (ESI): 165[M+H]).

step 2: The preparation method was the same as the method for compound 3-5, except that compound 3-4 and 2-iodopropane in the method for 3-5 were replaced by compound 16-1 and iodomethane. MS m/z (ESI): 179[M+H]$^+$.

step 3: The preparation method was the same as the method for compound 1-3, except that compound 1-2 in the method for 1-3 was replaced by compound 16-2. MS m/z (ESI): 234[M+H]$^+$.

step 4: The preparation method was the same as the method for compound 2-4, except that compound 2-3 in the method for 2-4 was replaced by compound 16-3. MS m/z (ESI): 230[M+H]$^+$.

step 5: The preparation method was the same as the method for compound 1-8, except that compound 1-7 in the method for 1-8 was replaced by compound 16-4. MS m/z (ESI): 491[M+H]$^+$.

step 6: The preparation method was the same as the method for compound P-1, except that compound 1-8 in the method for P-1 was replaced by compound 16-5. Compound P-16 (14 mg, 23%) as a white solid was obtained by purification through Prep-HPLC. MS m/z (ESI): 391[M+H]$^+$; $^1$H NMR (400 MHz, DMSO) δ 9.04 (s, 1H), 8.30 (s, 1H), 8.22 (d, 1H), 7.95 (s, 1H), 7.38 (d, 1H), 3.81 (s, 3H), 3.71 (s, 2H), 3.09-3.04 (m, 1H), 3.02-3.98 (m, 4H), 2.89-2.81 (m, 4H), 1.41 (d, 6H).

Example 17

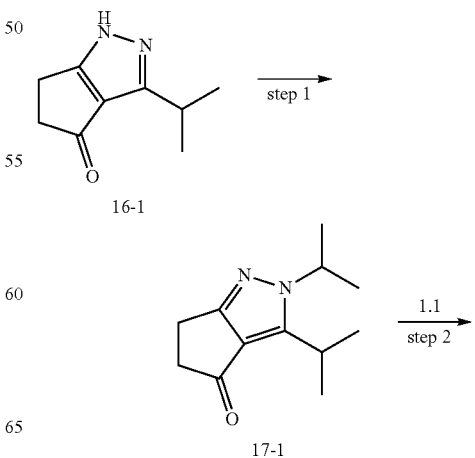

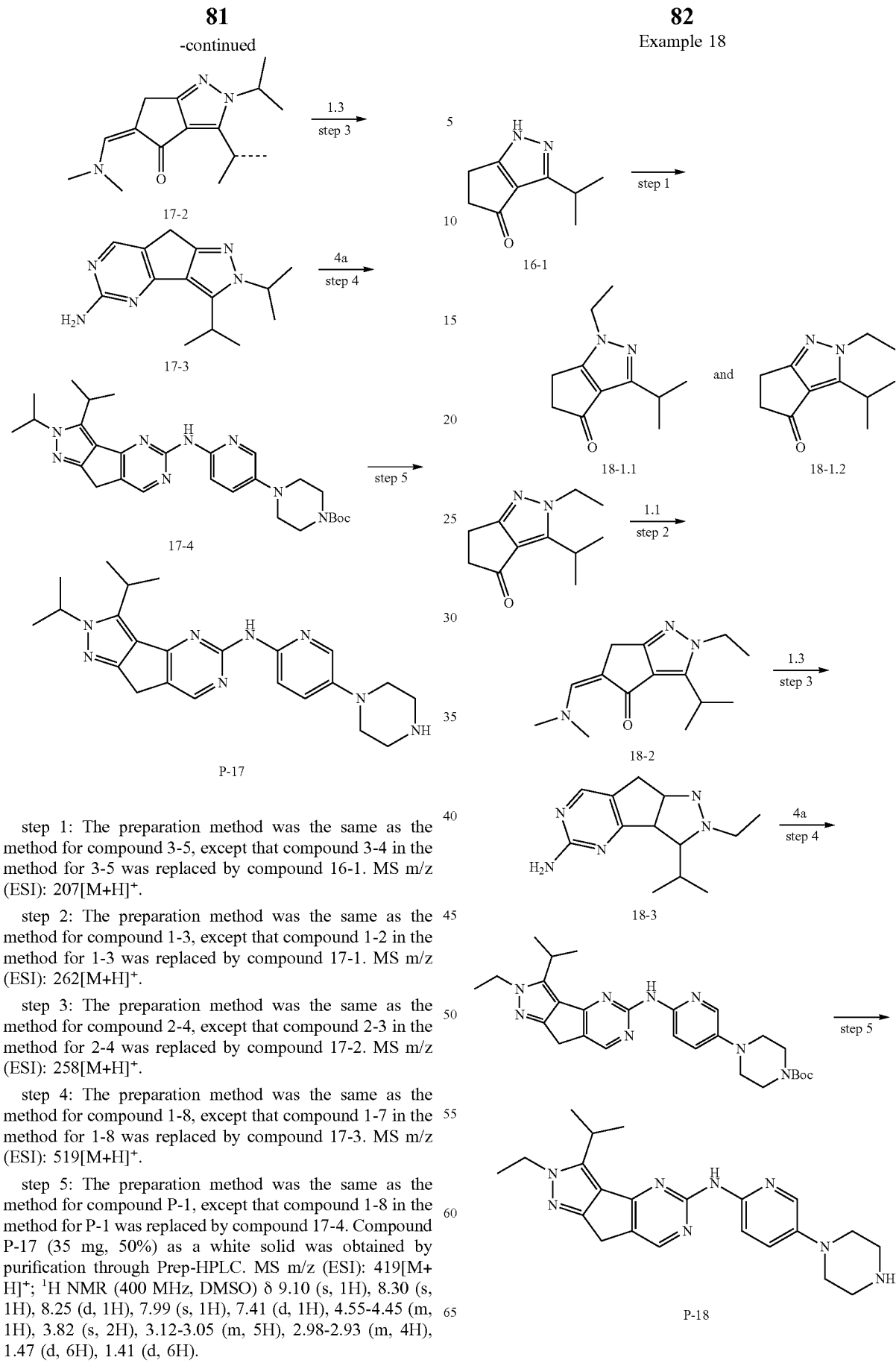

Example 18 step 1: The preparation method was the same as the method for compound 3-5, except that compound 3-4 in the method for 3-5 was replaced by compound 16-1. MS m/z (ESI): 207[M+H]⁺.

step 2: The preparation method was the same as the method for compound 1-3, except that compound 1-2 in the method for 1-3 was replaced by compound 17-1. MS m/z (ESI): 262[M+H]⁺.

step 3: The preparation method was the same as the method for compound 2-4, except that compound 2-3 in the method for 2-4 was replaced by compound 17-2. MS m/z (ESI): 258[M+H]⁺.

step 4: The preparation method was the same as the method for compound 1-8, except that compound 1-7 in the method for 1-8 was replaced by compound 17-3. MS m/z (ESI): 519[M+H]⁺.

step 5: The preparation method was the same as the method for compound P-1, except that compound 1-8 in the method for P-1 was replaced by compound 17-4. Compound P-17 (35 mg, 50%) as a white solid was obtained by purification through Prep-HPLC. MS m/z (ESI): 419[M+H]⁺; ¹H NMR (400 MHz, DMSO) δ 9.10 (s, 1H), 8.30 (s, 1H), 8.25 (d, 1H), 7.99 (s, 1H), 7.41 (d, 1H), 4.55-4.45 (m, 1H), 3.82 (s, 2H), 3.12-3.05 (m, 5H), 2.98-2.93 (m, 4H), 1.47 (d, 6H), 1.41 (d, 6H).

step 1: The preparation method was the same as the method for compound 3-5, except that compound 3-4 in the method for 3-5 was replaced by compound 16-1. MS m/z (ESI): 193[M+H]⁺.

step 2: The preparation method was the same as the method for compound 1-3, except that compound 1-2 in the method for 1-3 was replaced by compound 18-1.2. MS m/z (ESI): 248[M+H]⁺.

step 3: The preparation method was the same as the method for compound 2-4, except that compound 2-3 in the method for 2-4 was replaced by compound 18-2. MS m/z (ESI): 244[M+H]⁺.

step 4: The preparation method was the same as the method for compound 1-8, except that compound 1-7 in the method for 1-8 was replaced by compound 18-3. MS m/z (ESI): 505[M+H]⁺.

step 5: The preparation method was the same as the method for compound P-1, except that compound 1-8 in the method for P-1 was replaced by compound 18-4. Compound P-18 (30 mg, 50%) as a white solid was obtained by purification through Prep-HPLC. MS m/z (ESI): 405[M+H]⁺; ¹H NMR (400 MHz, DMSO) δ 9.17 (s, 1H), 8.34 (s, 1H), 8.23 (d, 1H), 7.99 (s, 1H), 7.41 (d, 1H), 4.23 (q, 2H), 3.61 (s, 2H), 3.31-3.27 (m, 1H), 3.13-3.07 (m, 4H), 2.99-2.94 (m, 4H), 1.49 (d, 6H), 1.37 (t, 3H).

Example 19

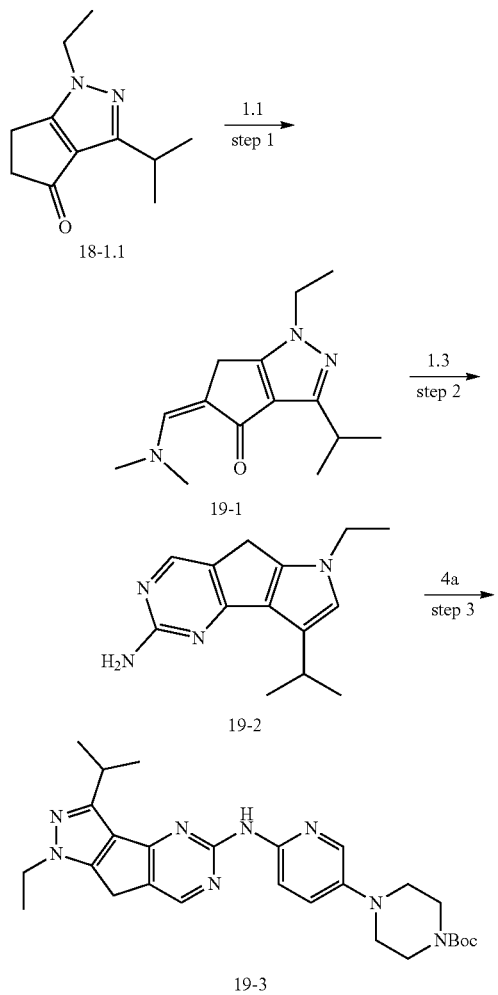

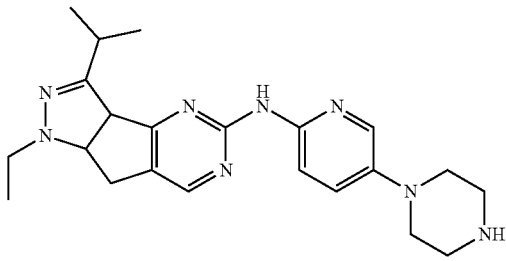

P-19 step 1: The preparation method was the same as the method for compound 1-3, except that compound 1-2 in the method for 1-3 was replaced by compound 18-1.1. MS m/z (ESI): 248[M+H]⁺.

step 2: The preparation method was the same as the method for compound 2-4, except that compound 2-3 in the method for 2-4 was replaced by compound 19-1. MS m/z (ESI): 244[M+H]⁺.

step 3: The preparation method was the same as the method for compound 1-8, except that compound 1-7 in the method for 1-8 was replaced by compound 19-2. MS m/z (ESI): 505[M+H]⁺.

step 4: The preparation method was the same as the method for compound P-1, except that compound 1-8 in the method for P-1 was replaced by compound 19-3. Compound P-19 (8 mg, 36%) as a white solid was obtained by purification through Prep-HPLC. MS m/z (ESI): 405[M+H]⁺; ¹H NMR (400 MHz, DMSO) δ 9.11 (s, 1H), 8.31 (s, 1H), 8.24 (d, 1H), 7.97 (s, 1H), 7.39 (d, 1H), 4.13 (q, 2H), 3.76 (s, 2H), 3.10-3.06 (m, 1H), 3.03-2.97 (m, 4H), 2.89-2.83 (m, 4H), 1.45-1.38 (m, 9H).

Example 20

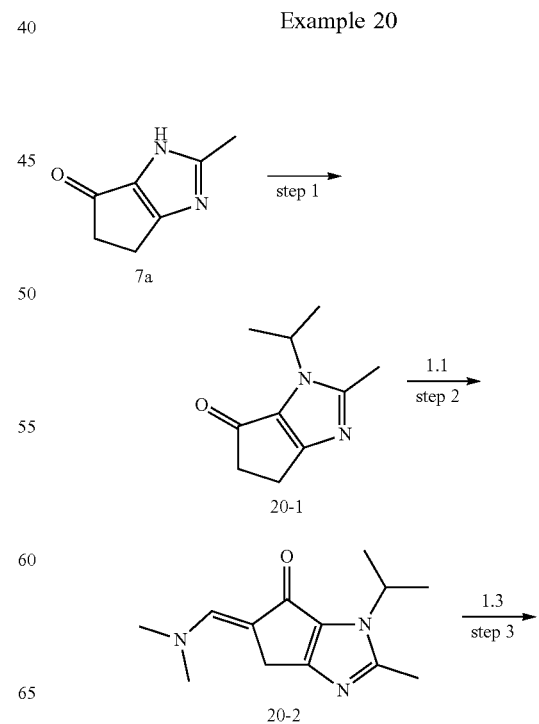

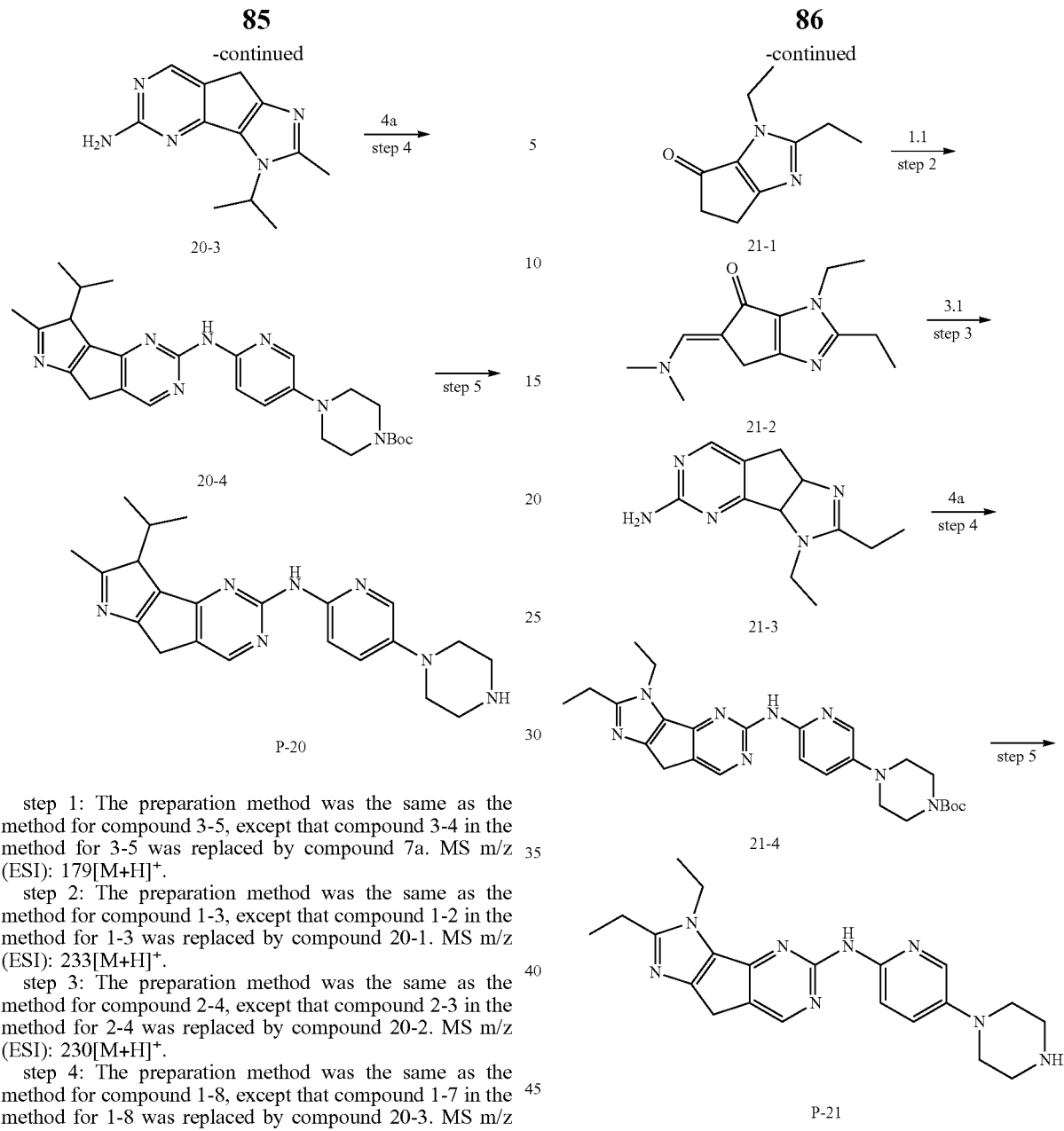

step 1: The preparation method was the same as the method for compound 3-5, except that compound 3-4 in the method for 3-5 was replaced by compound 7a. MS m/z (ESI): 179[M+H]⁺.

step 2: The preparation method was the same as the method for compound 1-3, except that compound 1-2 in the method for 1-3 was replaced by compound 20-1. MS m/z (ESI): 233[M+H]⁺.

step 3: The preparation method was the same as the method for compound 2-4, except that compound 2-3 in the method for 2-4 was replaced by compound 20-2. MS m/z (ESI): 230[M+H]⁺.

step 4: The preparation method was the same as the method for compound 1-8, except that compound 1-7 in the method for 1-8 was replaced by compound 20-3. MS m/z (ESI): 491[M+H]⁺.

step 5: The preparation method was the same as the method for compound P-1, except that compound 1-8 in the method for P-1 was replaced by compound 20-4. Compound P-20 (7 mg, 30%) as a white solid was obtained by purification through Prep-HPLC. MS m/z (ESI): 391[M+H]⁺; ¹H NMR (400 MHz, DMSO) δ 9.07 (s, 1H), 8.24 (s, 1H), 8.17 (d, 1H), 7.93 (s, 1H), 7.40 (d, 1H), 4.77-4.44 (m, 1H), 3.41 (s, 2H), 3.01 (s, 4H), 2.86 (s, 4H), 2.45 (s, 3H), 1.61 (d, 6H).

Example 21

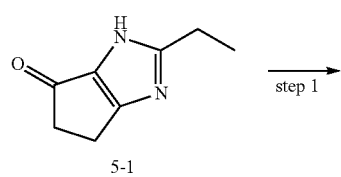

step 1: The preparation method was the same as the method for compound 3-5, except that compound 3-4 and 2-iodopropane in the method for 3-5 were replaced by compound 5-1 and 2-iodoethane. MS m/z (ESI): 179[M+H]⁺.

step 2: The preparation method was the same as the method for compound 1-3, except that compound 1-2 in the method for 1-3 was replaced by compound 21-1. MS m/z (ESI): 233[M+H]⁺.

step 3: The preparation method was the same as the method for compound 2-4, except that compound 2-3 in the method for 2-4 was replaced by compound 21-2. MS m/z (ESI): 230[M+H]⁺.

step 4: The preparation method was the same as the method for compound 1-8, except that compound 1-7 in the method for 1-8 was replaced by compound 21-3. MS m/z (ESI): 491[M+H]⁺.

step 5: The preparation method was the same as the method for compound P-1, except that compound 1-8 in the method for P-1 was replaced by compound 21-4. Compound P-21 (6.9 mg, 10%) as a white solid was obtained by purification through Prep-HPLC. MS m/z (ESI): 391[M+H]$^+$; $^1$H NMR (400 MHz, CDCl$_3$) δ 8.32 (d, 1H), 8.23 (s, 1H), 7.96 (d, 1H), 7.64 (s, 1H), 7.31 (dd, 1H), 4.24 (q, 2H), 3.48 (s, 2H), 3.11-3.05 (m, 8H), 2.83 (q, 1H), 1.62-1.55 (m, 3H), 1.41 (t, 3H).

Example 22

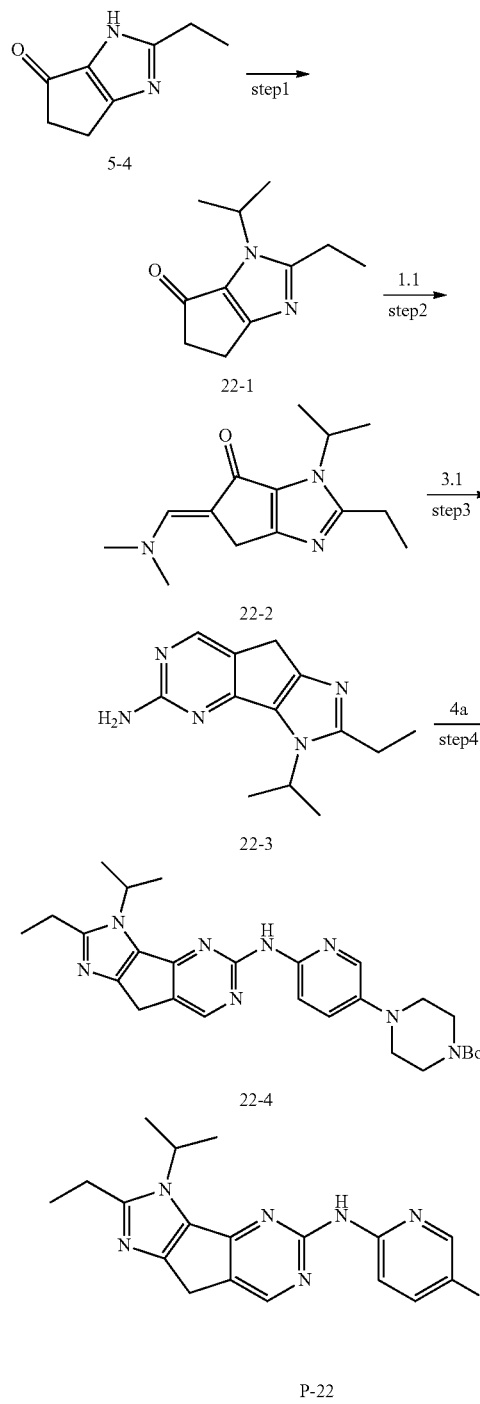

step 1: The preparation method was the same as the method for compound 3-5, except that compound 3-4 in the method for 3-5 was replaced by compound 5-4. MS m/z (ESI): 193[M+H]$^+$.

step 2: The preparation method was the same as the method for compound 1-3, except that compound 1-2 in the method for 1-3 was replaced by compound 22-1. MS m/z (ESI): 248[M+H]$^+$.

step 3: The preparation method was the same as the method for compound 2-4, except that compound 2-3 in the method for 2-4 was replaced by compound 22-2. MS m/z (ESI): 244[M+H]$^+$.

step 4: The preparation method was the same as the method for compound 1-8, except that compound 1-7 in the method for 1-8 was replaced by compound 22-3. MS m/z (ESI): 505[M+H]$^+$.

step 5: The preparation method was the same as the method for compound P-1, except that compound 1-8 in the method for P-1 was replaced by compound 22-4. Compound P-22 (180 mg, 45%) as a white solid was obtained by purification through Prep-HPLC. MS m/z (ESI): 405[M+H]$^+$; 1H NMR (400 MHz, DMSO) δ 9.10 (s, 1H), 8.31-8.11 (m, 2H), 7.93 (d, 1H), 7.39 (dd, 1H), 4.61 (t, 1H), 3.43 (s, 2H), 3.03-2.94 (m, 3H), 2.85-2.75 (m, 5H), 1.62 (d, 5H), 1.24 (t, 3H).

Example 23: Preparation of 2-ethyl-1-isopropyl-N-(5-(piperazin-1-yl)pyridin-2-yl)-4,5-dihydro-1H-imidazo[4,5-H]quinazolin-8-amine (Compound P-23)

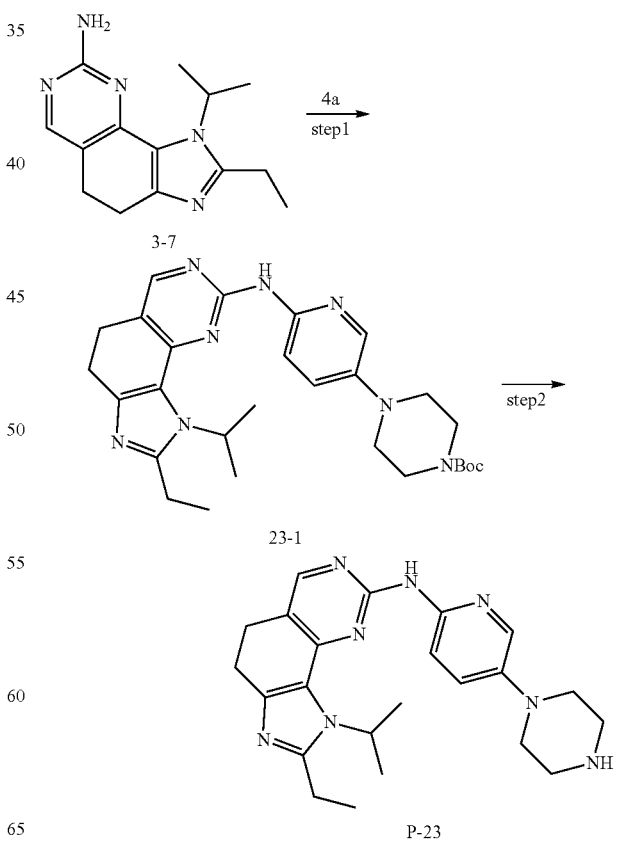

step 1: The preparation method was the same as the method for compound 1-8, except that compound 1-7 in the method for 1-8 was replaced by compound 3-7. MS m/z (ESI): 519[M+H]⁺.

step 2: The preparation method was the same as the method for compound P-1, except that compound 1-8 in the method for P-1 was replaced by compound 23-1. Compound P-23 (7 mg, 17%) as a white solid was obtained by purification through Prep-HPLC. MS m/z (ESI): 419[M+H]⁺; ¹H NMR (400 MHz, DMSO) δ 9.10 (s, 1H), 8.13 (s, 1H), 7.92 (d, 1H), 7.87 (d, 1H), 7.36 (dd, 1H), 5.69 (m, 1H), 3.01-2.95 (m, 4H), 2.83-2.80 (m, 4H), 2.77-2.73 (m, 4H), 2.64 (t, 2H), 1.49 (d, 6H), 1.24 (t, 3H).

Example 24: Preparation of 1-isopropyl-2-methyl-N-(5-(piperazin-1-yl)pyridin-2-yl)-4,5-dihydro-1H-imidazo[4,5-H]quinazolin-8-amine (Compound P-24)

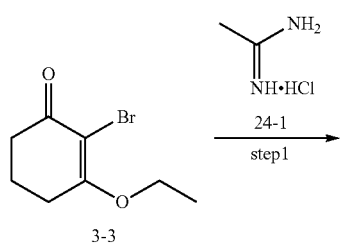

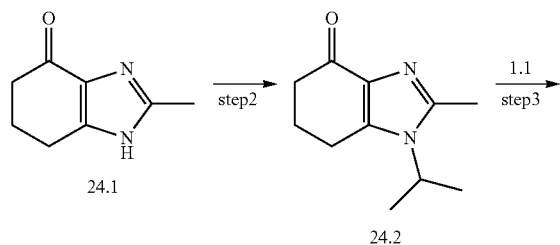

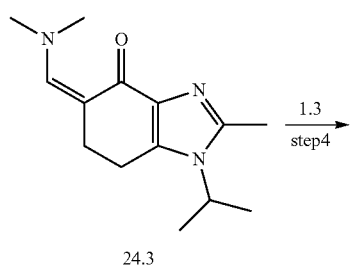

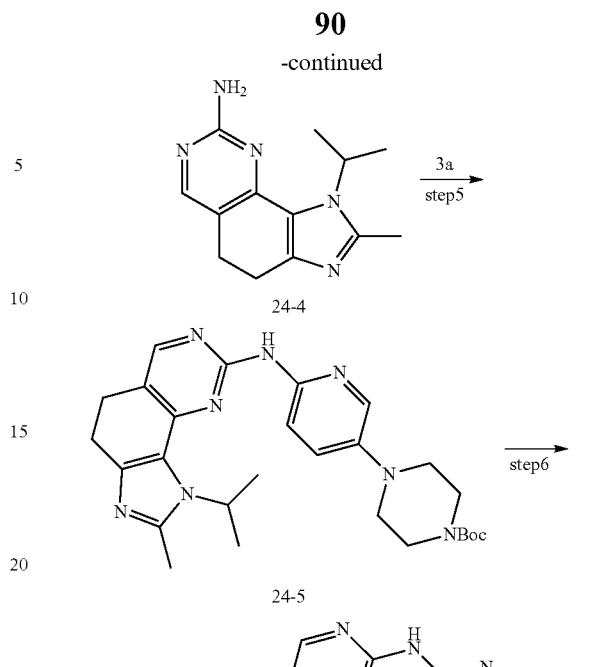

step 1: The preparation method was the same as the method for compound 3-4, except that compound 3.1 in the method for 3-4 was replaced by compound 24.1. MS m/z (ESI): 151[M+H]⁺.

step 2: The preparation method was the same as the method for compound 3-5, except that compound 3-4 in the method for 3-5 was replaced by compound 24-1. MS m/z (ESI): 193[M+H]⁺.

step 3: The preparation method was the same as the method for compound 1-3, except that compound 1-2 in the method for 1-3 was replaced by compound 24-2. MS m/z (ESI): 248[M+H]⁺.

step 4: The preparation method was the same as the method for compound 2-4, except that compound 2-3 in the method for 2-4 was replaced by compound 24-3. MS m/z (ESI): 244[M+H]⁺.

step 5: The preparation method was the same as the method for compound 1-8, except that compound 1-7 in the method for 1-8 was replaced by compound 24-4. MS m/z (ESI): 505[M+H]⁺.

step 6: The preparation method was the same as the method for compound P-1, except that compound 1-8 in the method for P-1 was replaced by compound 24-5. Compound P-24 (70 mg, 6%) as a white solid was obtained by purification through Prep-HPLC. MS m/z (ESI): 405[M+H]⁺; ¹H NMR (400 MHz, CDCl₃) 9.17 (s, 1H), 8.13 (s, 1H), 7.95-7.96 (d, 1H), 7.89-7.91 (d, 1H), 7.38-7.41 (m, 2H), 5.78 (s, 1H), 3.10-3.11 (d, 4H), 2.98-3.01 (d, 4H), 2.73-2.77 (t, 2H), 2.60-2.64 (t, 2H), 2.43 (s, 3H), 1.38-1.40 (d, 6H).

Example 25: Preparation of 1-isopropyl-N-(5-(piperazin-1-yl)pyridin-2-yl)-4,5-dihydro-1H-pyrazolo[4,3H]quinazolin-8-amine (Compound P-25)

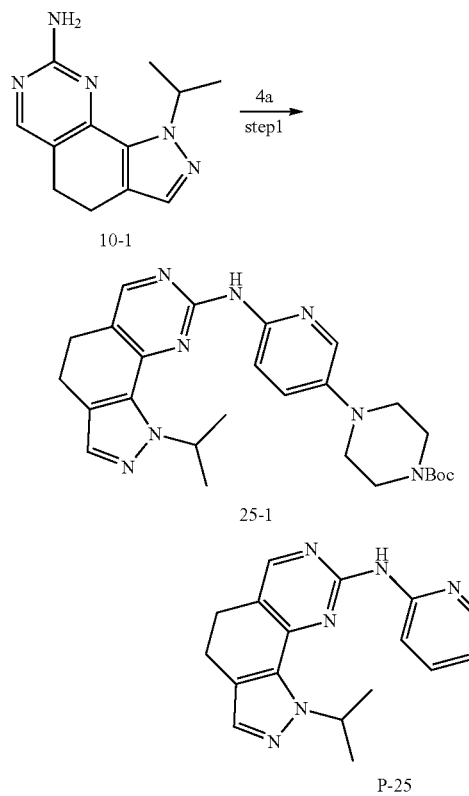

step 1: The preparation method was the same as the method for compound 1-8, except that compound 1-7 in the method for 1-8 was replaced by compound 10-1. MS m/z (ESI): 491[M+H]$^+$.

step 2: The preparation method was the same as the method for compound P-1, except that compound 1-8 in the method for P-1 was replaced by compound 25-1. Compound P-25 (580 mg, 58%) as a white solid was obtained by purification through Prep-HPLC. MS m/z (ESI): 391[M+H]$^+$; $^1$H NMR (400 MHz, CDCl$_3$) δ 8.31 (s, 1H), 8.17 (d, 1H), 8.02 (d, 1H), 7.98 (s, 1H), 7.41 (s, 1H), 7.29 (dd, 1H), 5.91-5.87 (m, 1H), 3.13-3.06 (m, 8H), 2.84-2.76 (m, 4H), 1.55 (d, 6H).

Example 26

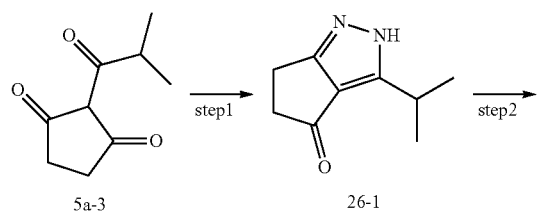

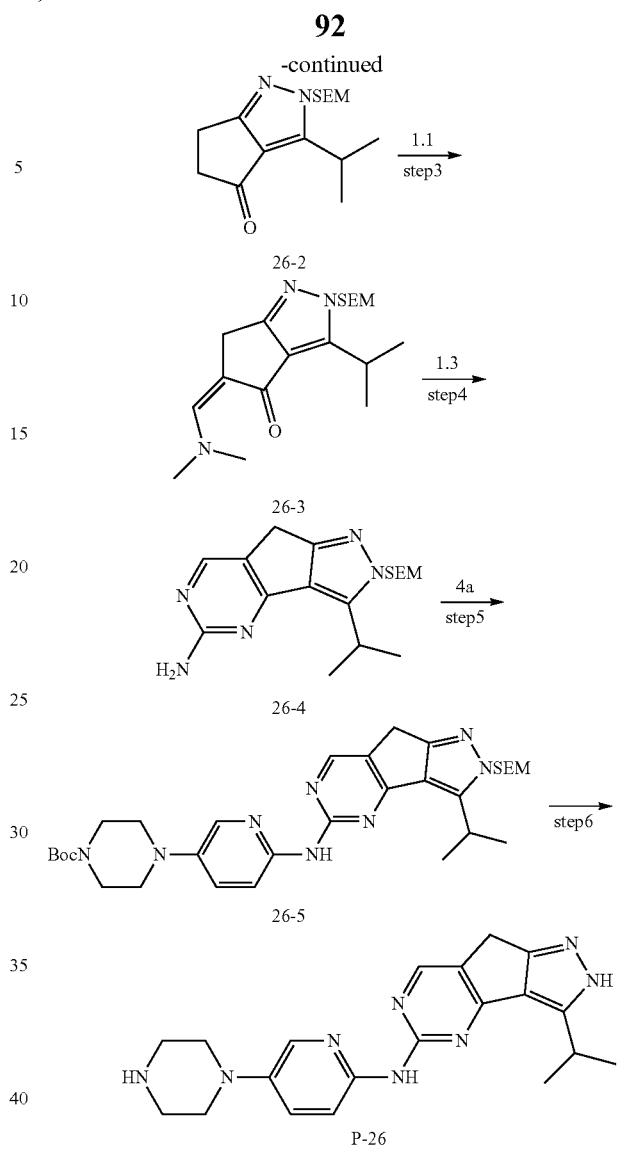

step 1: The preparation method was the same as the method for compound 1-4, except that compound 1-3 in the method for 1-4 was replaced by compound 5a-3. MS m/z (ESI): 165[M+H]$^+$.

step 2: The preparation method was the same as the method for compound 3-5, except that compound 3-4 and 2-iodomethane in the method for 3-5 were replaced by compound 26-1 and SEM-Cl. MS m/z (ESI): 295[M+H]$^+$.

step 3: The preparation method was the same as the method for compound 1-3, except that compound 1-2 in the method for 1-3 was replaced by compound 26-2. MS m/z (ESI): 350[M+H]$^+$.

step 4: The preparation method was the same as the method for compound 2-4, except that compound 2-3 in the method for 2-4 was replaced by compound 26-3. MS m/z (ESI): 346[M+H]$^+$.

step 5: The preparation method was the same as the method for compound 1-8, except that compound 1-7 in the method for 1-8 was replaced by compound 26-4. MS m/z (ESI): 607[M+H]$^+$.

step 6: The preparation method was the same as the method for compound P-1, except that compound 1-8 in the method for P-1 was replaced by compound 26-5. Compound P-25 (15 mg, 24%) as a white solid was obtained by purification through Prep-HPLC. MS m/z (ESI): 377[M+H]⁺; ¹H NMR (400 MHz, DMSO) δ 9.02 (s, 2H), 8.44 (s, 1H), 8.02 (s, 1H), 7.90 (d, 1H), 7.51 (d, 1H), 3.84 (s, 2H), 3.40-3.30 (m, 9H), 1.45-1.38 (m, 6H).

Example 27

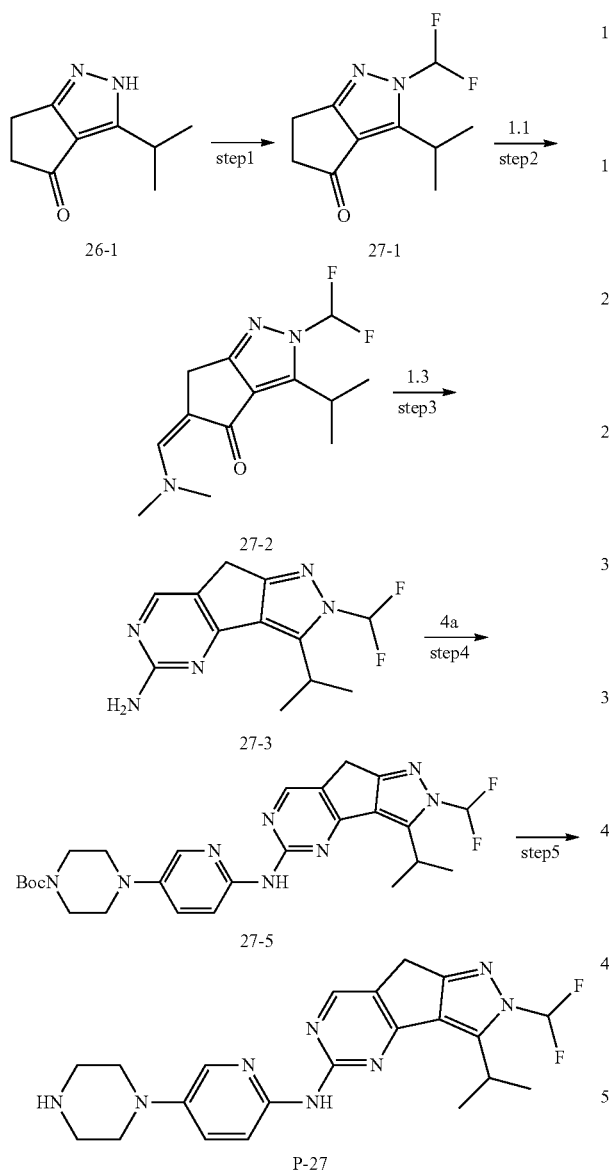

step 1: The preparation method was the same as the method for compound 3-5, except that compound 3-4 and 2-iodopropane in the method for compound 3-5 were replaced by compound 26-1 and sodium difluoromonochloroacetate. MS m/z (ESI): 215[M+H]⁺.

step 2: The preparation method was the same as the method for compound 1-3, except that compound 1-2 in the method for compound 1-3 was replaced by compound 27-1. MS m/z (ESI): 270[M+H]⁺.

step 3: The preparation method was the same as the method for compound 2-4, except that compound 2-3 in the method for compound 2-4 was replaced by compound 27-2. MS m/z (ESI): 266[M+H]⁺.

step 4: The preparation method was the same as the method for compound 1-8, except that compound 1-7 in the method for compound 1-8 was replaced by compound 27-3. MS m/z (ESI): 527[M+H]⁺.

step 5: The preparation method was the same as the method for compound P-1, except that compound 1-8 in the method for compound P-1 was replaced by compound 27-4. Compound P-27 (15 mg, 22%) as a white solid was obtained by purification through Prep-HPLC. MS m/z (ESI): 427[M+H]⁺; ¹H NMR (400 MHz, DMSO) δ 11.16 (s, 1H), 9.07 (s, 2H), 8.60 (s, 1H), 8.21-8.02 (m, 2H), 7.94 (d, 1H), 7.80 (d, 1H), 3.89 (s, 2H), 3.57-3.52 (m, 1H), 3.40-3.34 (m, 4H), 3.33-3.28 (m, 4H), 1.53 (d, 6H).

Example 28

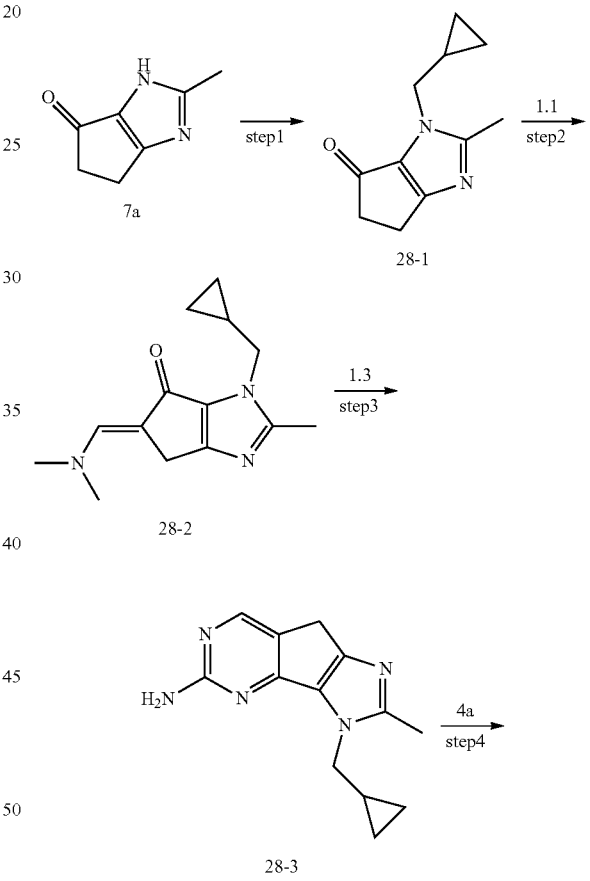

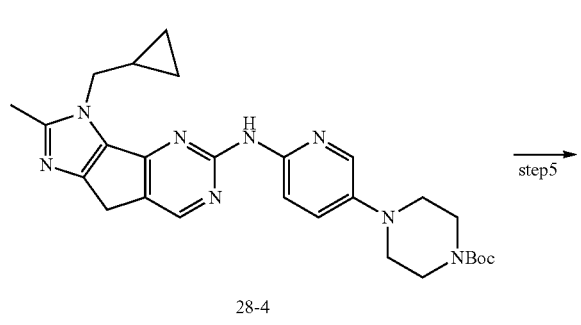

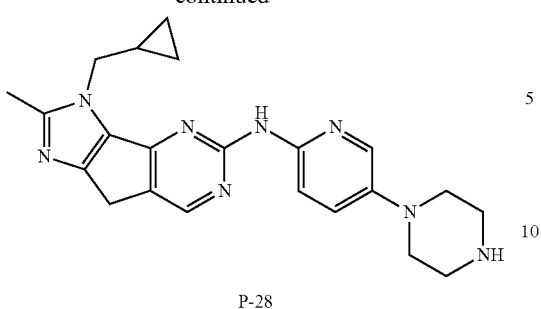

P-28 step 1: The preparation method was the same as the method for compound 3-5, except that compound 3-4 and 2-iodopropane in the method for compound 3-5 were replaced by compound 7a and bromomethyl cyclopropane. MS m/z (ESI): 191[M+H]⁺.

step 2: The preparation method was the same as the method for compound 1-3, except that compound 1-2 in the method for compound 1-3 was replaced by compound 28-1. MS m/z (ESI): 246[M+H]⁺.

step 3: The preparation method was the same as the method for compound 2-4, except that compound 2-3 in the method for compound 2-4 was replaced by compound 28-2. MS m/z (ESI): 242[M+H]⁺.

step 4: The preparation method was the same as the method for compound 1-8, except that compound 1-7 in the method for compound 1-8 was replaced by compound 28-3. MS m/z (ESI): 503[M+H]⁺.

step 5: The preparation method was the same as the method for compound P-1, except that compound 1-8 in the method for compound P-1 was replaced by compound 28-4. Compound P-28 (6 mg, 16%) as a white solid was obtained by purification through Prep-HPLC. MS m/z (ESI): 403[M+H]⁺. ¹H NMR (400 MHz, DMSO) δ 9.14 (s, 1H), 8.26 (s, 1H), 8.11 (d, 1H), 7.95 (d, 1H), 7.38 (dd, 1H), 4.07 (d, 2H), 3.43 (s, 2H), 3.05 (s, 4H), 2.92 (s, 4H), 2.50 (s, 3H), 1.44 (d, 1H), 0.49 (d, 4H).

Example 29: Preparation of 9-isopropyl-N-(5-(piperazin-1-yl)pyridin-2-yl)-6,8-dihydro-5H-pyrazolo[3,4-H]quinazolin-2-amine (Compound P-29)

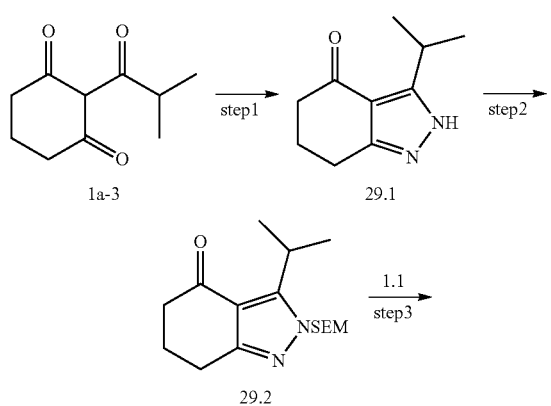

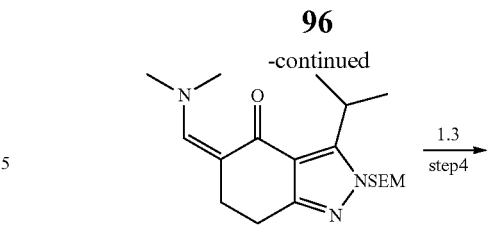

29.3

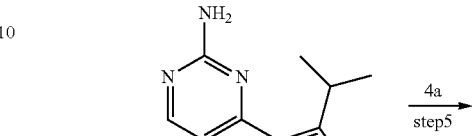

29-4

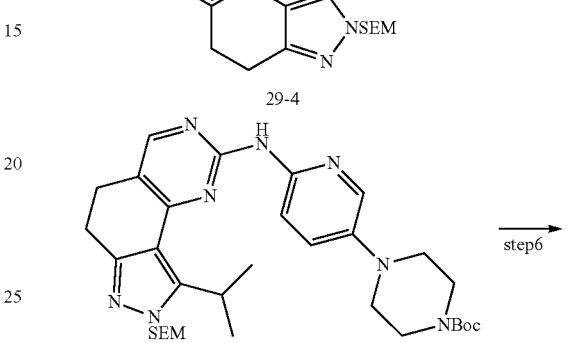

29-5

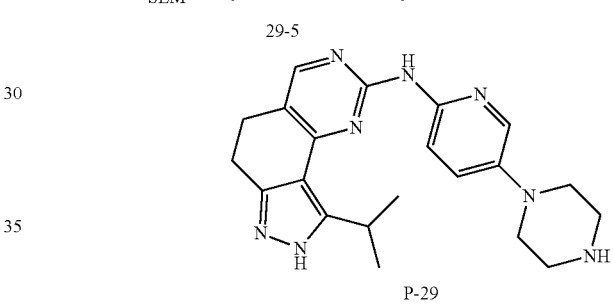

P-29 step 1: The preparation method was the same as the method for compound 14-1, except that compounds 1a and 14.1 in the method for compound 14-1 were replaced by compound 1a-3 and hydrazine hydrate. MS m/z (ESI): 179[M+H]⁺.

step 2: The preparation method was the same as the method for compound 3-5, except that compound 3-4 and 2-iodomethane in the method for compound 3-5 were replaced by compound 29-1 and SEM-Cl. MS m/z (ESI): 309[M+H]⁺.

step 3: The preparation method was the same as the method for compound 1-3, except that compound 1-2 in the method for compound 1-3 was replaced by compound 29-2. MS m/z (ESI): 364[M+H]⁺.

step 4: The preparation method was the same as the method for compound 2-4, except that compound 2-3 in the method for compound 2-4 was replaced by compound 29-3. MS m/z (ESI): 360[M+H]⁺.

step 5: The preparation method was the same as the method for compound 1-8, except that compound 1-7 in the method for compound 1-8 was replaced by compound 29-4. MS m/z (ESI): 621 [M+H]⁺.

step 6: The preparation method was the same as the method for compound P-1, except that compound 1-8 in the method for compound P-1 was replaced by compound 29-5. Compound P-29 (48 mg, 54.5%) as a white solid was obtained by purification through Prep-HPLC. MS m/z (ESI): 391[M+H]⁺; ¹H NMR (400 MHz, CDCl₃) 512.76 (s, 1H), 9.47 (s, 1H), 8.75 (s, 2H), 8.19 (s, 1H), 8.10 (s, 1H), 7.98-7.99 (d, 2H), 7.50-7.52 (d, 1H), 3.82-3.84 (d, 1H), 3.25-3.28 (d, 8H), 2.75-2.81 (m, 4H), 1.26-1.29 (d, 6H).

Example 30

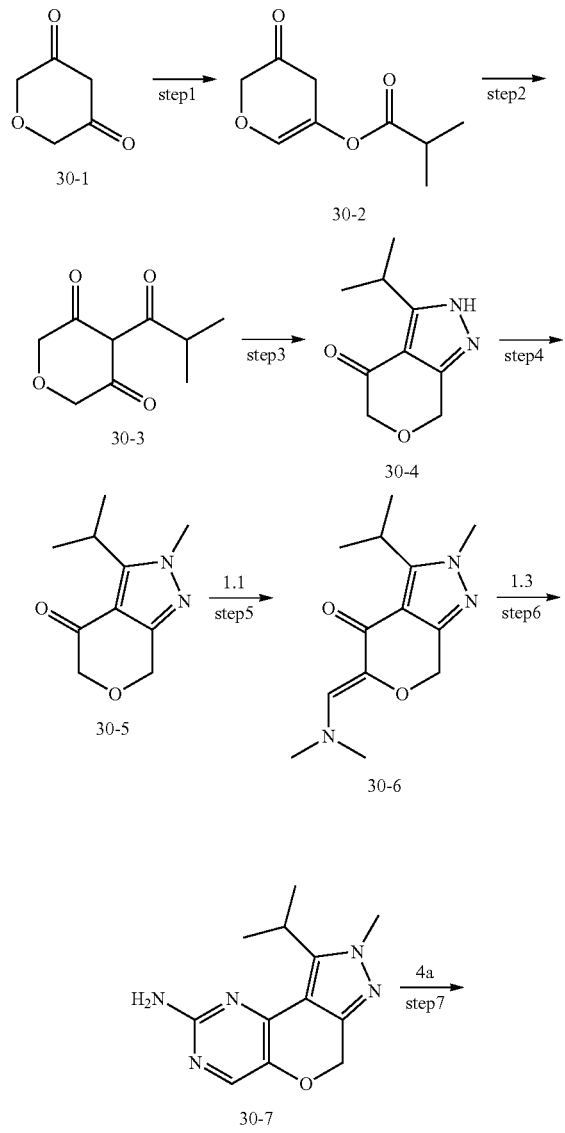

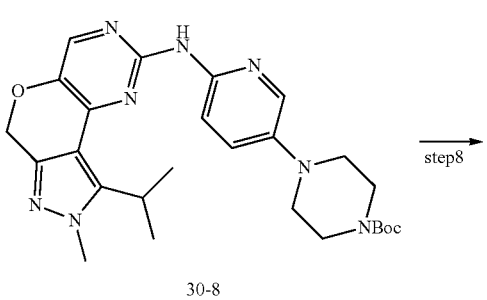

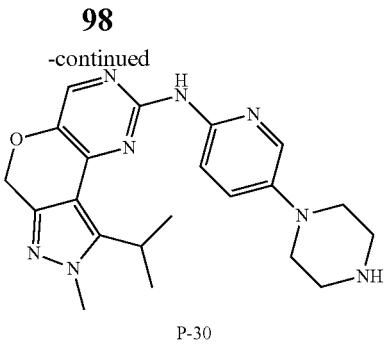

step 1: The preparation method was the same as the method for compound 1a-2, except that compound 1a-1 in the method for compound 1a-2 was replaced by compound 30-1. MS m/z (ESI): 185[M+H]+.

step 2: The preparation method was the same as the method for compound 1a-3, except that compound 1a-2 in the method for compound 1a-3 was replaced by compound 30-2. MS m/z (ESI): 184.9 [M+H]+.

step 3: The preparation method was the same as the method for compound 1-4, except that compound 1-3 in the method for compound 1-4 was replaced by compound 30-3. MS m/z (ESI): 181[M+H]+.

step 4: The preparation method was the same as the method for compound 3-5, except that compound 3-4 and 2-iodopropane in the method for compound 3-5 were replaced by compound 30-4 and iodomethane. MS m/z (ESI): 195[M+H]+.

step 5: The preparation method was the same as the method for compound 1-3, except that compound 1-2 in the method for compound 1-3 was replaced by compound 30-5. MS m/z (ESI): 250[M+H]+.

step 6: The preparation method was the same as the method for compound 2-4, except that compound 2-3 in the method for compound 2-4 was replaced by compound 30-6. MS m/z (ESI): 246[M+H]+.

step 7: The preparation method was the same as the method for compound 1-8, except that compound 1-7 in the method for compound 1-8 was replaced by compound 30-7. MS m/z (ESI): 507[M+H]+.

step 8: The preparation method was the same as the method for compound P-1, except that compound 1-8 in the method for compound P-1 was replaced by compound 30-8. Compound P-30 (6.6 mg, 19%) as a white solid was obtained by purification through Prep-HPLC. MS m/z (ESI): 407 [M+H]+; 1H NMR (400 MHz, CDCl3) δ 8.21 (d, 1H), 8.04 (s, 1H), 7.95 (s, 1H), 7.53 (s, 1H), 7.27 (dd, 1H), 5.15 (s, 2H), 3.89 (s, 3H), 3.62-3.58 (m, 1H), 3.08 (d, 8H), 1.49 (d, 6H).

Example 31

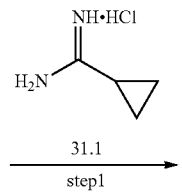

-continued

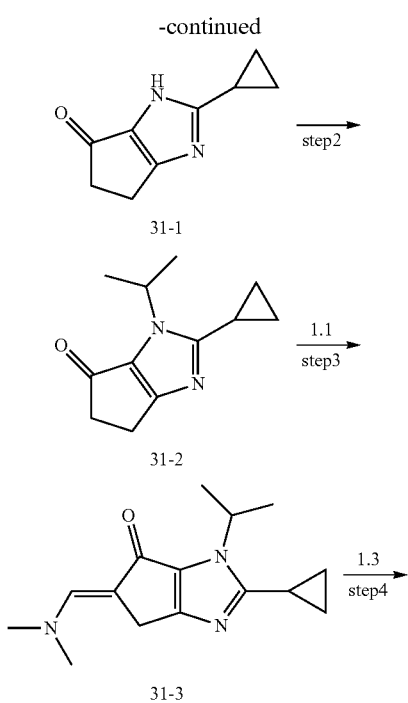

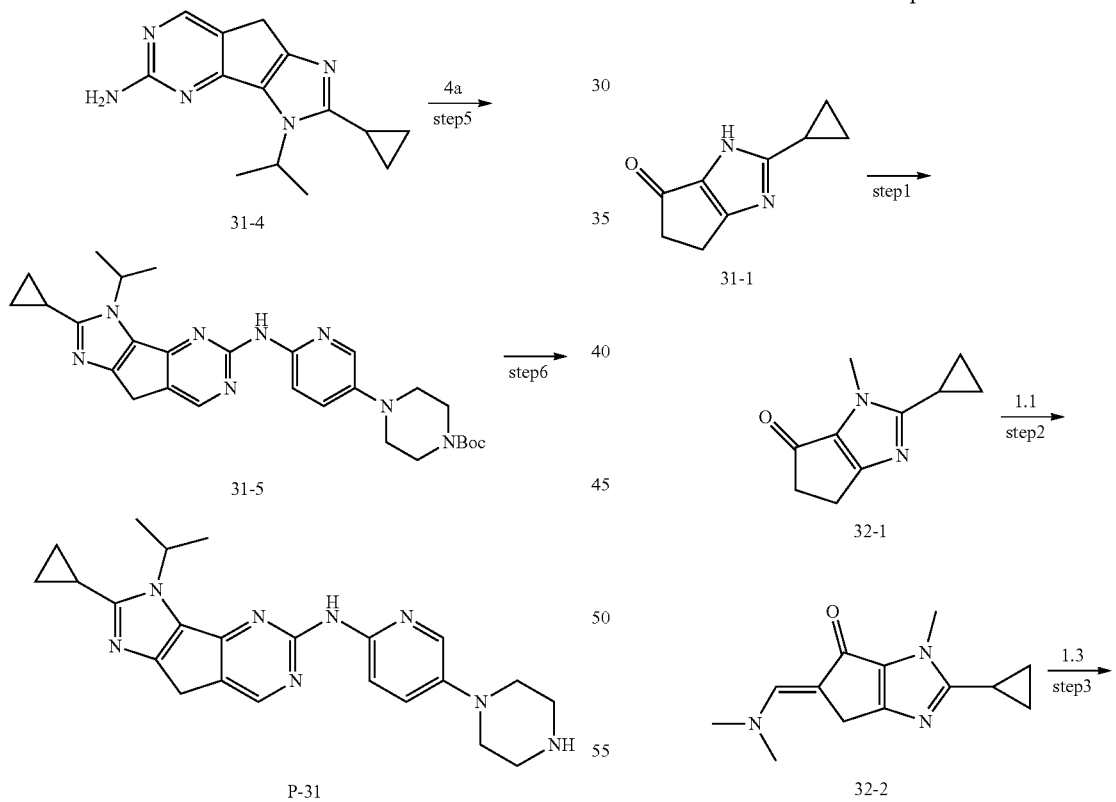

step 1: The preparation method was the same as the method for compound 3-4, except that compounds 3-3 and 3.1 in the method for compound 3-4 were replaced by compounds 6a and 31.1. MS m/z (ESI): 163[M+H]$^+$.

step 2: The preparation method was the same as the method for compound 3-5, except that compound 3-4 in the method for compound 3-5 was replaced by compound 31-1. MS m/z (ESI): 205[M+H]$^+$.

step 3: The preparation method was the same as the method for compound 3-6, except that compound 3-5 in the method for compound 3-6 was replaced by compound 31-2. MS m/z (ESI): 259 [M+H]$^+$.

step 4: The preparation method was the same as the method for compound 3-7, except that compound 3-6 in the method for compound 3-7 was replaced by compound 31-3. MS m/z (ESI): 256[M+H]$^+$.

step 5: The preparation method was the same as the method for compound 1-8, except that compound 1-7 in the method for compound 1-8 was replaced by compound 31-4. MS m/z (ESI): 517[M+H]$^+$.

step 6: The preparation method was the same as the method for compound P-1, except that compound 1-8 in the method for compound P-1 was replaced by compound 31-5. Compound P-31 (7 mg, 19%) as a white solid was obtained by purification through Prep-HPLC. MS m/z (ESI): 417[M+H]$^+$. $^1$H NMR (400 MHz, DMSO) δ 9.05 (s, 1H), 8.23 (s, 1H), 8.17 (d, 1H), 7.94 (s, 1H), 7.41 (d, 1H), 4.94-4.84 (m, 1H), 3.39 (s, 2H), 3.08-2.99 (m, 4H), 2.91-2.82 (m, 4H), 2.21-2.15 (m, 1H), 1.65 (d, 6H), 1.00-0.95 (m, 2H), 0.94-0.92 (m, 2H).

Example 32

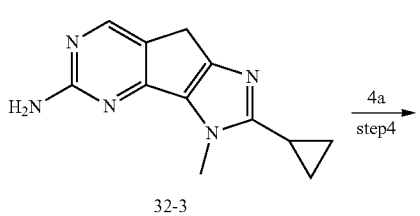

-continued

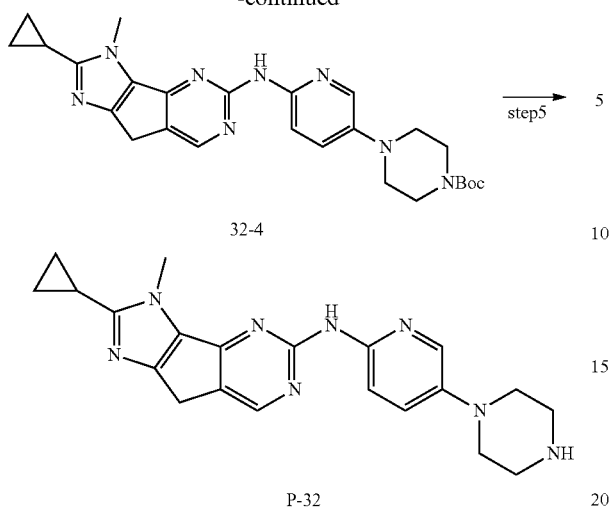

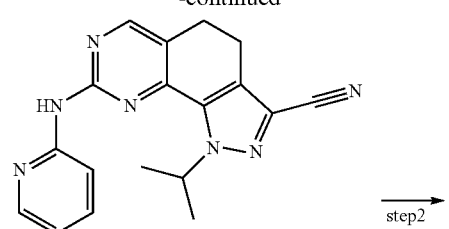

step 1: The preparation method was the same as the method for compound 3-5, except that compound 3-4 in the method for 3-5 was replaced by compound 31-1. MS m/z (ESI): 177[M+H]+.

step 2: The preparation method was the same as the method for compound 3-6, except that compound 3-5 in the method for 3-6 was replaced by compound 32-1. MS m/z (ESI): 231[M+H]+.

step 3: The preparation method was the same as the method for compound 3-7, except that compound 3-6 in the method for 3-7 was replaced by compound 32-2. MS m/z (ESI): 228[M+H]+.

step 4: The preparation method was the same as the method for compound 1-8, except that compound 1-7 in the method for 1-8 was replaced by compound 32-3. MS m/z (ESI): 489[M+H]+.

step 5: The preparation method was the same as the method for compound P-1, except that compound 1-8 in the method for P-1 was replaced by compound 32-4. Compound P-32 (10 mg, 10%) as a white solid was obtained by purification through Prep-HPLC. MS m/z (ESI): 389[M+H]+; $^1$H NMR (400 MHz, DMSO) δ9.00 (s, 1H), 8.22 (s, 1H), 8.15 (d, 1H), 7.92 (d, 1H), 7.37 (dd, 1H), 3.95 (s, 3H), 3.38 (s, 2H), 3.03-2.93 (m, 4H), 2.86-2.78 (m, 4H), 2.13-2.07 (m, 1H), 1.03-0.97 (m, 2H), 0.95-0.91 (m, 2H).

Example 52: Preparation of 1-isopropyl-8-(5-(piperazin-1-yl)pyridin-2-ylamino)-4,5-dihydro-1H-pyrazolo[4,3-H]quinazolin-3-carbonitrile (Compound P-52)

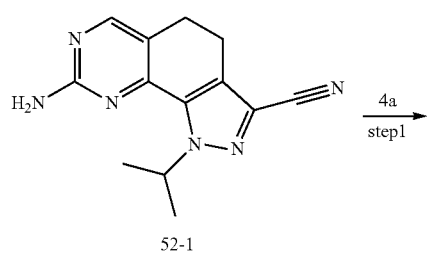

step 1: The preparation method was the same as the method for compound 1-8, except that compound 1-7 in the method for 1-8 was replaced by compound 52-1. MS m/z (ESI): 516[M+H]+.

step 2: The preparation method was the same as the method for compound P-1, except that compound 1-8 in the method for P-1 was replaced by compound 52-2. Compound P-52 (23.54 mg, yield 47%) as a white solid was obtained by purification through Prep-HPLC. MS m/z (ESI): 416[M+H]+; $^1$H NMR (400 MHz, DMSO) δ9.69 (s, 1H), 8.43 (s, 1H), 7.96 (d, 1H), 7.84 (d, 1H), 7.40 (dd, 1H), 6.12-5.96 (m, 1H), 3.10-3.00 (m, 4H), 2.93-2.86 (m, 4H), 2.87-2.79 (m, 4H), 1.42 (d, 6H).

Example 55: Preparation of 1-(9-isopropyl-6,8-dimethyl-2-(5-(piperazin-1-yl)pyridin-2-ylamino-6,8-dihydro-5H-pyrazolo[3,4-H]quinazolin-6-yl)ethanone (Compound P-55)

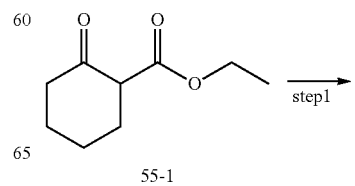

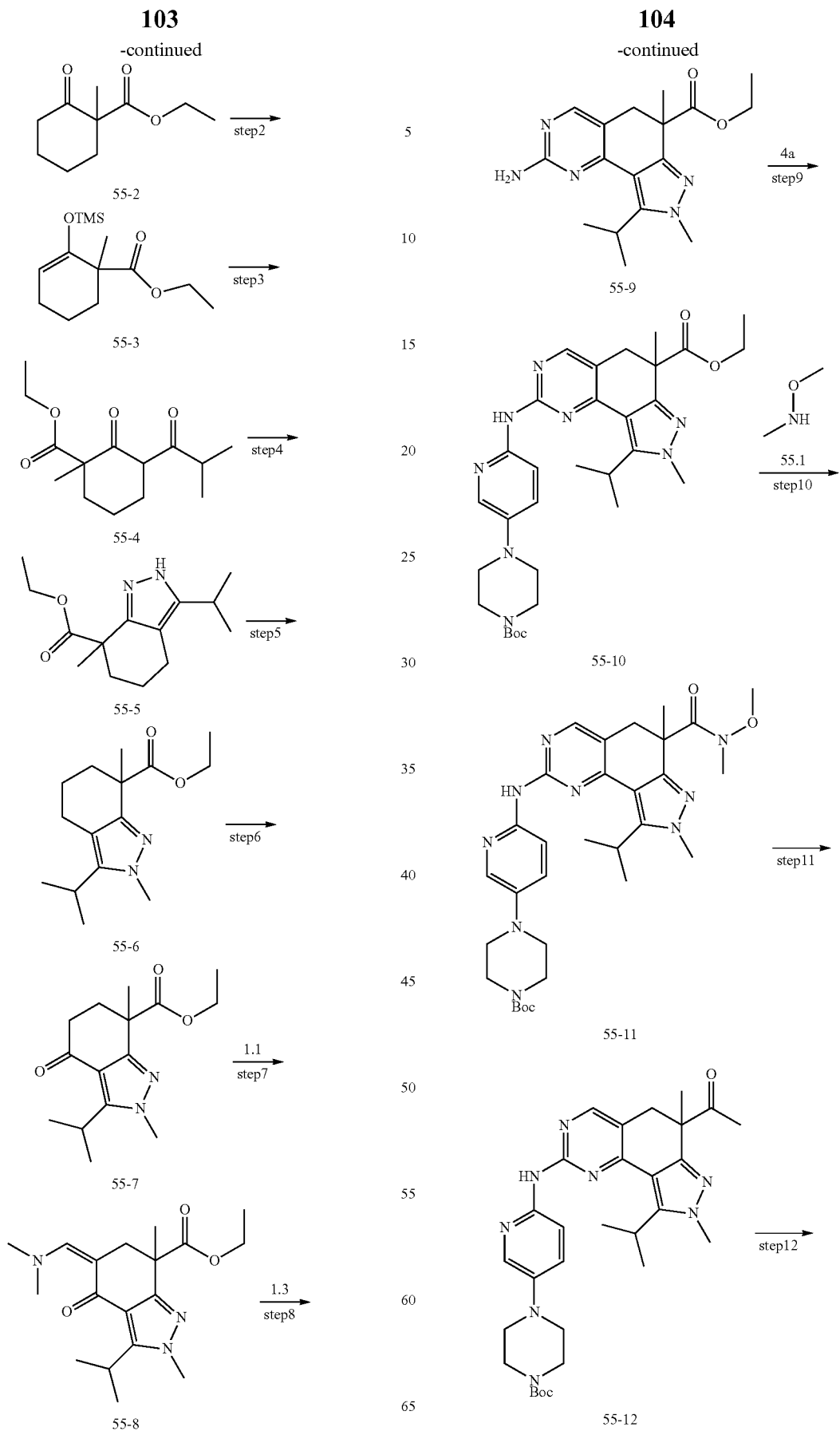

-continued

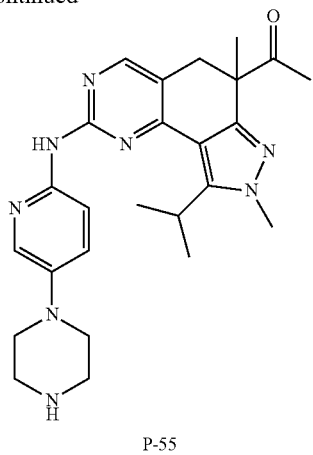

P-55 step 1: The preparation method was the same as the method for compound 3-5, except that compound 3-4 and 2-iodopropane in the method for compound 3-5 were replaced by compound 55-1 and iodomethane. MS m/z (ESI): 185[M+H]$^+$.

step 2: To a solution of compound 55-2 (1.84 g, 10 mmol) in THF (10 mL) was added LDA (5.5 mL, 11 mmol) at −78° C. under argon atmosphere, and after stirring at this temperature for 30 min, TMSCl (2.17 g, 20 mmol) was added. The mixture was warmed to room temperature and reacted for 1 h. The reaction solution was filtered and concentrated to give compound 55-3 which was used directly for the next reaction.

step 3: The preparation method was the same as the method for compound 8a-3, except that compound 8a-2 in the method for compound 8a-3 was replaced by compound 55-3. MS m/z (ESI): 255[M+H]$^+$.

step 4: The preparation method was the same as the method for compound 8a-4, except that compound 8a-3 in the method for compound 8a-4 was replaced by compound 55-4. MS m/z (ESI): 251[M+H]$^+$.

step 5: The preparation method was the same as the method for compound 3-5, except that compound 3-4 and 2-iodopropane in the method for compound 3-5 were replaced by compound 55-5 and iodomethane. MS m/z (ESI): 265[M+H]$^+$.

step 6: The preparation method was the same as the method for compound 8a, except that compound 8a-4 in the method for compound 8a was replaced by compound 55-6. MS m/z (ESI): 279[M+H]$^+$.

step 7: The preparation method was the same as the method for compound 3-6, except that compound 3-5 in the method for compound 3-6 was replaced by compound 55-7. MS m/z (ESI): 334[M+H]$^+$.

step 8: The preparation method was the same as the method for compound 3-7, except that compound 3-6 in the method for compound 3-7 was replaced by compound 55-8. MS m/z (ESI): 330[M+H]$^+$.

step 9: The preparation method was the same as the method for compound 1-8, except that compound 1-7 in the method for compound 1-8 was replaced by compound 55-9. MS m/z (ESI): 563[M+H]$^+$.

step 10: To a solution of compound 55-10 (80 mg, 0.14 mmol) in DMF (5 mL) was added compound 55.1 (17 mg, 0.17 mmol), HATU (81 mg, 0.21 mmol) and triethylamine (57 mg, 0.56 mmol) at room temperature under argon atmosphere. The reaction was stirred at room temperature for 1 h and LC-MS was used to monitor the reaction until the reaction was complete. The mixture was concentrated under reduced pressure and purified by Prep-HPLC to give compound 55-11 (42 mg, yield: 48%). MS m/z (ESI): 606[M+H]$^+$.

step 11: To a solution of compound 55-11 (80 mg, 0.14 mmol) in THE (5 mL) was added methylmagnesium bromide under argon atmosphere at 0° C. The mixture was stirred at 0° C. for 30 min and LC-MS was used to monitor the reaction until the reaction was complete. The reaction was quenched with water and the mixture was concentrated to give compound 55-12, which was used directly in the next step. MS m/z (ESI): 561[M+H]$^+$.

step 12: The preparation method was the same as the method for compound P-1, except that compound 1-8 in the method for compound P-1 was replaced by compound 55-12. Compound P-55 was obtained by purifying through prep-HPLC (22.7 mg, yield 92%). MS m/z (ESI): 461[M+H]$^+$; $^1$H NMR (400 MHz, DMSO) δ8.70 (s, 1H), 8.23 (s, 1H), 7.98 (d, 1H), 7.87 (d, 1H), 7.58 (s, 1H), 3.99 (dd, 1H), 3.89 (s, 3H), 3.33-3.28 (m, 4H), 3.29-3.19 (m, 5H), 2.64 (d, 1H), 2.01 (s, 3H), 1.43 (s, 3H), 1.38 (d, 6H).

Example 59: Preparation of 1-isopropyl-3-(methoxymethyl)-N-(5-(piperazin-1-yl)pyridin-2-yl)-4,5-dihydro-1H-pyrazolo[4,3-H]quinazolin-8-amine (Compound P-59)

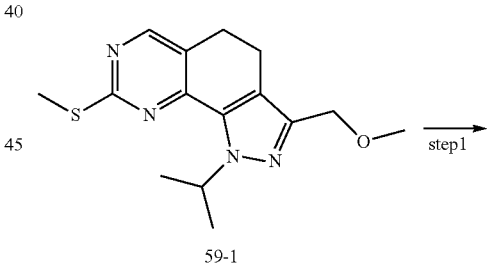

59-1

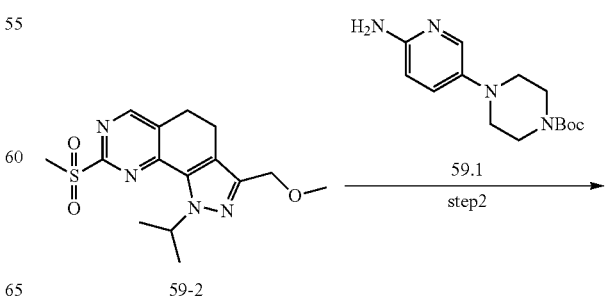

59-2

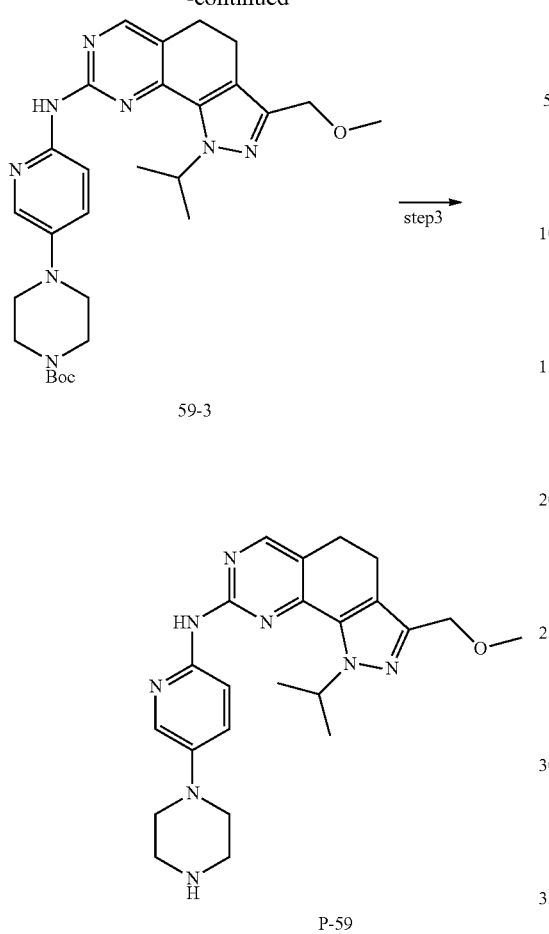

59-3

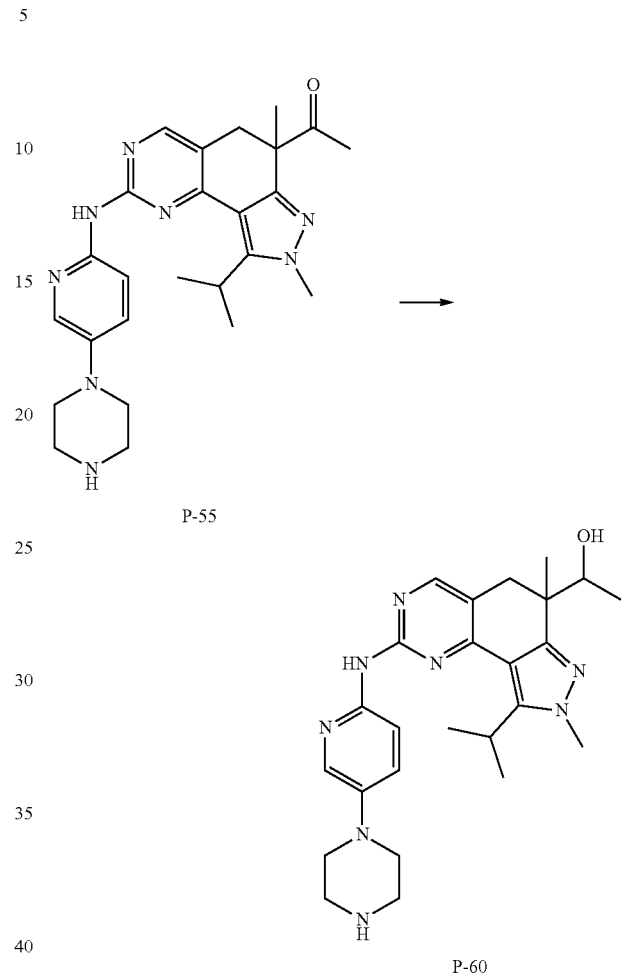

P-55

P-59

P-60

Example 60: Preparation of 1-(9-isopropyl-6,8-dimethyl-2-(5-(piperazin-1-yl)pyridin-2-ylamino)-6,8-dihydro-5H-pyrazolo[3,4-H]quinazolin-6-yl)ethanol (Compound P-60)

step 1: To a solution of compound 59-1 (25 mg, 0.082 mmol) in CH$_2$Cl$_2$ (10 mL) was added MCPBA (42 mg, 0.246 mmol) at room temperature and the mixture was stirred at room temperature for 30 min and LC-MS was used to monitor the reaction until the reaction was complete. The reaction solution was quenched with sodium thiosulfate and extracted with ethyl acetate. The organic layers were combined, concentrated under reduced pressure and purified by combiflash (PE:EA=1:2) to give compound 59-2 (25 mg, yield 92%). MS m/z (ESI): 337[M+H]$^+$.

step 2: To a solution of compound 59-2 (20 mg, 0.059 mmol) in toluene (2 mL) was added compound 59.1 (33 mg, 0.119 mmol) and NaOtBu (11 mg, 0.119 mmol) and the mixture was microwaved at 140° C. for 20 min under an argon atmosphere. The reaction mixture was concentrated and purified by combiflash (PE:EA=1:4) to give compound 59-3 (20 mg, yield 64%). MS m/z (ESI): 535[M+H]$^+$.

step 3: The preparation method was the same as the method for compound P-1, except that compound 1-8 in the method for compound P-1 was replaced by compound 59-3. Compound P-59 was obtained by purifying through prep-HPLC (1.7 mg, yield 10%). MS m/z (ESI): 435[M+H]$^+$; $^1$H NMR (400 MHz, DMSO) δ9.46 (s, 1H), 8.33 (s, 1H), 7.94 (d, 1H), 7.87 (d, 1H), 7.38 (dd, 1H), 5.88 (dt, 1H), 4.34 (s, 2H), 3.22 (s, 3H), 3.05-2.95 (m, 4H), 2.88-2.81 (m, 4H), 2.80-2.72 (m, 2H), 2.71-2.59 (m, 2H), 1.38 (d, 6H).

To a solution of compound P-55 (5 mg, 0.01 mmol) in THF (8 mL) and MeOH (2 mL) was added NaBH$_4$ (1 mg, 0.026 mmol) under ice-cooling, and the mixture was stirred at room temperature for 30 min. LC-MS was used to monitor the reaction until the reaction was complete. The reaction mixture was quenched with ethanol, concentrated and purified by Prep-HPLC to give compound P-60 (2.35 mg, yield 50%). MS m/z (ESI): 463[M+H]$^+$; $^1$H NMR (400 MHz, CDCl$_3$) δ8.30 (d, 1H), 8.15 (d, 1H), 7.96 (s, 1H), 7.31 (d, 1H), 4.13 (d, 1H), 4.04-3.93 (m, 1H), 3.88 (d, 3H), 3.35 (s, 8H), 3.04 (d, 1H), 2.63 (d, 1H), 2.49 (d, 1H), 1.45 (d, 6H), 1.21 (t, 3H), 1.14 (d, 3H).

Example 65

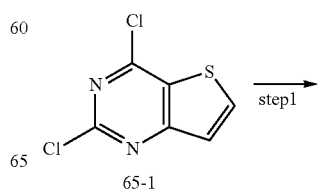

65-1

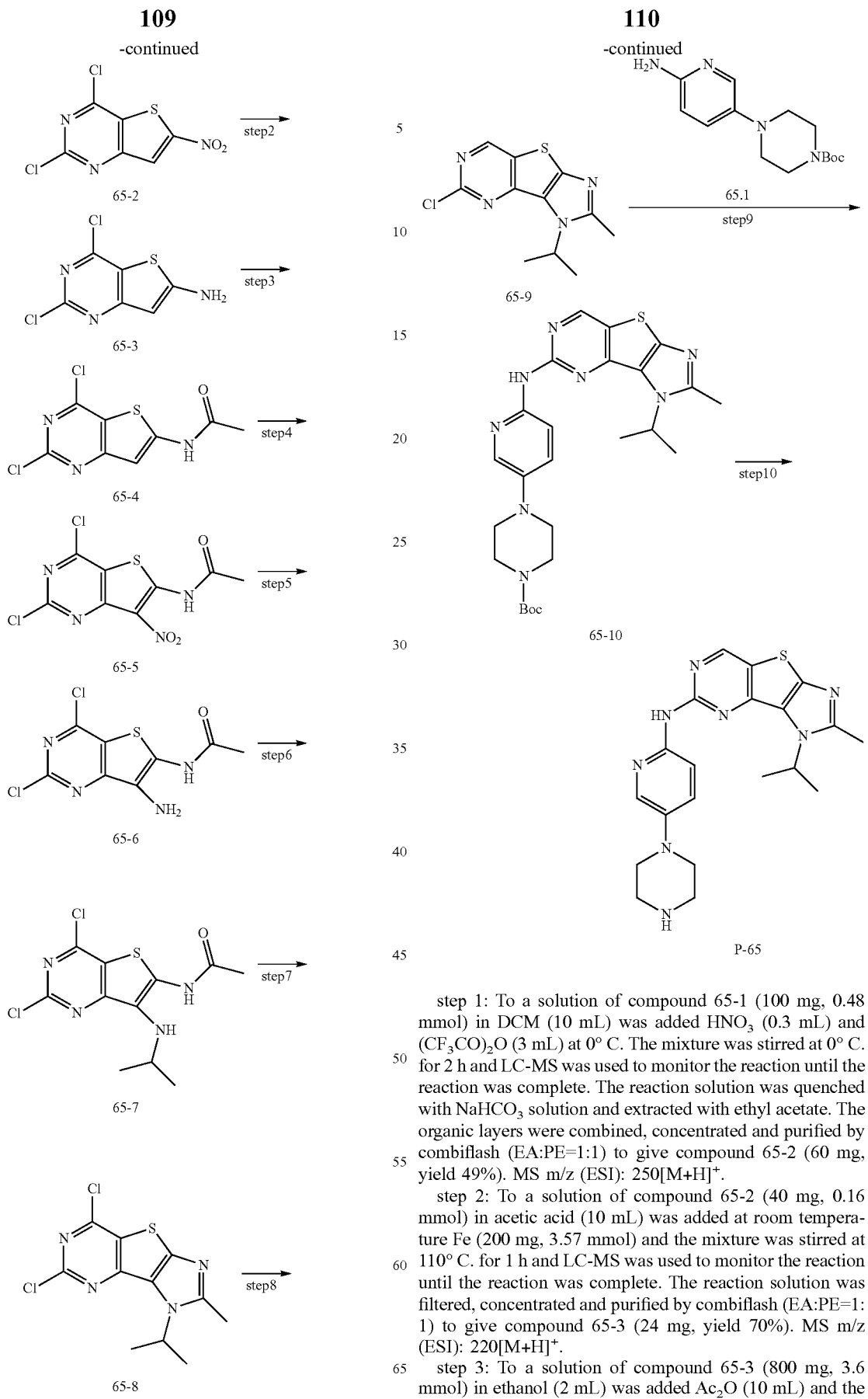

step 1: To a solution of compound 65-1 (100 mg, 0.48 mmol) in DCM (10 mL) was added $HNO_3$ (0.3 mL) and $(CF_3CO)_2O$ (3 mL) at 0° C. The mixture was stirred at 0° C. for 2 h and LC-MS was used to monitor the reaction until the reaction was complete. The reaction solution was quenched with $NaHCO_3$ solution and extracted with ethyl acetate. The organic layers were combined, concentrated and purified by combiflash (EA:PE=1:1) to give compound 65-2 (60 mg, yield 49%). MS m/z (ESI): 250[M+H]$^+$.

step 2: To a solution of compound 65-2 (40 mg, 0.16 mmol) in acetic acid (10 mL) was added at room temperature Fe (200 mg, 3.57 mmol) and the mixture was stirred at 110° C. for 1 h and LC-MS was used to monitor the reaction until the reaction was complete. The reaction solution was filtered, concentrated and purified by combiflash (EA:PE=1:1) to give compound 65-3 (24 mg, yield 70%). MS m/z (ESI): 220[M+H]$^+$.

step 3: To a solution of compound 65-3 (800 mg, 3.6 mmol) in ethanol (2 mL) was added $Ac_2O$ (10 mL) and the mixture was stirred at 110° C. for 2 h. LC-MS was used to monitor the reaction until the reaction was complete. The reaction solution was concentrated and purified by combiflash (EA:PE=1:1) to give compound 65-4 (700 mg, yield 73%). MS m/z (ESI): 262[M+H]+.

step 4: The preparation method was the same as the method for compound 65-2, except that compound 65-1 in the method for compound 65-2 was replaced by compound 65-4. MS m/z (ESI): 307 [M+H]+.

step 5: The preparation method was the same as the method for compound 65-3, except that compound 65-2 in the method for compound 65-3 was replaced by compound 65-5. MS m/z (ESI): 277 [M+H]+.

step 6: A solution of compound 65-6 (10 mg, 0.036 mmol) in 1,4-dioxane (10 mL) and trifluoroacetic acid (1 mL) was added to acetone (1 mL) and NaBH(OAc)3 (100 mg, 0.47 mmol) and the mixture was stirred at room temperature for 4 h. LC-MS was used to monitor the reaction until the reaction was complete. The reaction mixture was concentrated and purified by combiflash (PE:EA=1:4) to give compound 65-7 (5 mg, yield 45%). MS m/z (ESI): 319[M+H]+.

step 7: To a solution of compound 65-7 (28 mg, 0.09 mmol) in toluene (1 mL) was added to POCl3 (1 mL) at room temperature and the mixture was stirred at 105° C. for 3 h. LC-MS was used to monitor the reaction until the reaction was complete. The reaction solution was concentrated and purified by combiflash (EA:PE=1:1) to give compound 65-8 (10 mg, yield 38%). MS m/z (ESI): 301 [M+H]+.

step 8: To a solution of compound 65-8 (50 mg, 0.16 mmol) in methanol (5 ml) was added acetic acid (1 mL) and Zn (54 mg, 0.83 mmol), and the mixture was stirred at room temperature for 20 min. LC-MS was used to monitor the reaction until the reaction was complete. The reaction solution was concentrated and purified by combiflash (DCM:MeOH=20:1) to give compound 65-9 (40 mg, yield 90%). MS m/z (ESI): 267[M+H]).

step 9: The preparation method was the same as the method for compound 1-8, except that compound 1-7 and compound 4a in the method for compound 1-8 were replaced by compound 65-9 and compound 65.1. MS m/z (ESI): 509[M+H]+.

step 10: The preparation method was the same as the method for compound P-1, except that compound 1-8 in the method for compound P-1 was replaced by compound 65-10. Compound P-65 (4 mg, 25%) as a white solid was obtained by purification through Prep-HPLC. MS m/z (ESI): 409[M+H]+; 1H NMR (400 MHz, DMSO) δ 9.42 (s, 1H), 8.97 (s, 1H), 8.26 (d, 1H), 7.97 (d, 1H), 7.45 (dd, 1H), 4.75 (dt, 1H), 3.05-2.97 (m, 4H), 2.90-2.77 (m, 4H), 2.58 (s, 3H), 1.51 (d, 6H).

Compounds P-35, P-36, P-37 and P-40 were prepared by a method similar to that in Example 1.

Compounds P-33 and P-34 were prepared by a method similar to that in Example 22.

Compounds P-38 and P-66 were prepared by a method similar to that in Example 2. Compound P-39 was prepared by a method similar to that in Example 31.

Compounds P-41 to P-51, compounds P-53, P-54, P-56 to P-58, and P-63 were prepared by a method similar to that in Example 4 or 6.

Compound P-64 was prepared by a method similar to that for compound 65-7.

| Example No. | Structure/compound No. | MS[M + H]+ |
|---|---|---|
| 33 | 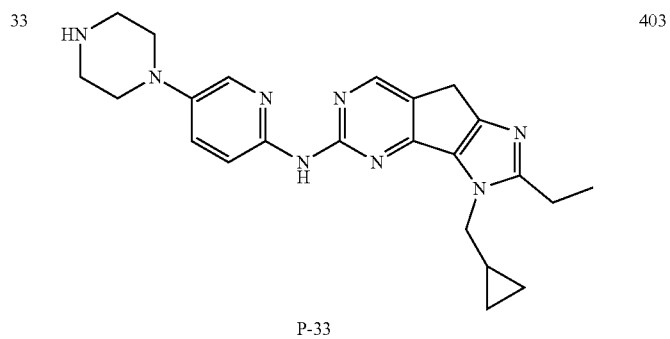<br>P-33 | 403 |
| 34 | 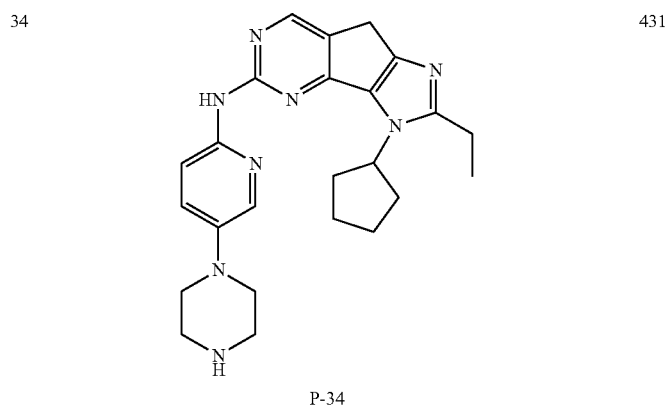<br>P-34 | 431 |

-continued
| Example No. | Structure/compound No. | MS[M + H]+ |
|---|---|---|
| 35 | 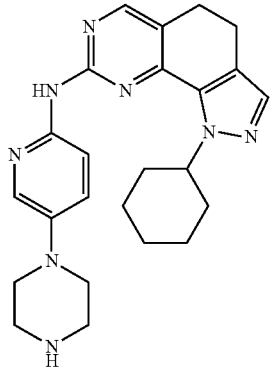<br>P-35 | 431 |
| 36 | 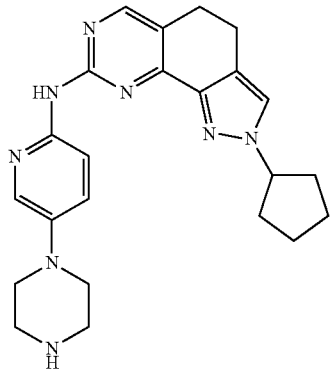<br>P-36 | 417 |
| 37 | 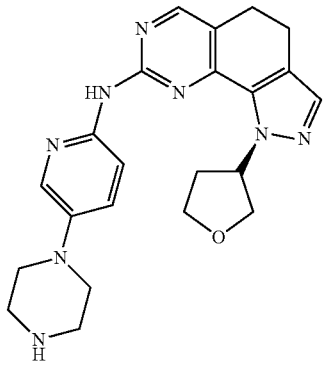<br>P-37 | 419 |

-continued
| Example No. | Structure/compound No. | MS[M + H]+ |
|---|---|---|
| 38 | 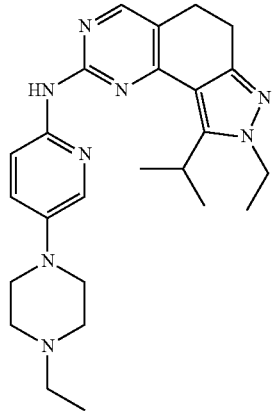
P-38 | 461 |
| 39 | 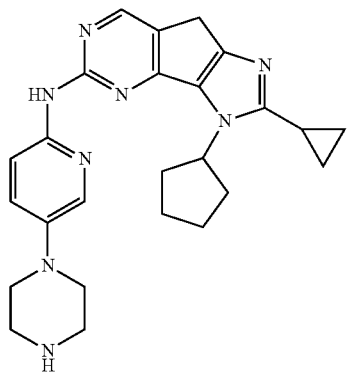
P-39 | 443 |
| 40 | 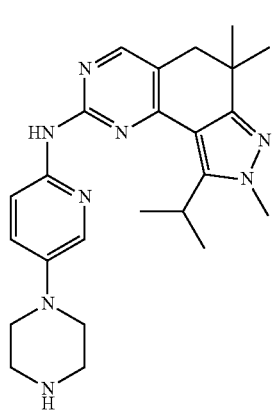
P-40 | 447 |

-continued
| Example No. | Structure/compound No. | MS[M + H]+ |
|---|---|---|
| 41 | 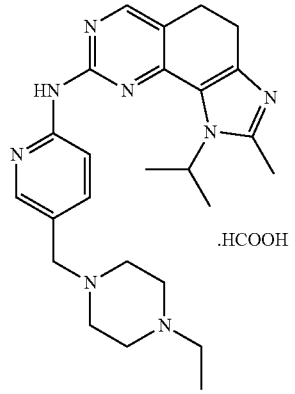<br>P-41 .HCOOH | 447 |
| 42 | 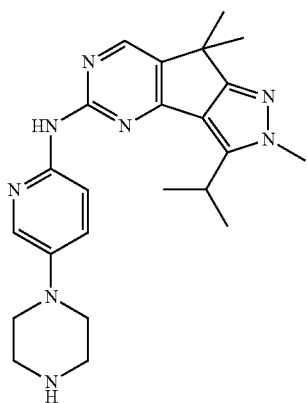<br>P-42 | 419 |
| 43 | 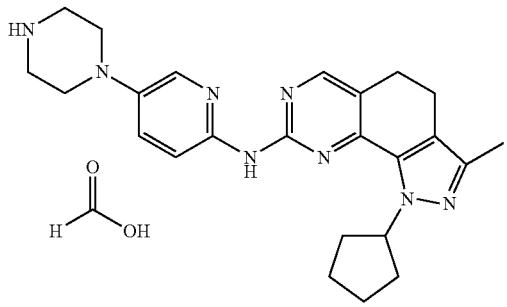<br>P-43 | 431 |

-continued
| Example No. | Structure/compound No. | MS[M + H]+ |
|---|---|---|
| 44 | 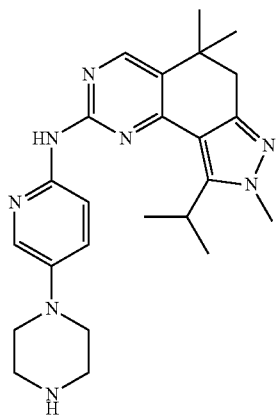<br>P-44 | 433 |
| 45 | 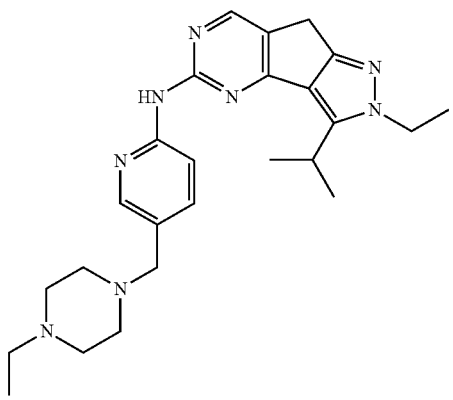<br>P-45 | 447 |
| 46 | 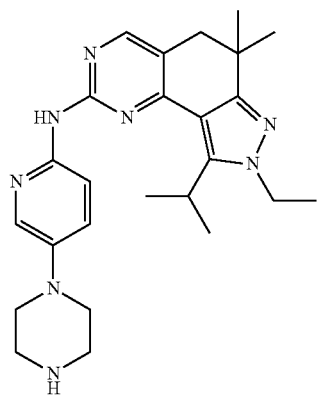<br>P-46 | 447 |

| Example No. | Structure/compound No. | MS[M + H]+ |
|---|---|---|
| 47 | 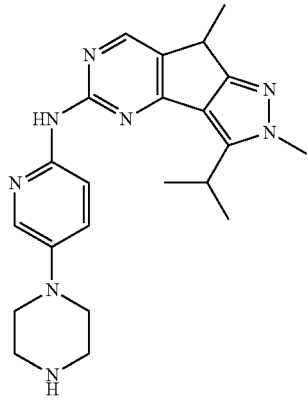<br>P-47 | 405 |
| 48 | 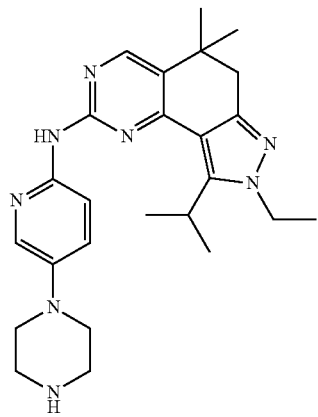<br>P-48 | 447 |
| 49 | 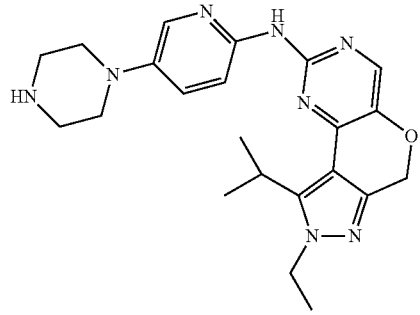<br>P-49 | 421 |

-continued
| Example No. | Structure/compound No. | MS[M + H]+ |
|---|---|---|
| 50 | 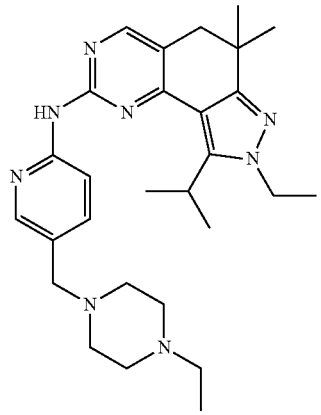<br>P-50 | 489 |
| 51 | 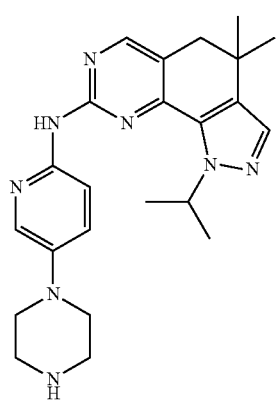<br>P-51 | 419 |
| 53 | 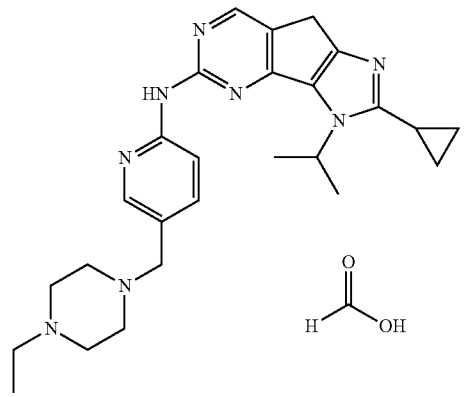<br>P-53 | 459 |

-continued
| Example No. | Structure/compound No. | MS[M + H]+ |
|---|---|---|
| 54 | 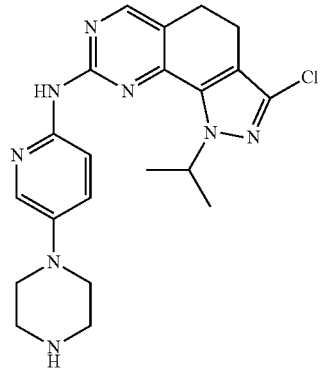<br>P-54 | 425 |
| 56 | 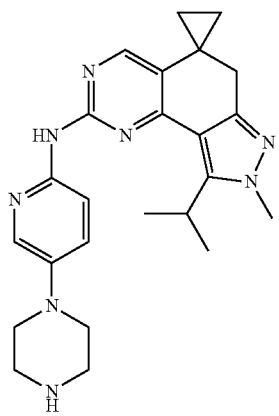<br>P-56 | 431 |
| 57 | 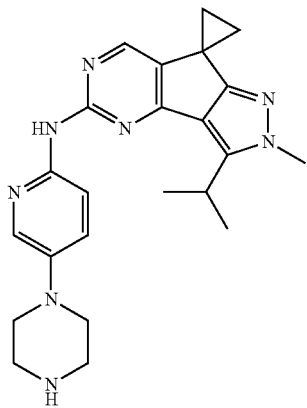<br>P-57 | 417 |

-continued
| Example No. | Structure/compound No. | MS[M + H]+ |
|---|---|---|
| 58 | 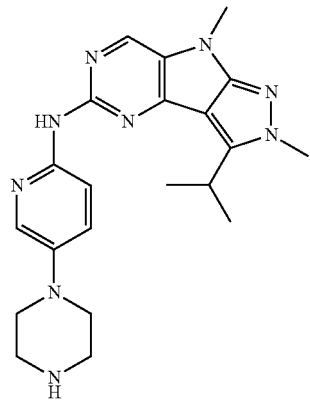<br>P-58 | 406 |
| 63 | 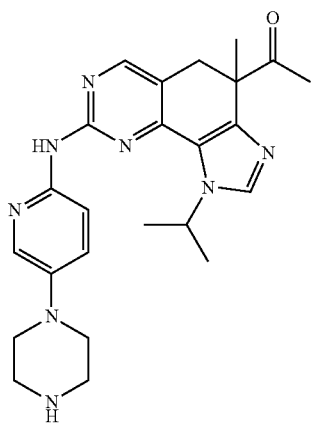<br>P-63 | 447 |
| 64 | 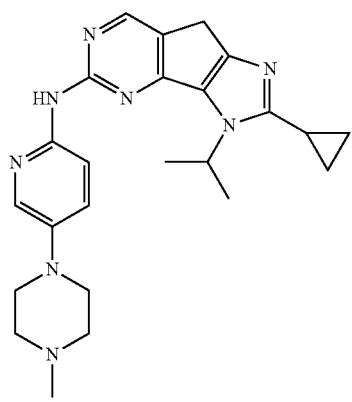<br>P-64 | 431 |

| Example No. | Structure/compound No. | MS[M + H]+ |
|---|---|---|
| 66 | 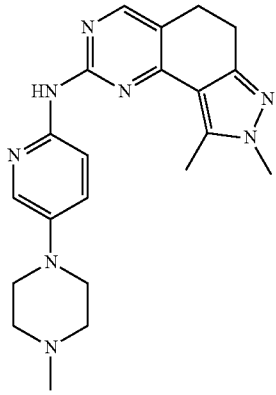<br>P-66 | 391 |

| Compound No. | ¹H NMR |
|---|---|
| P-33 | ¹H NMR (400 MHz, CDCl$_3$) δ 8.29 (d, 1H), 8.23 (s, 1H), 7.96 (d, 1H), 7.62 (s, 1H), 7.30 (dd, 1H), 4.08 (d, 2H), 3.49 (s, 2H), 3.10-3.05 (m, 8H), 2.84 (q, 2H), 1.43 (t, 4H), 1.24 (s, 1H), 0.57-0.55 (m, 4H). |
| P-34 | ¹H NMR (400 MHz, DMSO) δ 9.04 (s, 1H), 8.24 (s, 1H), 7.99 (d, 1H), 7.95 (d, 1H), 7.33 (d, 1H), 4.61-4.56 (m, 1H), 3.42 (s, 2H), 2.98-2.97 (m, 4H), 2.85-2.81 (m, 6H), 2.30-2.22 (m, 3H), 2.03-1.95 (m, 4H), 1.73-1.64 (m, 2H), 1.24 (t, 3H). |
| P-35 | 1H NMR (400 MHz, DMSO) δ 9.45 (s, 1H), 8.32 (s, 1H), 7.96 (d, 1H), 7.79 (d, 1H), 7.38-7.33 (dd, 2H), 5.46 (s, 1H), 3.00-2.97 (m, 4H), 2.83-2.85 (m, 4H), 2.76-2.74 (m, 2H), 2.64-2.62 (m, 2H), 1.86-1.84 (m, 2H), 1.75-1.73 (m, 4H), 1.59-1.57 (m, 1H), 1.34-1.32 (m, 2H), 1.16 (d, 1H). |
| P-36 | 1H NMR (400 MHz, DMSO) δ 9.24 (s, 1H), 8.29 (s, 1H), 9.11 (d, 1H), 7.91 (d, 1H), 7.67 (s, 1H), 7.35-7.32 (d, 1H), 4.74-4.67 (m, 1H), 2.96-2.94 (m, 4H), 2.80-2.77 (m, 4H), 2.47-2.45 (m, 4H), 2.07-2.04 (m, 2H), 1.92-1.90 (m, 2H), 1.79-1.75 (m, 2H), 1.64 (d, 2H). |
| P-37 | 1H NMR (400 MHz, DMSO) δ 9.76 (s, 1H), 8.65 (s, 2H), 8.35 (s, 1H), 8.01 (d, 1H), 7.92 (d, 1H), 7.44 (d, 2H), 6.32 (d, 1H), 4.01-3.98 (m, 2H), 3.76-3.74 (m, 2H), 3.23-3.21 (m, 8H), 2.76-2.73 (m, 1H), 2.67-2.65 (m, 2H), 2.49-2.47 (m, 1H), 2.31 (d, 2H). |
| P-38 | ¹H NMR (400 MHz, DMSO) δ 8.92 (s, 1H), 8.17 (s, 1H), 7.95-7.93 (m, 2H), 7.37 (dd, 1H), 4.12 (q, 2H), 3.92-3.85 (m, 1H), 3.29-3.27 (m, 4H), 3.08-3.07 (m, 4H), 2.75-2.73 (m, 2H), 2.68-2.66 (m, 2H), 2.46 (q, 2H), 1.37 (d, 6H), 1.31 (t, 3H), 1.00 (t, 3H). |
| P-39 | ¹H NMR (400 MHz, DMSO) δ 9.08 (s, 1H), 8.22 (s, 1H), 8.01 (d, 1H), 7.96 (d, 1H), 7.35 (d, 1H), 4.90-4.86 (m, 1H), 3.38 (s, 2H), 3.06 (s, 4H), 2.94 (s, 4H), 2.28-2.20 (m, 3H), 2.03-1.98 (m, 4H), 1.70-1.64 (m, 2H), 0.98-0.92 (m, 4H). |
| P-40 | ¹H NMR (400 MHz, DMSO) δ 8.94 (s, 1H), 8.15 (s, 1H), 7.95-7.91 (m, 2H), 7.35 (dd, 1H), 4.04-3.97 (m, 1H), 3.81 (s, 3H), 2.99-2.96 (m, 4H), 2.82-2.80 (m, 4H), 2.59 (s, 2H), 1.35 (d, 6H), 1.14 (s, 6H). |
| P-41 | 1H NMR (400 MHz, DMSO) δ 9.45 (s, 1H), 8.16 (d, 2H), 8.11 (s, 1H), 7.99 (d, 1H), 7.59 (d, 1H), 5.80 (s, 1H), 3.39-3.37 (m, 8H), 2.76-2.74 (m, 2H), 2.64-2.62 (m, 2H), 2.49-2.47 (m, 3H), 2.43-2.41 (m, 4H), 1.45 (d, 6H), 0.96 (d, 3H). |
| P-42 | ¹H NMR (400 MHz, DMSO) δ 9.07 (s, 1H), 8.36 (s, 1H), 8.17 (d, J = 8.0 Hz, 1H), 7.96 (d, J = 4.0 Hz, 1H), 7.38 (dd, J = 12.0, 4.0 Hz, 1H), 3.87 (s, 3H), 3.25-3.21 (m, 1H), 3.06-3.04 (m, 4H), 2.91-2.88 (m, 4H), 1.47 (d, J = 4.0 Hz, 6H), 1.43 (s, 6H). |
| P-43 | ¹H NMR (400 MHz, DMSO) δ 9.55 (s, 1H), 8.37-8.32 (m, 2H), 8.01 (d, 1H), 7.90 (d, 1H), 7.40 (dd, 1H), 6.06-6.00 (m, 1H), 3.55 (br, 2H), 3.09-3.08 (m, 4H), 2.93 (s, 4H), 2.82-2.78 (m, 2H), 2.64-2.60 (m, 2H), 2.16 (s, 3H), 2.09-2.03 (m, 2H), 1.93-1.85 (m, 4H), 1.63-1.62 (m, 2H). |
| P-44 | ¹H NMR (400 MHz, DMSO) δ 9.01 (s, 1H), 8.31 (s, 1H), 7.98-7.95 (m, 2H), 7.37 (d, 1H), 4.09-4.06 (m, 1H), 3.84 (s, 3H), 3.01 (s, 4H), 2.84 (s, 4H), 2.50 (s, 2H), 1.37 (d, 6H), 1.25 (s, 6H). |
| P-45 | 1H NMR (400 MHz, DMSO) δ 9.42 (s, 1H), 8.38 (s, 1H), 8.35 (d, 1H), 8.15 (s, 1H), 7.65-7.62 (m, 1H), 4.26-4.20 (m, 2H), 3.63 (s, 2H), 3.42 (s, 2H), 3.30-3.28 (m, 1H), 2.40-2.25 (m, 10H), 1.49 (d, 6H), 1.37 (t, 3H), 0.97 (t, 3H). |
| P-46 | ¹H NMR (400 MHz, DMSO) δ 8.92 (s, 1H), 8.15 (s, 1H), 7.95 (d, 1H), 7.93 (d, 1H), 7.36 (dd, 1H), 4.13 (q, 2H), 3.95-3.83 (m, 1H), 3.10-3.00 (m, 4H), 2.93-2.87 (m, 4H), 2.60 (s, 2H), 1.37 (d, 6H), 1.31 (t, 3H), 1.15 (s, 6H). |
| P-47 | ¹H NMR (400 MHz, DMSO)δ 9.07 (s, 1H), 8.35 (s, 1H), 8.17 (d, 1H), 7.95 (s, 1H), 7.39-7.36 (m, 1H), 3.88 (s, 3H), 3.83-3.78 (m, 1H), 3.28-3.24 (m, 1H), 3.03-3.00 (m, 4H), 2.86-2.83 (m, 4H), 1.48-1.45 (m, 6H), 1.39 (d, 3H) |

| Compound No. | $^1$H NMR |
|---|---|
| P-48 | $^1$H NMR (400 MHz, DMSO) δ 8.95 (s, 1H), 8.31 (s, 1H), 7.97-7.95 (m, 2H), 7.37 (dd, 1H), 4.15 (d, 2H), 3.98-3.95 (m, 1H), 2.99-2.97 (m, 4H), 2.82-2.80 (m, 4H), 2.57 (s, 2H), 1.39 (d, 6H), 1.35 (t, 3H), 1.25 (s, 6H). |
| P-49 | $^1$H NMR (400 MHz, CDCl$_3$) δ 8.23 (d, 1H), 8.05 (s, 1H), 7.96 (d, 1H), 7.57 (s, 1H), 7.30 (dd, 1H), 5.17 (s, 2H), 4.21 (q, 2H), 3.50-3.47 (m, 1H), 3.09 (d, 8H), 1.52 (d, 6H), 1.45 (t, 3H). |
| P-50 | $^1$H NMR (400 MHz, DMSO) δ 9.23 (s, 1H), 8.21 (s, 1H), 8.11 (s, 1H), 8.08 (d, 1H), 7.60 (d, 1H), 4.13 (q, 2H), 4.02-3.81 (m, 1H), 3.39 (s, 2H), 2.62 (s, 2H), 2.43-2.18 (m, 10H), 1.38 (d, 6H), 1.31 (t, 3H), 1.16 (s, 6H), 0.98-0.91 (m, 3H). |
| P-51 | $^1$H NMR (400 MHz, DMSO) δ 9.38 (s, 1H), 8.23-8.17 (m, 2H), 7.86-7.78 (m, 2H), 7.36-7.29 (m, 2H), 5.81 (br, 1H), 2.96 (s, 4H), 2.80 (s, 4H), 2.54 (s, 2H), 1.29 (d, 6H), 1.07 (s, 6H). |
| P-53 | $^1$H NMR (400 MHz, DMSO) δ 9.44 (s, 1H), 8.35-8.32 (m, 2H), 8.18-8.16 (m, 2H), 7.68 (dd, 1H), 4.95-4.92 (m, 1H), 3.44 (d, 4H), 2.49-2.39 (m, 8H), 2.35-2.34 (m, 2H), 2.32-2.30 (m, 1H), 1.68 (d, 6H), 1.04-0.94 (m, 7H). |
| P-54 | $^1$H NMR (400 MHz, DMSO) δ 9.12 (s, 1H), 8.48 (d, 1H), 8.24 (s, 1H), 7.91 (s, 1H), 7.40 (d, 1H), 4.63-4.44 (m, 1H), 3.14-2.99 (m, 4H), 3.03-2.82 (m, 8H), 1.36 (d, 6H). |
| P-56 | $^1$H NMR (400 MHz, DMSO) δ 8.82 (s, 1H), 8.00 (s, 1H), 7.97 (d, 1H), 7.80 (d, 1H), 7.65 (d, 1H), 4.07 (dt, 1H), 3.84 (s, 3H), 3.31 (dd, 4H), 3.24 (s, 4H), 2.62 (s, 2H), 1.38 (d, 6H), 0.95 (t, 2H), 0.80 (t, 2H). |
| P-57 | $^1$H NMR (400 MHz, DMSO) δ 9.09 (s, 1H), 8.18 (d, 1H), 8.08 (s, 1H), 7.95 (s, 1H), 7.39-7.36 (m, 1H), 3.86 (s, 3H), 3.28-3.25 (m, 1H), 3.04-3.00 (m, 4H), 2.86-2.80 (m, 4H), 1.71-1.69 (m, 2H), 1.56-1.53 (m, 2H), 1.49 (d, 6H). |
| P-58 | 1H NMR (400 MHz, DMSO) δ 8.77 (s, 1H), 8.50 (s, 1H), 8.23 (d, 1H), 7.89 (d, 1H), 7.32 (d, 1H), 3.90 (s, 3H), 3.57 (s, 3H), 3.33 (s, 1H), 2.96 (d, 4H), 2.82 (d, 4H), 1.48 (d, 6H). |
| P-63 | $^1$H NMR (400 MHz, DMSO) δ 9.40 (s, 1H), 8.21 (s, 1H), 8.09 (s, 1H), 7.95 (d, 1H), 7.89 (d, 1H), 7.40 (dd, 1H), 5.62 (dt, 1H), 3.27 (d, 1H), 3.08 (s, 4H), 2.95 (s, 4H), 2.67 (d, 1H), 1.98 (s, 3H), 1.49 (d, 3H), 1.41-1.40 (m, 6H). |
| P-64 | $^1$H NMR (400 MHz, DMSO) δ 9.15 (s, 1H), 8.27 (s, 1H), 8.22 (d, 1H), 7.98 (d, 1H), 7.46 (dd, 1H), 4.94-4.92 (m, 1H), 3.42 (s, 2H), 3.13-3.11 (m, 4H), 2.51-2.48 (m, 4H), 2.23 (s, 4H), 1.68 (d, 6H), 1.02-0.95 (m, 4H). |

Biological Test

Test Example 1 In Vitro Kinase Test

Recombinant CDK1/CCNB1 and CDK9/CCNT were purchased from BPS; CDK2/CCNA1, CDK4/CCND1 and CDK6/CCND1 were purchased from Invitrogen; CDK4/CycD3 and CDK6/CycD3 were purchased from Carna. Adenosine triphosphate (ATP) was purchased from Life tech. Substrate Ulight-4EBP1 and the corresponding detection antibody were purchased from Perkinelmer. The detection system was Perkinelmer's LANCE Ultra system.

In the kinase test, a compound to be tested was 1:3 diluted for 8 gradient points, added into a reaction plate, and then added an appropriate amount of recoinbinase. A buffer [50 mM HEPES pH17.5, 10 mM MgCl$_2$, 3 mM MnCl$_2$, 1 mM EGTA, 0.01% Tween-20, 1 mM TCEP] containing ATP/Ulight-4EBP1 premix with predetermined concentration was subsequently added, and the kinase reaction was started at room temperature. A test solution pre-mixed with 10 mM EDTA and detection antibody was added after a suitable reaction time, and then the fluorescence value was read on Tecan infinite pro after reacting for 1 hour at room temperature. The IC50 was calculated using a four-factor model fitting in a XLfit software. The results are shown in Table 1, Table 2 and Table 3.

TABLE 1

Inhibitory activity of compounds against CDK4

| Compound | CDK4 IC$_{50}$ (μM) | Compound | CDK4 IC$_{50}$ (μM) | Compound | CDK4 IC$_{50}$ (μM) |
|---|---|---|---|---|---|
| P-2 | 0.004 | P-3 | 0.006 | P-4 | 0.005 |
| P-5 | 0.022 | P-7 | 0.006 | P-8 | 0.010 |
| P-9 | 0.008 | P-10 | 0.016 | P-11 | 0.043 |
| P-12 | 0.008 | P-13 | 0.023 | P-14 | 0.005 |
| P-16 | 0.037 | P-18 | 0.015 | P-20 | 0.023 |
| P-21 | 0.035 | P-22 | 0.020 | P-23 | 0.006 |
| P-24 | 0.003 | P-25 | 0.009 | P-26 | 0.008 |
| P-27 | 0.006 | P-28 | 0.041 | P-29 | 0.007 |
| P-30 | 0.009 | P-31 | 0.013 | P-33 | 0.059 |
| P-34 | 0.023 | P-35 | 0.074 | P-36 | 0.138 |
| P-37 | 0.041 | P-38 | 0.014 | P-39 | 0.033 |
| P-40 | 0.010 | P-41 | 0.005 | P-42 | 0.017 |
| P-43 | 0.009 | P-44 | 0.173 | P-45 | 0.037 |
| P-46 | 0.008 | P-47 | 0.005 | P-48 | 0.097 |
| P-49 | 0.007 | P-50 | 0.006 | P-51 | 0.042 |
| P-52 | 0.006 | P-53 | 0.010 | P-55 | 0.128 |
| P-56 | 0.103 | P-57 | 0.003 | P-58 | 0.010 |
| P-59 | 0.021 | P-60 | 0.160 | P-63 | 0.056 |
| P-65 | 1.073 | P-66 | 0.023 | D1 | 0.008 |

TABLE 2

Inhibitory activity of compounds against CDK6

| Compound | CDK6 IC$_{50}$ (μM) | Compound | CDK6 IC$_{50}$ (μM) | Compound | CDK6 IC$_{50}$ (μM) |
|---|---|---|---|---|---|
| P-2 | 0.038 | P-3 | 0.059 | P-4 | 0.033 |
| P-5 | 0.256 | P-7 | 0.042 | P-8 | 0.161 |
| P-9 | 0.040 | P-10 | 0.132 | P-11 | 0.165 |
| P-12 | 0.036 | P-13 | 0.043 | P-14 | 0.020 |

TABLE 2-continued

Inhibitory activity of compounds against CDK6

| Compound | CDK6 IC$_{50}$ (μM) | Compound | CDK6 IC$_{50}$ (μM) | Compound | CDK6 IC$_{50}$ (μM) |
|---|---|---|---|---|---|
| P-16 | 0.053 | P-18 | 0.201 | P-20 | 0.030 |
| P-21 | 0.706 | P-22 | 0.043 | P-23 | 0.085 |
| P-24 | 0.011 | P-25 | 0.031 | P-26 | 0.132 |
| P-27 | 0.008 | P-28 | 0.121 | P-29 | 0.017 |
| P-30 | 0.034 | P-31 | 0.088 | P-33 | 0.841 |
| P-34 | 0.394 | P-35 | 0.252 | P-36 | 0.714 |
| P-37 | 0.362 | P-38 | 0.043 | P-39 | 0.184 |
| P-40 | 0.048 | P-41 | 0.044 | P-42 | 0.222 |
| P-43 | 0.046 | P-44 | 0.415 | P-45 | 0.451 |
| P-46 | 0.035 | P-47 | 0.046 | P-48 | 0.897 |
| P-49 | 0.070 | P-50 | 0.040 | P-51 | 0.117 |
| P-52 | 0.033 | P-53 | 0.057 | P-55 | 0.523 |
| P-56 | 0.831 | P-57 | 0.058 | P-58 | 0.263 |
| P-59 | 0.083 | P-60 | 0.762 | P-63 | 0.160 |
| P-65 | >3 | P-66 | 0.063 | D1 | 0.053 |

TABLE 3

Inhibitory activity of compounds against CDK1 and CDK2

| Compound | CDK1 IC$_{50}$ (μM) | CDK2 IC$_{50}$ (μM) | Compound | CDK1 IC$_{50}$ (μM) | CDK2 IC$_{50}$ (μM) |
|---|---|---|---|---|---|
| P-2 | 0.427 | 0.896 | P-3 | 0.912 | 1.154 |
| P-4 | 7.955 | 4.759 | P-5 | 5.315 | 2.998 |
| P-7 | 8.526 | 9.849 | P-8 | >10 | 8.254 |
| P-9 | 5.168 | 1.443 | P-12 | >10 | 7.978 |
| P-13 | 5.654 | 8.315 | P-14 | 1.023 | 0.523 |
| P-18 | 7.472 | 9.462 | P-21 | 6.366 | 5.054 |
| P-23 | 2.780 | 1.304 | P-24 | 3.570 | 0.816 |
| P-25 | >10 | 8.521 | P-29 | >1 | 0.457 |
| P-30 | 0.855 | 0.761 | P-31 | 4.390 | 4.783 |
| P-33 | 4.226 | 5.563 | P-34 | 0.651 | 1.721 |
| P-38 | 0.837 | 0.538 | P-39 | 1.039 | 2.333 |
| P-40 | 1.242 | 0.756 | P-42 | 4.321 | 1.294 |
| P-46 | 0.818 | 0.469 | P-47 | 0.706 | 0.510 |
| P-53 | 6.088 | 8.746 | P-57 | 0.942 | 0.803 |
| P-58 | >10 | 5.981 | P-59 | >10 | >10 |
| P-66 | 0.926 | 0.674 | D1 | 0.093 | 0.023 |

It can be seen from Table 1, Table 2 and Table 3 that the exemplary compounds of the present disclosure have strong inhibitory activity against CDK4 and CDK6, but have weak inhibitory activity against CDK1 and CDK2, and therefore have a selective inhibitory activity against CDK4/6. Although comparative compound 1 (D1, the specific structure is shown below, also can be seen in WO2012010704, Example 1-44) has a strong inhibitory activity against CDK4 and CDK6, it also has a strong inhibitory activity against CDK1 and CDK2, and therefore does not show selective inhibitory activity against CDK4/6.

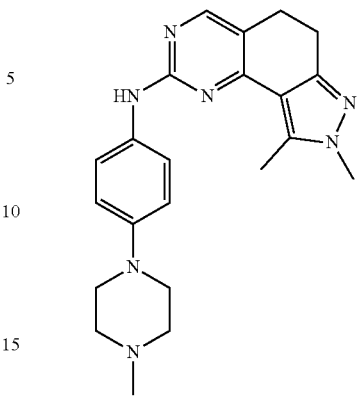

Comparative compound 1

Test Example 2 Pharmacokinetics and Brain Distribution Test

Experimental Protocol:

Test Animals: healthy adult male SD rats (weight 210-230 g per rat, 12 rats, fasted overnight, fed 4 hours after dosing), provided by SLAC company; preparation of oral solution: 40.14 mg of compound P-53 was weighed and put into a clean tube, and 36.479 mL of 0.5% HPC-H (TCI, E6ZQA) in acetate buffer (PH4.5) was added into the tube, which was then vortexed for 1-2 min. Then the solution was sonicated for 20-25 min and stirred for 20-25 min.

SD rats were administered via intragastric administration (10 mg/kg (10 mL/kg)); samples were collected at 0.5, 1, 2 and 4 hr after dosing (total 4 timepoints), wherein only plasma samples were collected continuously, and brain tissue and cerebrospinal fluid were collected at each time point.

Blood collection: The animal was restrained manually and at each time point collected approximately 150 μL blood via tail vein into a K$_2$EDTA-containing tube. Within 15 minutes, the blood sample was put on wet ice and centrifuged to obtain plasma sample (2000 g, 5 min under 4° C.).

Brain tissue collection: Made an incision in the middle of the animal's scalp and then shrank the skin. The skull was moved behind the brain by a small bone cutter and rongeurs. The brain was removed by a spatula, rinsed with cold saline, and placed in a screw-top tube, which was then stored under −70° C. until test.

Cerebrospinal fluid collection: The animal was euthanized under deep anesthesia with air bubble tail vein injection. The CSF was collected by direct puncture of butterfly needle into the cisterna magna, using the occipital bone and the wings of the atlas as landmarks. A piece of white paper was used as a background to monitor color change in the sample just above the needle during collection. Upon observation of color change, the PE tube was quickly clamped off above the color change and cut just above the clamped site. And then the clear sample was drawn into the syringe.

Sample storage and possessing: Plasma, brain and CSF samples will be stored in dry ice temporarily and transferred into −80° C. freezer for long term preservation.

Analytical method: the plasma and brain of SD rats were used as substrates, and Glipizide was used as an internal standard. LCMSMS-002 (API-4000, triple quadrupole) was used for testing and analysis. 30 μL of plasma samples and brain tissue samples were taken respectively and were added with 200 μL ACN containing 100 ng/mL IS (Glipizide). The mixture was vortexed for 10 min and centrifuged at 5800 rpm for 10 min. 2 μL supernatant was taken after centrifugation for LC-MS/MS analysis. 10 μL of CSF sample was added with 10 μL of MeOH/H$_2$O (1/1) and 60 μL of ACN containing 100 ng/mL IS (Glipizide). The mixture was vortexed for 5 min, and 2 μL supernatant was taken for LC-MS/MS analysis. The drug concentration was determined by LC-MS/MS method, the pharmacokinetic parameters in the plasma, brain, and CSF of rats are shown in Table 4:

TABLE 4

| Area under the curve after oral administration of 10 mg/kg of compound in rats | |
|---|---|
| Example | compound P-53 |
| AUC (hr * ng/mL) in plasma | 2620 |
| AUC (hr * ng/mL) in brain tissue | 4944 |
| AUC (hr * ng/mL) in CSF | 204 |

As can be seen from Table 4, compound P-53 can cross the blood-brain barrier and can be well distributed into the brain, which has better brain permeability.

All publications mentioned herein are incorporated by reference as if each individual document was cited as a reference, as in the present application. It should also be understood that, after reading the above teachings of the present disclosure, those skilled in the art can make various changes or modifications, equivalents of which falls in the scope of claims as defined in the appended claims.

The invention claimed is:

1. A compound of formula (I), or a pharmaceutically acceptable salt, stereoisomer, or solvate thereof:

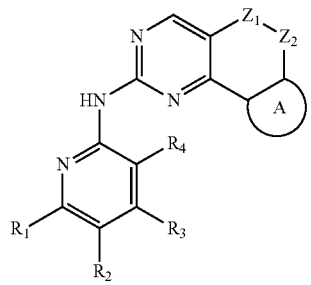

(I)

wherein, $R_1$, $R_3$, $R_4$ are each independently hydrogen, halogen, or $C_{1-8}$ alkyl;

$R_2$ is —(CH$_2$)$_n$—Y, wherein Y is piperidine or piperazine, the Y group is unsubstituted or substituted with $L_1$ or —CH$_2$-$L_1$; $L_1$ is methyl, ethyl, n-propyl, or isopropyl; n is 0, 1 or 2;

$Z_1$, $Z_2$ are each independently a bond, CR$_a$R$_b$, NR$_c$ or O, and $Z_1$, $Z_2$ are not a bond, NR$_c$, or O at the same time;

$R_a$, $R_b$ are each independently hydrogen, halogen, or $C_{1-8}$ alkyl; or $R_a$, $R_b$ and the carbon atom attached thereto form a 3 to 6 membered saturated monocyclic ring;

$R_c$ is hydrogen or $C_{1-8}$ alkyl;

the ring A has a structure represented by formula (A-1), formula (A-2), formula (A-3) or formula (A-4):

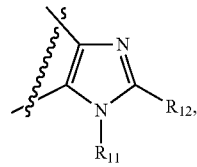

(A-1)

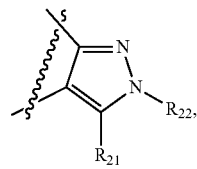

(A-2)

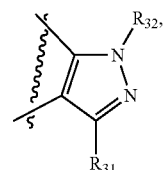

(A-3)

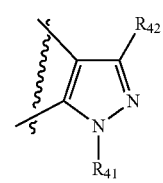

(A-4)

wherein $R_{11}$, $R_{22}$, $R_{32}$, $R_{41}$ are each independently hydrogen or —(CH$_2$)$_q$-$L_3$; wherein $L_3$ is $C_{1-8}$ alkyl, halogenated $C_{1-8}$ alkyl, $C_{3-8}$ cycloalkyl, or 4 to 6 membered saturated single heterocycle; q is 0 or 1;

$R_{12}$, $R_{21}$, $R_{31}$, $R_{42}$ are each independently hydrogen, halogen or —(CH$_2$)$_r$-$L_4$; $L_4$ is CN, $C_{1-8}$ alkyl, $C_{1-8}$ alkoxy, halogenated $C_{1-8}$ alkyl or $C_{3-8}$ cycloalkyl; r is 0 or 1.

2. The compound of claim 1, or a pharmaceutically acceptable salt, stereoisomer, or solvate thereof, wherein Y is piperazine, the Y group is unsubstituted or substituted with $L_1$ or —CH$_2$-$L_1$; $L_1$ is methyl or ethyl.

3. The compound of claim 1, or a pharmaceutically acceptable salt, stereoisomer, or solvate thereof, wherein $R_c$ is hydrogen or methyl.

4. The compound of claim 1, or a pharmaceutically acceptable salt, stereoisomer, or solvate thereof, wherein $R_{11}$, $R_{22}$, $R_{32}$, $R_{41}$ are each independently hydrogen or —(CH$_2$)$_q$-$L_3$; wherein $L_3$ is $C_{1-3}$ alkyl, halogenated $C_{1-3}$ alkyl, $C_{3-6}$ cycloalkyl, or 4 to 6 membered saturated single heterocycle; q is 0 or 1.

5. The compound of claim 1, or a pharmaceutically acceptable salt, stereoisomer, or solvate thereof, wherein $R_{12}$, $R_{21}$, $R_{31}$, $R_{42}$ are each independently hydrogen, halogen or —(CH$_2$)$_r$-$L_4$; $L_4$ is CN, $C_{1-3}$ alkyl, $C_{1-3}$ alkoxy, or $C_{3-6}$ cycloalkyl; r is 0 or 1.

6. The compound of claim 1, or a pharmaceutically acceptable salt, stereoisomer, or solvate thereof, wherein $R_a$, $R_b$ are each independently hydrogen, or $C_{1-3}$ alkyl; or $R_a$, $R_b$ and the carbon atom attached thereto form a cyclopropyl ring.

7. The compound of claim 1, or a pharmaceutically acceptable salt, stereoisomer, or solvate thereof, wherein

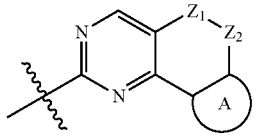

is a structure represented by formula (B-1), formula (B-2), formula (B-3) or formula (B-4):

(B-1)
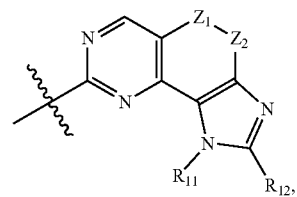

(B-2)
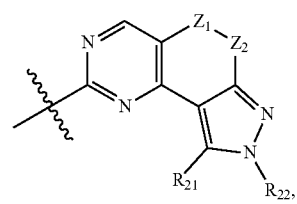

(B-3)
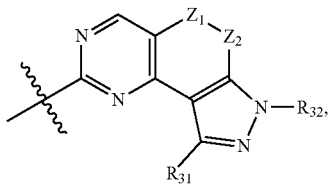

(B-4)
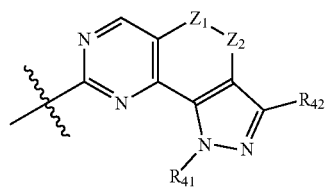

wherein $Z_1$, $Z_2$, $R_{11}$, $R_{22}$, $R_{32}$, $R_{41}$, $R_{12}$, $R_{21}$, $R_{31}$, $R_{42}$ are as defined in claim 1.

8. The compound of claim 1, or a pharmaceutically acceptable salt, stereoisomer, or solvate thereof, wherein $Z_1$ is a bond; $Z_2$ is $CR_{1a}R_{1b}$, or $NR_c$; $R_{1a}$, $R_{1b}$ are defined as $R_a$, $R_b$.

9. The compound of claim 1, or a pharmaceutically acceptable salt, stereoisomer, or solvate thereof, wherein $Z_1$ is $CR_{1a}R_{1b}$ or O; $Z_2$ is $CR_{2a}R_{2b}$; $R_{1a}$, $R_{1b}$, $R_{2a}$, $R_{2b}$ are defined as $R_a$, $R_b$.

10. The compound of claim 1, or a pharmaceutically acceptable salt, stereoisomer, or solvate thereof, wherein $Z_1$ is $CR_{1a}R_{1b}$; $Z_2$ is $CR_{2a}R_{2b}$; $R_{1a}$, $R_{1b}$, $R_{2a}$, $R_{2b}$ are defined as $R_a$, $R_b$.

11. The compound of claim 7, or a pharmaceutically acceptable salt, stereoisomer, or solvate thereof, wherein $Z_1$ is a bond; $Z_2$ is $CR_{2a}R_{2b}$ or $NR_c$;

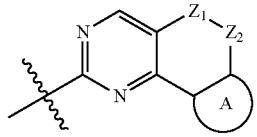

is the structure represented by formula (B-1), formula (B-2) or formula (B-3); $R_{2a}$, $R_{2b}$ are defined as $R_a$, $R_b$.

12. The compound of claim 7, or a pharmaceutically acceptable salt, stereoisomer, or solvate thereof, wherein $Z_1$ is $CR_{1a}R_{1b}$ or O; $Z_2$ is $CR_{2a}R_{2b}$;

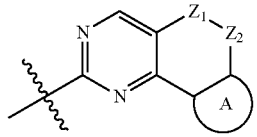

is the structure represented by formula (B-1), formula (B-2) or formula (B-4); $R_{1a}$, $R_{1b}$, $R_{2a}$, $R_{2b}$ are defined as $R_a$, $R_b$.

13. The compound of claim 7, or a pharmaceutically acceptable salt, stereoisomer, or solvate thereof, wherein $Z_1$ is a bond or O; $Z_2$ is $CR_{2a}R_{2b}$;

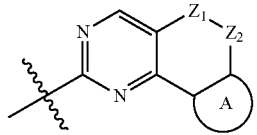

is the structure represented by formula (B-2); $R_{2a}$, $R_{2b}$ are defined as $R_a$, $R_b$.

14. The compound of claim 7, or a pharmaceutically acceptable salt, stereoisomer, or solvate thereof, wherein $Z_1$ is $CR_{1a}R_{1b}$; $Z_2$ is $CR_{2a}R_{2b}$;

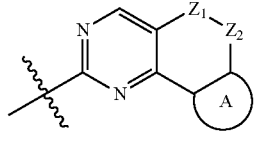

is the structure represented by formula (B-1); $R_{1a}$, $R_{1b}$, $R_{2a}$, $R_{2b}$ are defined as $R_a$, $R_b$.

15. The compound of claim 1, or a pharmaceutically acceptable salt, stereoisomer, or solvate thereof, wherein $R_1$, $R_3$, $R_4$ are each independently hydrogen.

16. The compound of claim 1, or a pharmaceutically acceptable salt, stereoisomer, or solvate thereof, wherein n is 0 or 1.

17. The compound of claim 1, or a pharmaceutically acceptable salt, stereoisomer, or solvate thereof, wherein the compound is selected from:
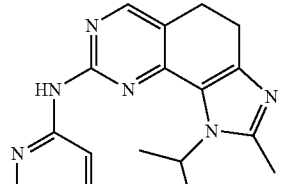
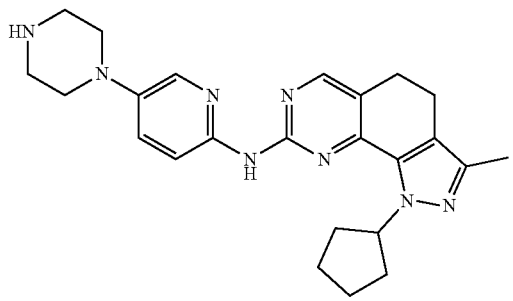
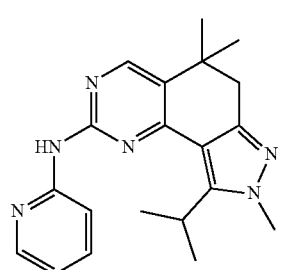
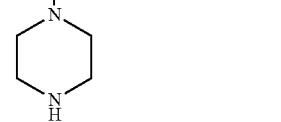
-continued
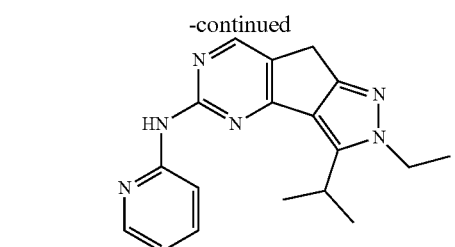
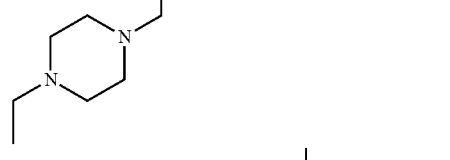
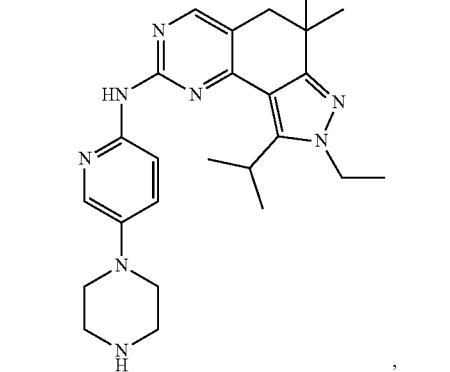
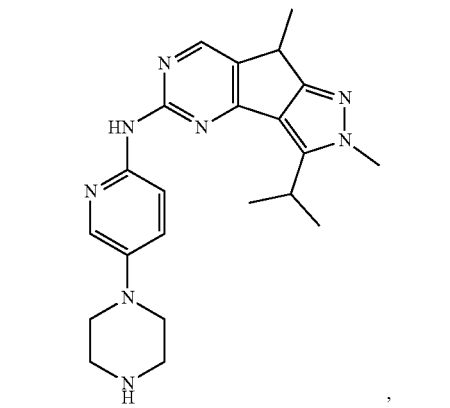
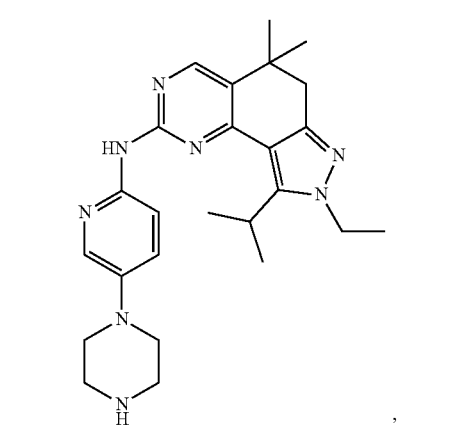

141
-continued
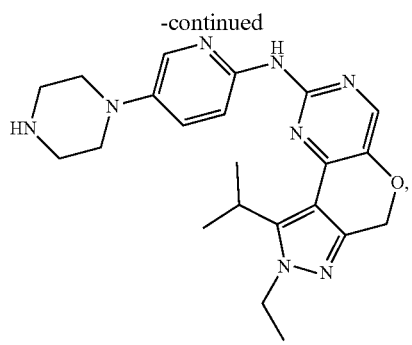
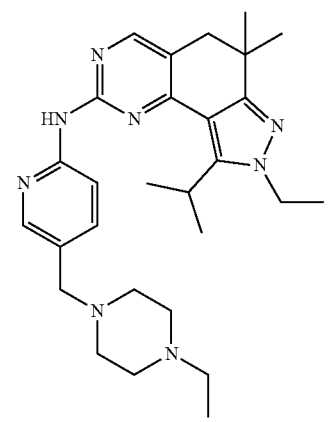
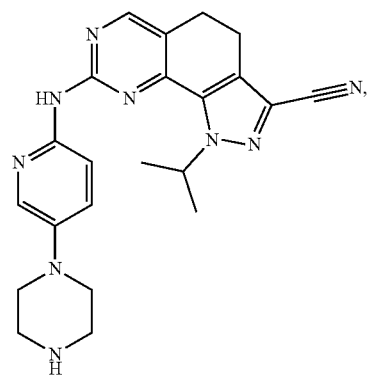
142
-continued
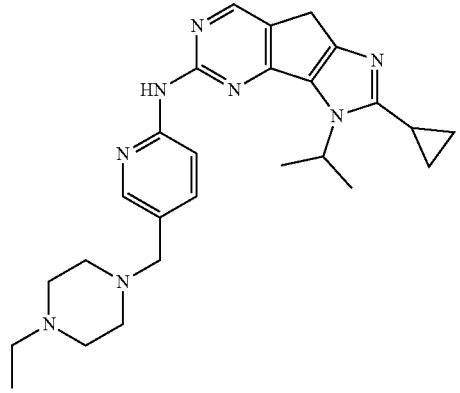
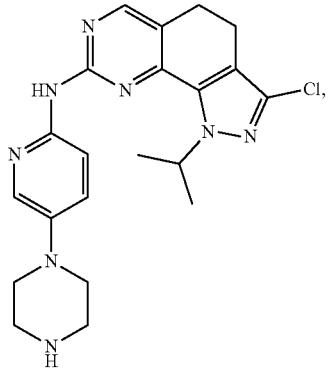
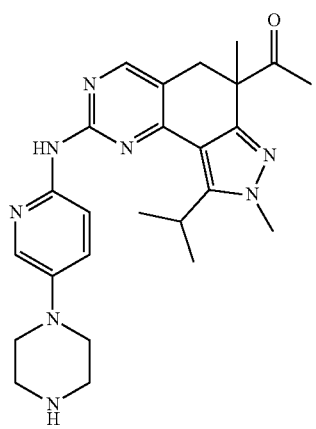
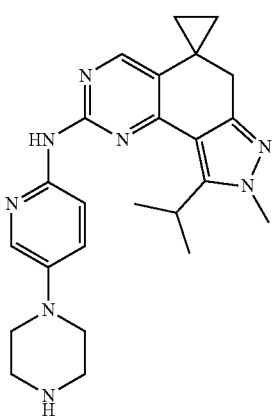

143

-continued

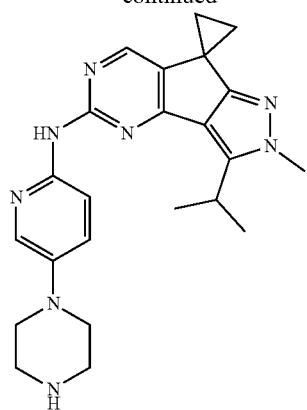

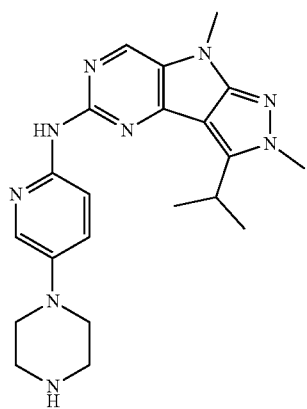

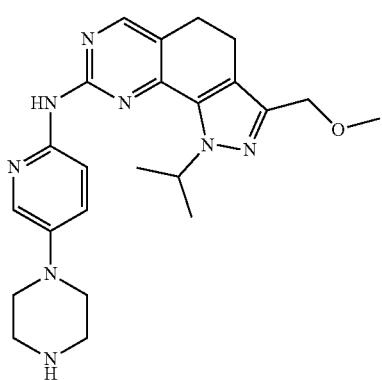

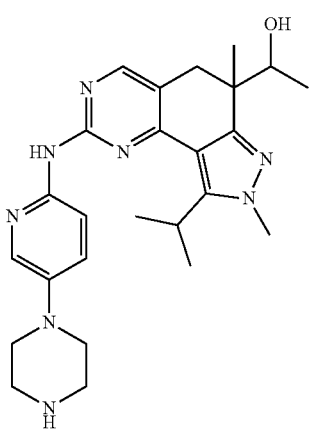

144

-continued

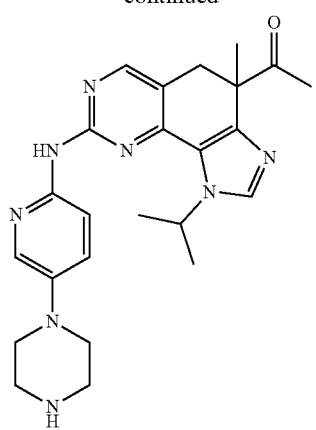

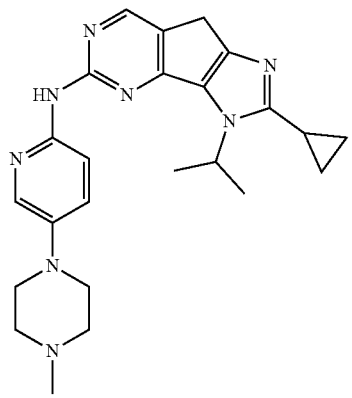

18. A pharmaceutical composition, comprising: the compound of claim 1, or a pharmaceutically acceptable salt, stereoisomer, or solvate thereof; and a pharmaceutically acceptable carrier.

19. A method for inhibiting CDK4 and/or CDK6 activity in a subject in need thereof, comprising administering to a subject the compound of claim 1 or a pharmaceutically acceptable salt, stereoisomer or solvate thereof.

20. The compound of claim 1, or a pharmaceutically acceptable salt, stereoisomer, or solvate thereof, wherein the compound is selected from:

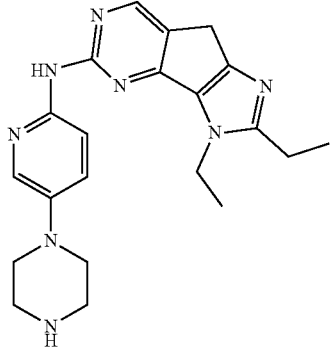

145
-continued
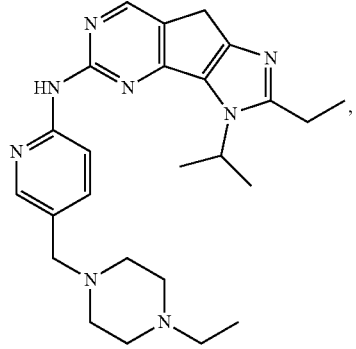 [SMILES: CCc1nc2c(n1C(C)C)-c1nc(Nc3ccc(CN4CCN(CC)CC4)cn3)ncc1C2]
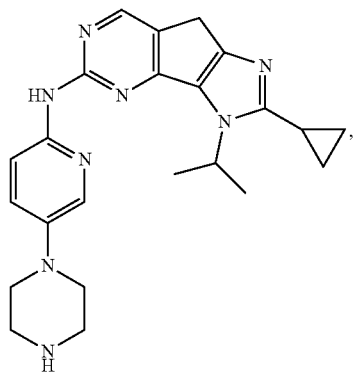 [SMILES: CC(C)n1c(C2CC2)nc2c1-c1nc(Nc3ccc(N4CCNCC4)cn3)ncc1C2]
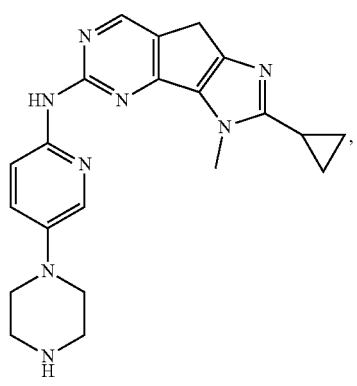 [SMILES: Cn1c(C2CC2)nc2c1-c1nc(Nc3ccc(N4CCNCC4)cn3)ncc1C2]
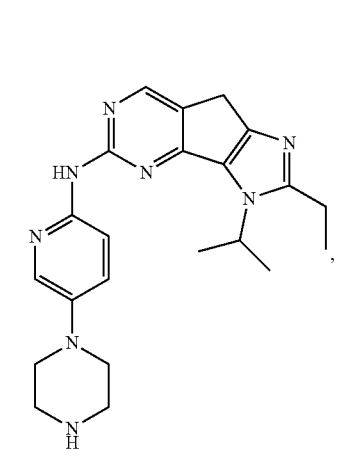 [SMILES: CCc1nc2c(n1C(C)C)-c1nc(Nc3ccc(N4CCNCC4)cn3)ncc1C2]
146
-continued
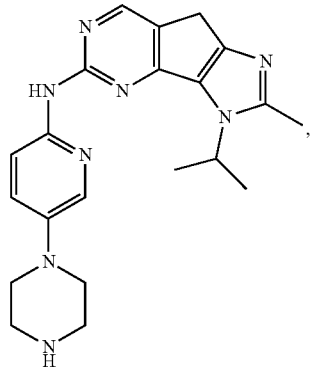 [SMILES: Cc1nc2c(n1C(C)C)-c1nc(Nc3ccc(N4CCNCC4)cn3)ncc1C2]
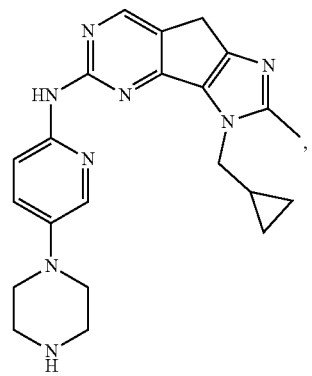 [SMILES: Cc1nc2c(n1CC1CC1)-c1nc(Nc3ccc(N4CCNCC4)cn3)ncc1C2]
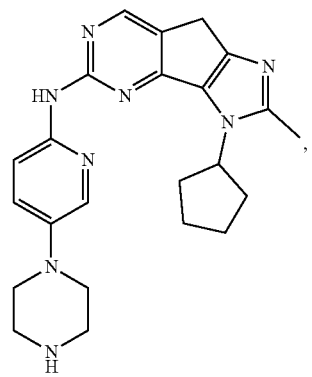 [SMILES: Cc1nc2c(n1C1CCCC1)-c1nc(Nc3ccc(N4CCNCC4)cn3)ncc1C2]
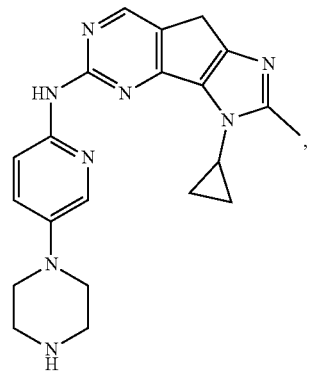 [SMILES: Cc1nc2c(n1C1CC1)-c1nc(Nc3ccc(N4CCNCC4)cn3)ncc1C2]

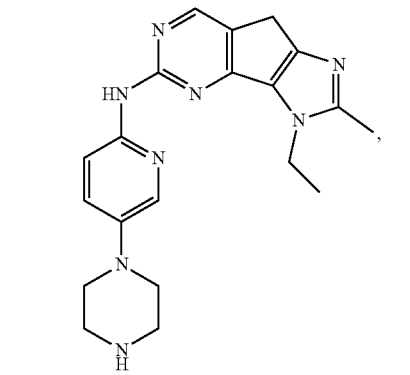 [SMILES: CCn1c(C)nc2c1-c1nc(Nc3ccc(N4CCNCC4)cn3)ncc1C2]
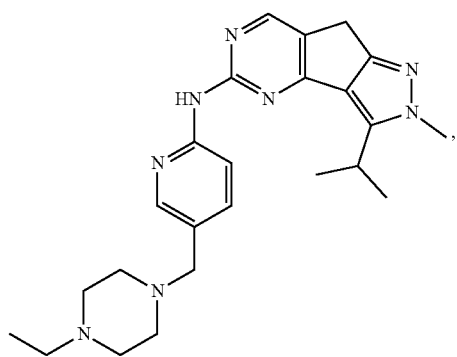 [SMILES: CCN1CCN(Cc2ccc(Nc3ncc4c(n3)-c3c(nn(C)c3C(C)C)C4)nc2)CC1]
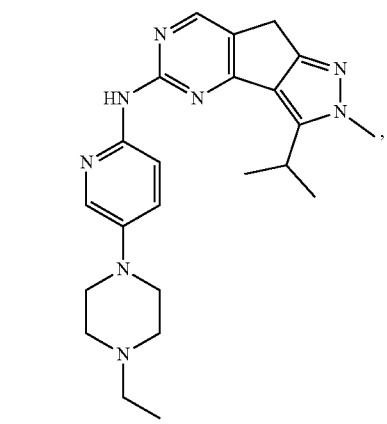 [SMILES: CCN1CCN(c2ccc(Nc3ncc4c(n3)-c3c(nn(C)c3C(C)C)C4)nc2)CC1]
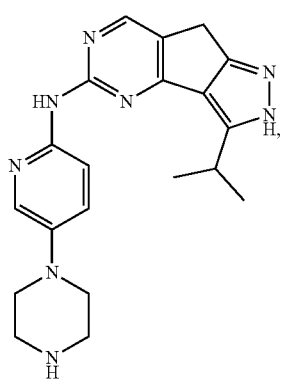 [SMILES: CC(C)c1[nH]nc2c1-c1nc(Nc3ccc(N4CCNCC4)cn3)ncc1C2]
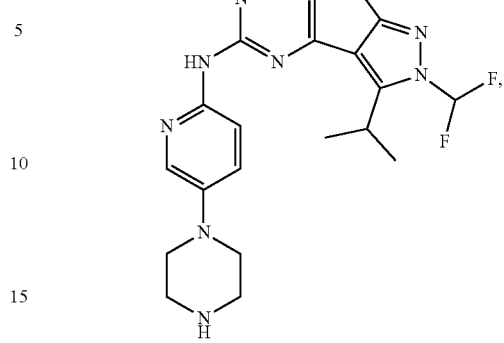
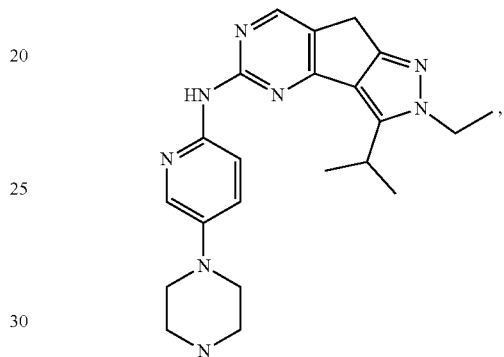
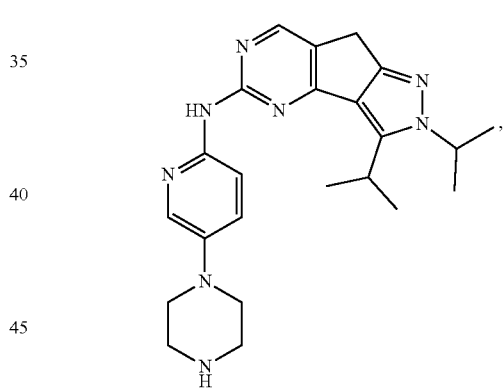
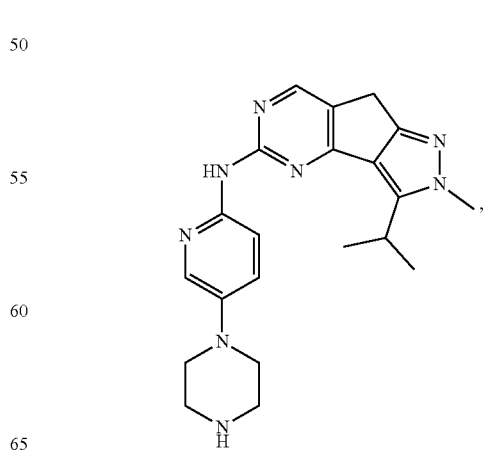

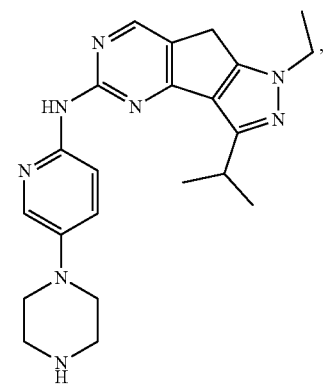 [SMILES: CCn1nc(C(C)C)c2c1Cc1cnc(Nc3ccc(N4CCNCC4)cn3)nc1-2]
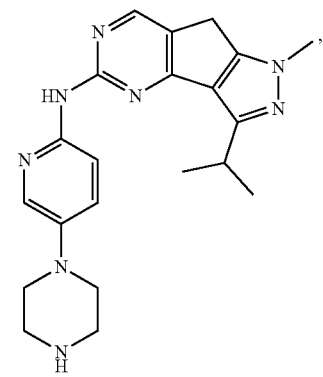 [SMILES: CC(C)c1nn(C)c2c1-c1nc(Nc3ccc(N4CCNCC4)cn3)ncc1C2]
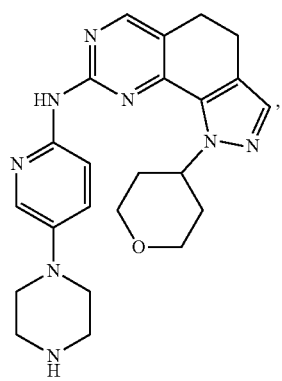 [SMILES: c1cc(Nc2ncc3c(n2)-c2c(cnn2C2CCOCC2)CC3)ncc1N1CCNCC1]
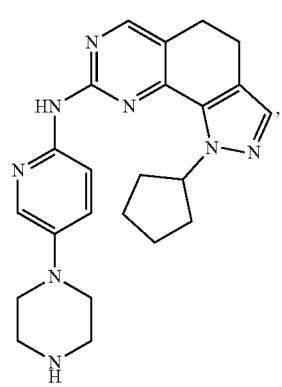 [SMILES: c1cc(Nc2ncc3c(n2)-c2c(cnn2C2CCCC2)CC3)ncc1N1CCNCC1]
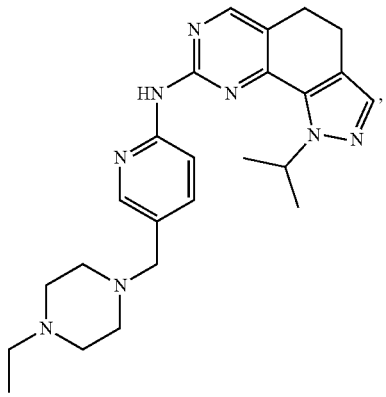 [SMILES: CCN1CCN(Cc2ccc(Nc3ncc4c(n3)-c3c(cnn3C(C)C)CC4)nc2)CC1]
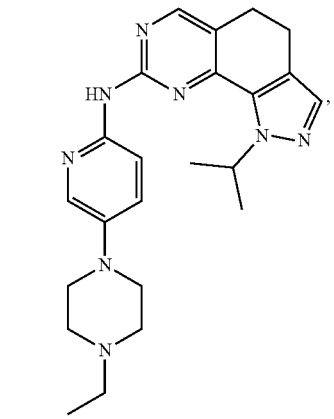 [SMILES: CCN1CCN(c2ccc(Nc3ncc4c(n3)-c3c(cnn3C(C)C)CC4)nc2)CC1]
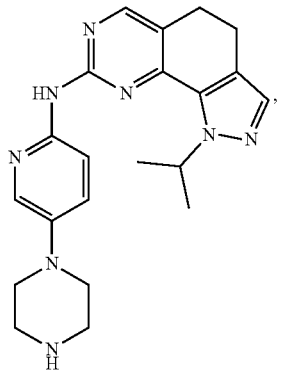 [SMILES: CC(C)n1ncc2c1-c1nc(Nc3ccc(N4CCNCC4)cn3)ncc1CC2]
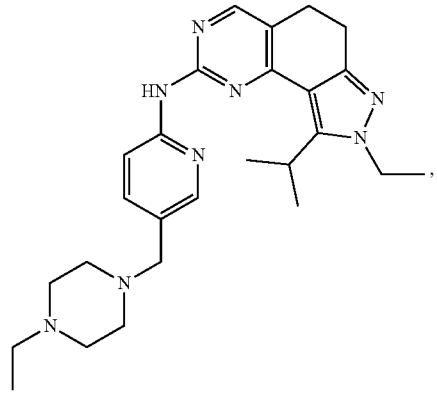 [SMILES: CCN1CCN(Cc2ccc(Nc3ncc4c(n3)-c3c(nn(CC)c3C(C)C)CC4)nc2)CC1]

151
-continued
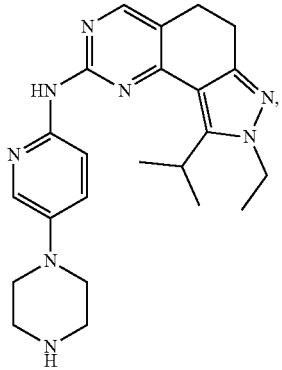 [SMILES: CCn1nc2c(c1C(C)C)-c1nc(Nc3ccc(N4CCNCC4)cn3)ncc1CC2]
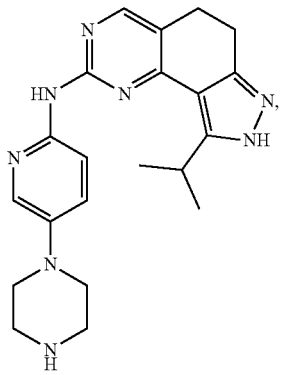 [SMILES: CC(C)c1[nH]nc2c1-c1nc(Nc3ccc(N4CCNCC4)cn3)ncc1CC2]
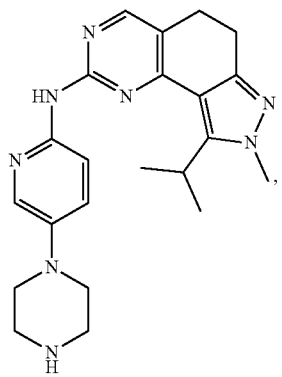 [SMILES: CC(C)c1c2c(nn1C)CCc1cnc(Nc3ccc(N4CCNCC4)cn3)nc1-2]
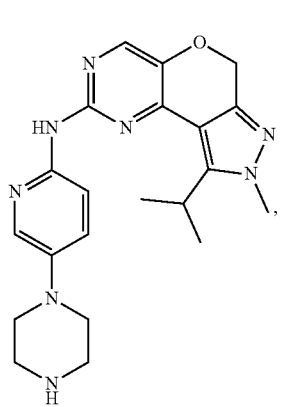 [SMILES: CC(C)c1c2c(nn1C)COc1cnc(Nc3ccc(N4CCNCC4)cn3)nc1-2]
152
-continued
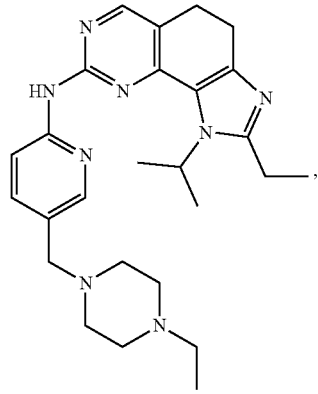 [SMILES: CCc1nc2c(n1C(C)C)-c1nc(Nc3ccc(CN4CCN(CC)CC4)cn3)ncc1CC2]
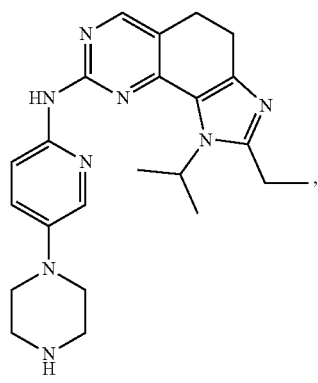 [SMILES: CCc1nc2c(n1C(C)C)-c1nc(Nc3ccc(N4CCNCC4)cn3)ncc1CC2]
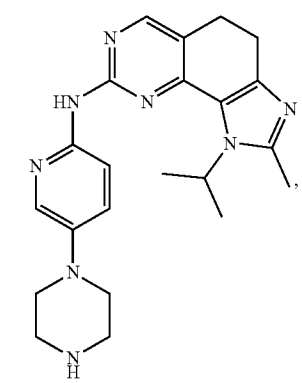 [SMILES: Cc1nc2c(n1C(C)C)-c1nc(Nc3ccc(N4CCNCC4)cn3)ncc1CC2]
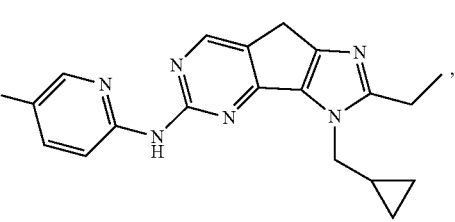

153
-continued
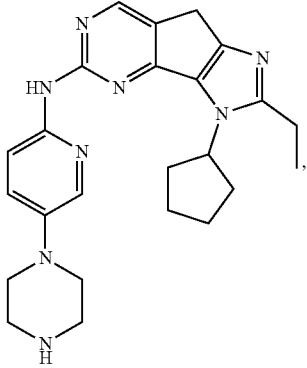 [SMILES: CCc1nc2c(n1C1CCCC1)-c1nc(Nc3ccc(N4CCNCC4)cn3)ncc1C2]
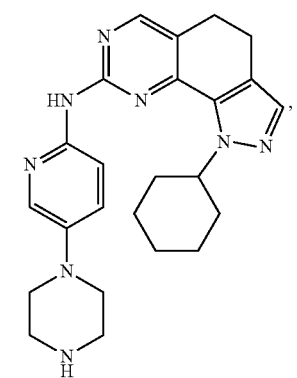 [SMILES: c1cc(Nc2ncc3c(n2)-c2c(cnn2C2CCCCC2)CC3)ncc1N1CCNCC1]
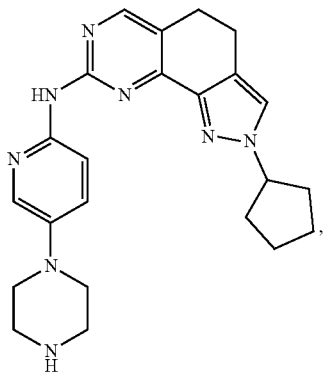 [SMILES: c1cc(Nc2ncc3c(n2)-c2nn(C4CCCC4)cc2CC3)ncc1N1CCNCC1]
154
-continued
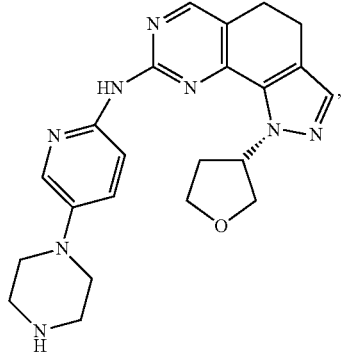
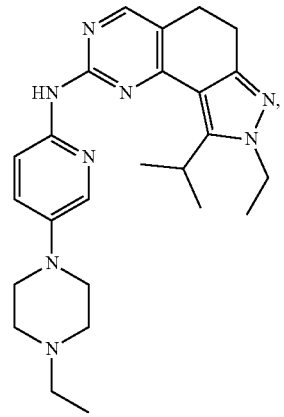 [SMILES: CCN1CCN(c2ccc(Nc3ncc4c(n3)-c3c(nn(CC)c3C(C)C)CC4)nc2)CC1]
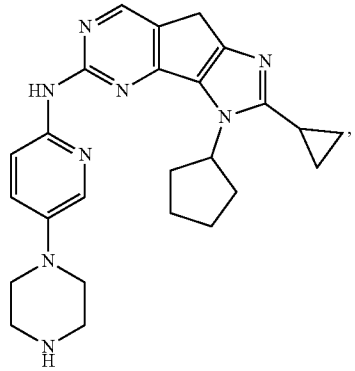 [SMILES: c1cc(Nc2ncc3c(n2)-c2c(nc(C4CC4)n2C2CCCC2)C3)ncc1N1CCNCC1]
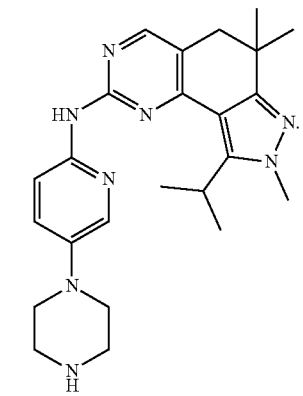 [SMILES: CC(C)c1c2c(nn1C)C(C)(C)Cc1cnc(Nc3ccc(N4CCNCC4)cn3)nc1-2]
* * * * *